US011897966B2

United States Patent
Zhao et al.

(10) Patent No.: US 11,897,966 B2
(45) Date of Patent: Feb. 13, 2024

(54) MESOTHELIN-TARGETTING ANTIBODIES, CHIMERIC ANTIGEN RECEPTORS, AND USES THEREOF

(71) Applicant: UTC THERAPEUTICS (SHANGHAI) CO., LTD., Shanghai (CN)

(72) Inventors: Yangbing Zhao, Shanghai (CN); Gengzhen Zhu, Shanghai (CN); Xiaojun Liu, Shanghai (CN)

(73) Assignee: UTC THERAPEUTICS (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 18/062,084

(22) Filed: Dec. 6, 2022

(65) Prior Publication Data
US 2023/0235081 A1    Jul. 27, 2023

Related U.S. Application Data

(63) Continuation of application No. PCT/CN2022/112726, filed on Aug. 16, 2022.

(30) Foreign Application Priority Data

Aug. 16, 2021 (WO) ................ PCT/CN2021/112855

(51) Int. Cl.
*C07K 16/30* (2006.01)
*C07K 14/725* (2006.01)
*C07K 14/705* (2006.01)

(52) U.S. Cl.
CPC .......... *C07K 16/30* (2013.01); *C07K 14/7051* (2013.01); *C07K 14/70517* (2013.01); *C07K 14/70578* (2013.01); *C07K 2317/622* (2013.01); *C07K 2319/02* (2013.01); *C07K 2319/03* (2013.01)

(58) Field of Classification Search
CPC .............. C07K 16/30; C07K 14/7051; C07K 14/70517; C07K 14/70578; C07K 2317/622; C07K 2319/02; C07K 2319/03
See application file for complete search history.

(56) References Cited

PUBLICATIONS

Rabia et al Understanding and overcoming trade-offs between antibody affinity, specificity, stability and solubility (Biochemical Engineering Journal 137 (2018) 365-374) (Year: 2018).*
Goel et al. Plasticity within the Antigen-Combining Site May Manifest as Molecular Mimicry in the Humoral Immune Response. J Immunol (2004) 173 (12): 7358-7367. (Year: 2004).*
Lloyd et al. Modelling the human immune response: performance of a 1011 human antibody repertoire against a broad panel of therapeutically relevant antigens. Protein Engineering, Design & Selection vol. 22 No. 3 pp. 159-168, 2009. (Year: 2009).*
Townsend et al. Significant Differences in Physiochemical Properties of Human Immunoglobulin Kappa and Lambda CDR3 Regions. Frontiers in Immunology. Sep. 2016, vol. 7, article 388. (Year: 2016).*

* cited by examiner

*Primary Examiner* — Amy E Juedes
*Assistant Examiner* — Brian Hartnett
(74) *Attorney, Agent, or Firm* — Oblon, McClelland, Maier & Neustadt, L.L.P.

(57) ABSTRACT

Disclosed herein are anti-mesothelin antibodies and antigen-binding fragments, chimeric antigen receptors ("CARs") having these anti-mesothelin antibodies and antigen-binding fragments ("mesothelin CARs") and genetically modified immune effector cells having such mesothelin CARs. Polynucleotides encoding the anti-mesothelin antibodies and antigen-binding fragments and mesothelin CARs are also provided herein. Compositions comprising anti-mesothelin antibodies and antigen-binding fragments and mesothelin CARs are also provided herein. The present disclosure also relates to uses of the anti-mesothelin antibodies and antigen-binding fragments and genetically modified immune effector cells having such mesothelin CARs in cancer treatment.

Figure 2:
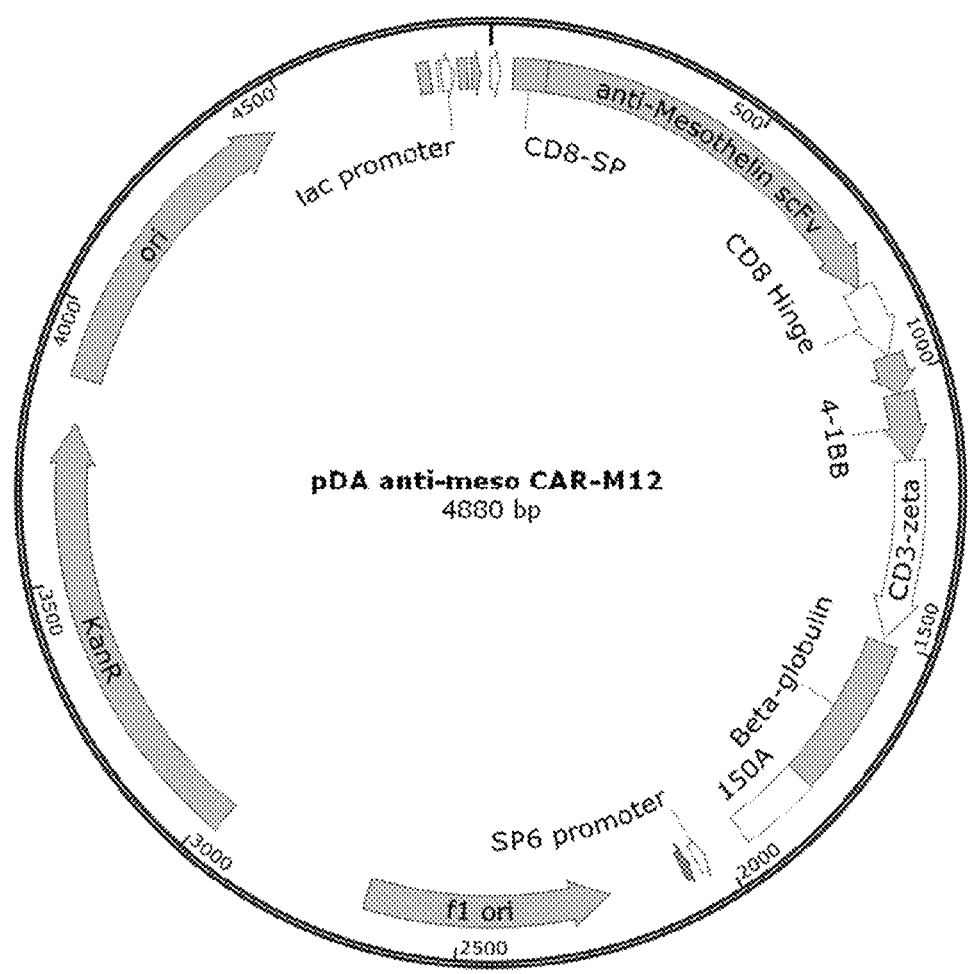

28 Claims, 10 Drawing Sheets
Specification includes a Sequence Listing.

ELISA Plate-1:

|   | 1 | 2 | 3 | 4 | 5 | 6 | 7 | 8 | 9 | 10 | 11 | 12 |
|---|---|---|---|---|---|---|---|---|---|---|---|---|
| A | 0.885 | 1.13 | 1.447 | 1.313 | 1.257 | 1.422 | 1.316 | 1.385 | 1.036 | 1.187 | 0.913 | 0.008 |
| B | 1.066 | 1.452 | 1.408 | 1.715 | 1.555 | 1.44 | 1.538 | 0.004 | 1.333 | 1.239 | 1.235 | 0.965 |
| C | 1.52 | 1.423 | 1.636 | 1.739 | 1.776 | 1.709 | 1.687 | 1.562 | 1.545 | 1.384 | 1.083 | 1.08 |
| D | 1.411 | 1.596 | 1.859 | 1.837 | 1.801 | 2.053 | 0.003 | 1.636 | 1.691 | 1.487 | 1.476 | 1.28 |
| E | 1.354 | 1.718 | 0.006 | 1.693 | 1.935 | 1.848 | 2.006 | 1.303 | 1.781 | 1.293 | 1.437 | 0.956 |
| F | 1.264 | 1.6 | 1.802 | 1.838 | 1.848 | 1.778 | 0.004 | 1.564 | 0 | 1.152 | 1.572 | 1.085 |
| G | 1.258 | 0.008 | 1.852 | 1.556 | 1.463 | 1.558 | 1.694 | 1.563 | 1.713 | 1.301 | 1.33 | 0.004 |
| H | 1.081 | 0.008 | 0.007 | 1.305 | 0.007 | 1.643 | 0.005 | 1.674 | 1.732 | 1.522 | 1.214 | 0.008 |

ELISA Plate-2:

|   | 1 | 2 | 3 | 4 | 5 | 6 | 7 | 8 | 9 | 10 | 11 | 12 |
|---|---|---|---|---|---|---|---|---|---|---|---|---|
| A | 1.332 | 1.075 | 1.619 | 1.437 | 1.649 | 1.259 | 1.466 | 1.1 | 1.475 | 1.336 | 1.459 | 1.075 |
| B | 1.183 | 0.004 | 0.004 | 1.517 | 1.919 | 1.942 | 1.753 | 1.913 | 1.667 | 0.001 | 1.659 | 1.197 |
| C | 2.564 | 1.854 | 0.005 | 2.208 | 2.563 | 2.186 | 1.607 | 1.977 | 2.855 | 2.902 | 2.374 | 1.638 |
| D | 1.117 | 1.28 | 1.55 | 1.577 | 1.617 | 1.991 | 1.615 | 1.602 | 1.936 | 1.528 | 1.093 | 0.004 |
| E | 0.005 | 1.586 | 1.916 | 1.651 | 0.005 | 1.67 | 1.542 | 1.494 | 2.145 | 1.5 | 2.129 | 0.006 |
| F | 1.337 | 1.598 | 1.746 | 1.725 | 1.823 | 1.984 | 0.003 | 0.002 | 1.439 | 1.818 | 0.955 | 1.569 |
| G | 1.13 | 1.347 | 1.784 | 1.882 | 1.676 | 1.441 | 1.89 | 1.488 | 1.975 | 1.771 | 1.995 | 1.556 |
| H | 1.244 | 1.532 | 1.653 | 1.28 | 1.345 | 0.002 | 1.69 | 0.005 | 0.002 | 0.003 | 0.793 | 1.669 |

FIG.1 ional mesothelin-targeting therapeutic options represent unmet needs. The compositions and methods provided herein meet these needs and provide other relative advantages.

MESOTHELIN-TARGETTING ANTIBODIES, CHIMERIC ANTIGEN RECEPTORS, AND USES THEREOF

This application is a continuation of PCT/CN2022/112726, filed Aug. 16, 2022, which claims the benefit of PCT application PCT/CN2021/112855, filed Aug. 16, 2021, the contents of both are incorporated herein by reference.

REFERENCE TO A SEQUENCE LISTING

In accordance with 37 CFR § 1.831, the present specification makes reference to a Sequence Listing submitted electronically as a .xml file named "545411US_ST26". The .xml file was generated on Nov. 24, 2022 and is 35,624 bytes in size. The entire contents of the Sequence Listing are hereby incorporated by reference.

1. FIELD

The present invention relates to molecular biology, cell biology, and immuno-oncology. In particular, provided herein include anti-mesothelin antibodies, chimeric antigen receptors (CARs) comprising such anti-mesothelin antibodies ("mesothelin CARs"), genetically engineered immune effector cells expressing such mesothelin CARs, and uses thereof in treating tumors or cancers.

2. BACKGROUND

Cell-based immunotherapy is a therapy with curative potential for the treatment of cancer. T cells and other immune cells can be modified to target tumor antigens through the introduction of genetic material coding for artificial or synthetic receptors for antigen, such as Chimeric Antigen Receptors (CARs), specific to selected antigens. Targeted T cell therapy using CARs (CARTs) has shown recent clinical success in treating some hematologic malignancies. However, translating CAR-expressing T cell therapy to solid tumors poses several obstacles that must be overcome to achieve clinical benefit. Accordingly, there are needs for novel therapeutic strategies to design CARs for treating cancers, particularly, solid tumors, which strategies capable of inducing potent tumor eradication with minimal toxicity and immunogenicity. Mesothelin is expressed in a variety of human cancers, such as mesothelioma, pancreatic cancer, and ovarian cancer. Current therapies targeting mesothelin, however, have only had limited success. Thus, additional mesothelin-targeting therapeutic options represent unmet needs. The compositions and methods provided herein meet these needs and provide other relative advantages.

3. SUMMARY

Provided herein are antibodies or antigen-binding fragments thereof that specifically bind mesothelin (e.g., human mesothelin), comprising: (a) a light chain variable region (VL) comprising a light chain CDR1 (VL CDR1), a light chain CDR2 (VL CDR2), and a light chain CDR3 (VL CDR3) having amino acid sequences of SEQ ID NOs: 1, 2, and 3, or a variant thereof having up to about 5 amino acid substitutions, additions, and/or deletions in the VL CDRs; and/or (b) a heavy chain variable region (VH) comprising a heavy chain CDR1 (VH CDR1), a heavy chain CDR2 (VH CDR2), and a heavy chain CDR3 (VH CDR3) having amino acid sequences of SEQ ID NOs: 4, 5, and 6, or a variant thereof having up to about 5 amino acid substitutions, additions, and/or deletions in the VH CDRs.

In some embodiments, the antibodies or antigen-binding fragments provide herein comprise a VL CDR1, a VL CDR2, a VL CDR3, a VH CDR1, a VH CDR2 and a VH CDR3, wherein (a) the VL CDR1, CDR2 and CDR3 have the amino acid sequences of SEQ ID NOs: 1, 2, and 3 respectively; and (b) the VH CDR1, CDR2 and CDR3 have the amino acid sequences of SEQ ID NOs: 4, 5, and 6 respectively.

Provided herein are antibodies or antigen-binding fragments thereof that specifically bind mesothelin, comprising: (a) a VL having at least 85%, at least 90%, at least 95%, at least 98%, or 100% sequence identity to an amino acid sequence of SEQ ID NO: 7; and/or (b) a VH having at least 85%, at least 90%, at least 95%, at least 98%, or 100% sequence identity to an amino acid sequence of SEQ ID NO: 8.

In some embodiments, the antibodies or antigen-binding fragments provide herein comprise a VL and a VH, wherein the VL and VH have the amino acid sequences of SEQ ID NOs: 7 and 8 respectively.

Provided herein are antibodies or antigen-binding fragments thereof that specifically bind mesothelin, comprising (a) a VL comprising VL CDR1, CDR2, and CDR3 from a VL having an amino acid sequence of SEQ ID NO: 7; and/or (b) a VH comprising VH CDR1, CDR2, and CDR3 from a VH having an amino acid sequence of SEQ ID NO: 8.

In some embodiments, provided herein are antibodies or antigen-binding fragments thereof that compete with an antibody or antigen-binding fragment described herein for binding to mesothelin.

In some embodiments, the antibody or antigen-binding fragment is a monoclonal antibody or antigen-binding fragment.

In some embodiments, the antibody or antigen-binding fragment is a bispecific or multispecific antibody.

In some embodiments, the antibody or antigen-binding fragment is a Bi-specific T-cell engager (BiTE).

In some embodiments, the antibody provided herein is selected from the group consisting of an IgG1 antibody, an IgG2 antibody, an IgG3 antibody, and an IgG4 antibody.

In some embodiments, the antibody or antigen-binding fragment provided herein is selected from the group consisting of a Fab, a Fab', a F(ab')2, a Fv, a scFv, a (scFv)2, a single domain antibody (sdAb), and a heavy chain antibody (HCAb). In some embodiments, the antibody or antigen-binding fragment is a scFv.

In some embodiments, the antibody or antigen-binding fragment is a chimeric antibody or antigen-binding fragment, a humanized antibody or antigen-binding fragment, or a human antibody or antigen-binding fragment. In some embodiments, the antibody or antigen-binding fragment is a human antibody or antigen-binding fragment.

Provided herein are also polynucleotides encoding an antibody or antigen-binding fragment described herein. In some embodiments, the polynucleotide is a messenger RNA (mRNA).

Provided herein are vectors comprising a polynucleotide described herein.

Provided herein are also host cells comprising a polynucleotide described herein, or a vector described herein.

Provided herein are also Chimeric Antigen Receptors (CAR) that specifically bind mesothelin, comprising, from N-terminus to C-terminus: (a) a mesothelin-binding domain that comprises an antibody or antigen-binding fragment described herein; (b) a transmembrane domain; and (c) a cytoplasmic domain.

In some embodiments, the transmembrane domain is derived from CD8, CD28, CD3ζ, CD4, 4-1BB, OX40, ICOS, CTLA-4, PD-1, LAG-3, 2B4, BTLA, TCR α chain, TCR β chain, or TCR ζ chain, CD3ε, CD45, CD5, CD8, CD9, CD16, CD22, CD33, CD37, CD64, CD80, CD86, CD134, or CD154.

In some embodiments, the transmembrane domain comprises CD8 transmembrane region or CD28 transmembrane region.

In some embodiments, the cytoplasmic domain comprises a signaling domain derived from CD3ζ, FcRγ, FcγRIIa, FcRβ, CD3γ, CD3δ, CD3ε, CD5, CD22, CD79a, CD79b, DAP10, DAP12, or any combination thereof.

In some embodiments, the cytoplasmic domain further comprises a co-stimulatory domain derived from CD28, 4-1BB (CD137), OX40, ICOS, DAP10, 2B4, CD27, CD30, CD40, CD2, CD7, LIGHT, GITR, TLR, DR3, CD43, or any combination thereof.

In some embodiments, the cytoplasmic domain comprises a CD3ζ signaling domain and a 4-1BB co-stimulatory domain.

In some embodiments, the cytoplasmic domain comprises a CD3ζ signaling domain and a CD28 co-stimulatory domain.

In some embodiments, the CARs provided herein further comprise a CD8 hinge between the antibody or antigen-binding fragment and the transmembrane domain.

In some embodiments, CARs provided herein that specifically bind mesothelin comprise an amino acid sequence of SEQ ID NO:12.

Provided herein are also polynucleotides encoding a CAR described herein.

In some embodiments, the polynucleotide is a mRNA.

Provided herein are also vectors comprising a polynucleotide described herein.

Provided herein are also cells comprising a polynucleotide described herein, or a vector described herein.

In some embodiments, the cell provided herein is an immune effector cell.

In some embodiments, the cell is isolated from peripheral blood or bone marrow.

In some embodiments, the cell is differentiated in vitro from a stem or progenitor cell of a T cell progenitor cell, a hematopoietic stem and progenitor cell, a hematopoietic multipotent progenitor cell, an embryonic stem cell, and an induced pluripotent cell.

In some embodiments, the cell is a T cell or a NK cell.

In some embodiments, the cell is a cytotoxic T cell, a helper T cell, a gamma delta T, a CD4+/CD8+ double positive T cell, a CD4+ T cell, a CD8+ T cell, a CD4/CD8 double negative T cell, a CD3+ T cell, a naive T cell, an effector T cell, a helper T cell, a memory T cell, a regulator T cell, a Th0 cell, a Th1 cell, a Th2 cell, a Th3 (Treg) cell, a Th9 cell, a Th17 cell, a Thαβ helper cell, a Tfh cell, a stem memory TSCM cell, a central memory TCM cell, an effector memory TEM cell, or an effector memory TEMRA cell. In some embodiments, the cell is a cytotoxic T cell.

In some embodiments, provided herein are populations of the cells described herein, wherein the populations of cells are derived from peripheral blood mononuclear cells (PBMC), peripheral blood leukocytes (PBL), tumor infiltrating lymphocytes (TIL), cytokine-induced killer cells (CIK), lymphokine-activated killer cells (LAK), or marrow infiltrate lymphocytes (MILs).

Provided herein are pharmaceutical compositions comprising a therapeutically effective amount of the antibody or antigen-binding fragment described herein, and a pharmaceutically acceptable carrier. Also provided herein are pharmaceutical compositions comprising a therapeutically effective amount of the cell or cell population described herein, and a pharmaceutically acceptable carrier.

Provided herein are uses of the antibody or antigen-binding fragment described herein, the cell or population of cells described here, or the pharmaceutical composition described herein in cancer treatment. Provided herein are also uses of the antibody or antigen-binding fragment described herein, the cell or population of cells described herein, or the pharmaceutical composition described herein for the preparation of a medicament for the treatment of cancer. In some embodiments of the uses described herein, the cell, population of cells, or pharmaceutical composition is used in combination with an additional therapy.

Provided herein are methods of treating cancer in a subject in need thereof, comprising administering to the subject a therapeutically effective amount of the antibody or antigen-binding fragment described herein, or the pharmaceutical composition described herein.

Provided herein are also methods of treating cancer in a subject in need thereof, comprising administering to the subject a therapeutically effective amount of the cell or cell population described herein. In some embodiments, the cell or population of cells is autologous to the subject.

In some embodiments, the methods provided herein further comprise obtaining cells from the subject. In some embodiments, the methods provided herein further comprise administering an additional therapy to the subject.

In some embodiments of the methods provided herein, the subject is a human.

In some embodiments of the uses or methods provided herein, the cancer is a mesothelin-expressing cancer.

In some embodiments, the cancer is a solid tumor or a hematological cancer. In some embodiments, the cancer is mesothelioma.

In some embodiments, the mesothelioma is pleural mesothelioma, peritoneal mesothelioma, or pericardial mesothelioma.

In some embodiments, the cancer is pancreatic cancer.

In some embodiments, the pancreatic cancer is pancreatic ductal carcinoma.

In some embodiments, the cancer is ovarian cancer.

In some embodiments, the ovarian cancer is ovarian epithelial carcinoma.

Provided herein are methods of preparing a cell capable of expressing a CAR that specifically binds mesothelin, comprising transferring a polynucleotide described herein into the cell. The cell can be selected from the group consisting of a T cell, an NK cell, an NKT cell, a macrophage, a neutrophil, and a granulocyte cell.

In some embodiments, the polynucleotide is transferred via electroporation.

In some embodiments, the polynucleotide is transferred via viral transduction.

In some embodiments, methods provided herein comprise using a lentivirus, a retrovirus, an adenovirus, or an adeno-associated virus for the viral transduction.

In some embodiments, the polynucleotide is transferred using a transposon system.

In some embodiments, the transposon system is Sleeping Beauty or PiggyBac.

In some embodiments, the polynucleotide is transferred using gene-editing.

In some embodiments, the polynucleotide is transferred using a CRISPR-Cas system, a ZFN system, or a TALEN system.

4. BRIEF DESCRIPTION OF DRAWINGS

FIG. 1 provides the reads of three 96-well plates of anti-human Mesothelin-Fc monoclonal phage ELISA.

FIG. 2 provides the schematic representation of pDA-CAR vector used for anti-mesothelin CAR mRNA generation.

Figure 3:
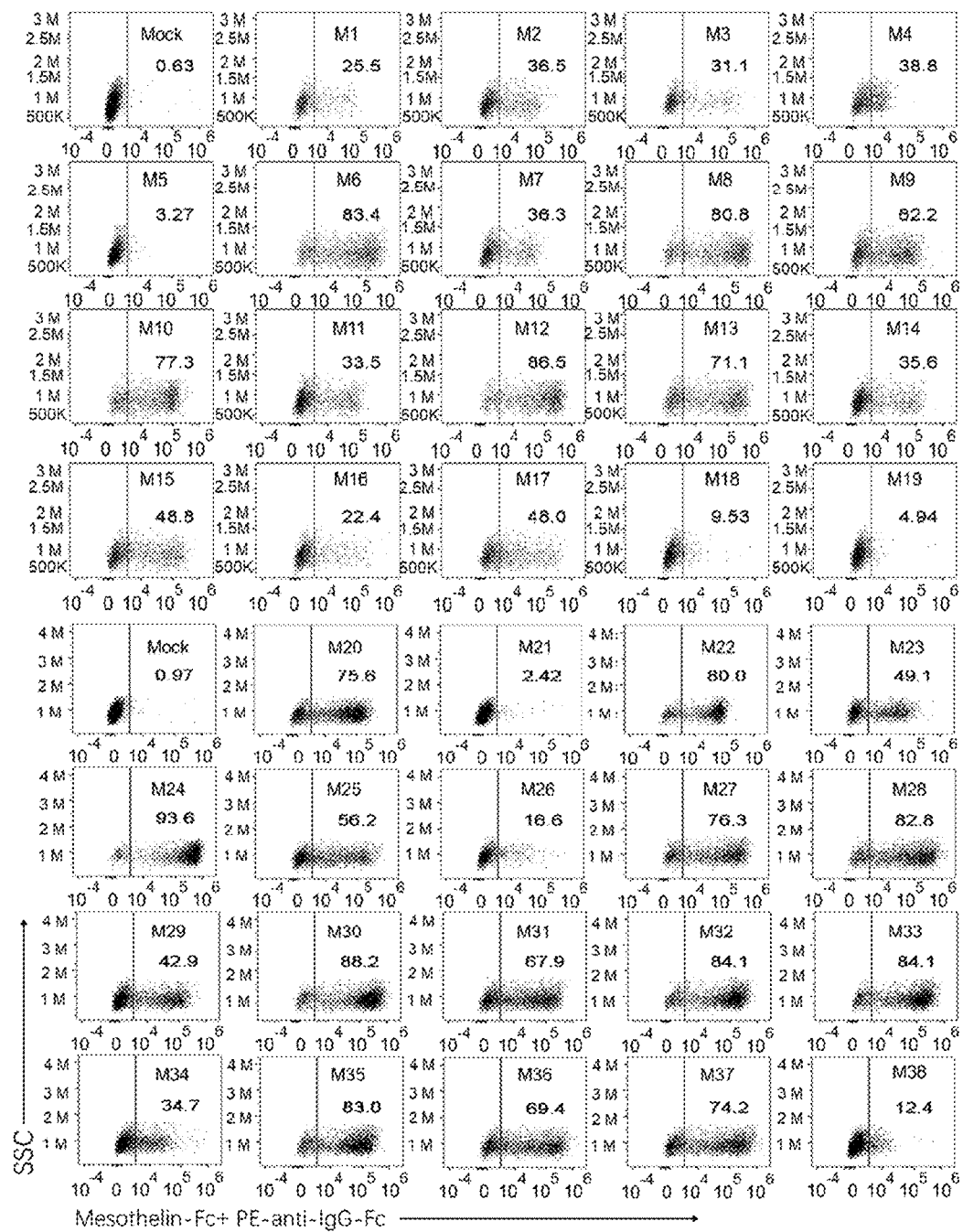

FIG. 3 provides FACS staining results showing the binding of anti-mesothelin scFv that expressed in CART cells to mesothelin-Fc protein.

Figure 4:
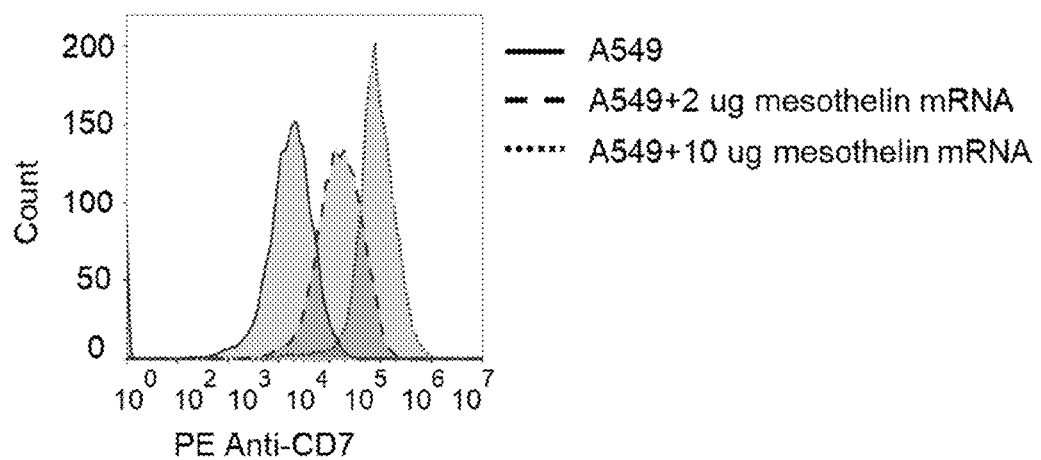

FIG. 4 provides FACS staining of the A549 cells that were electroporated with different amount of mesothelin mRNA by isotype and anti-mesothelin antibody.

Figure 5:
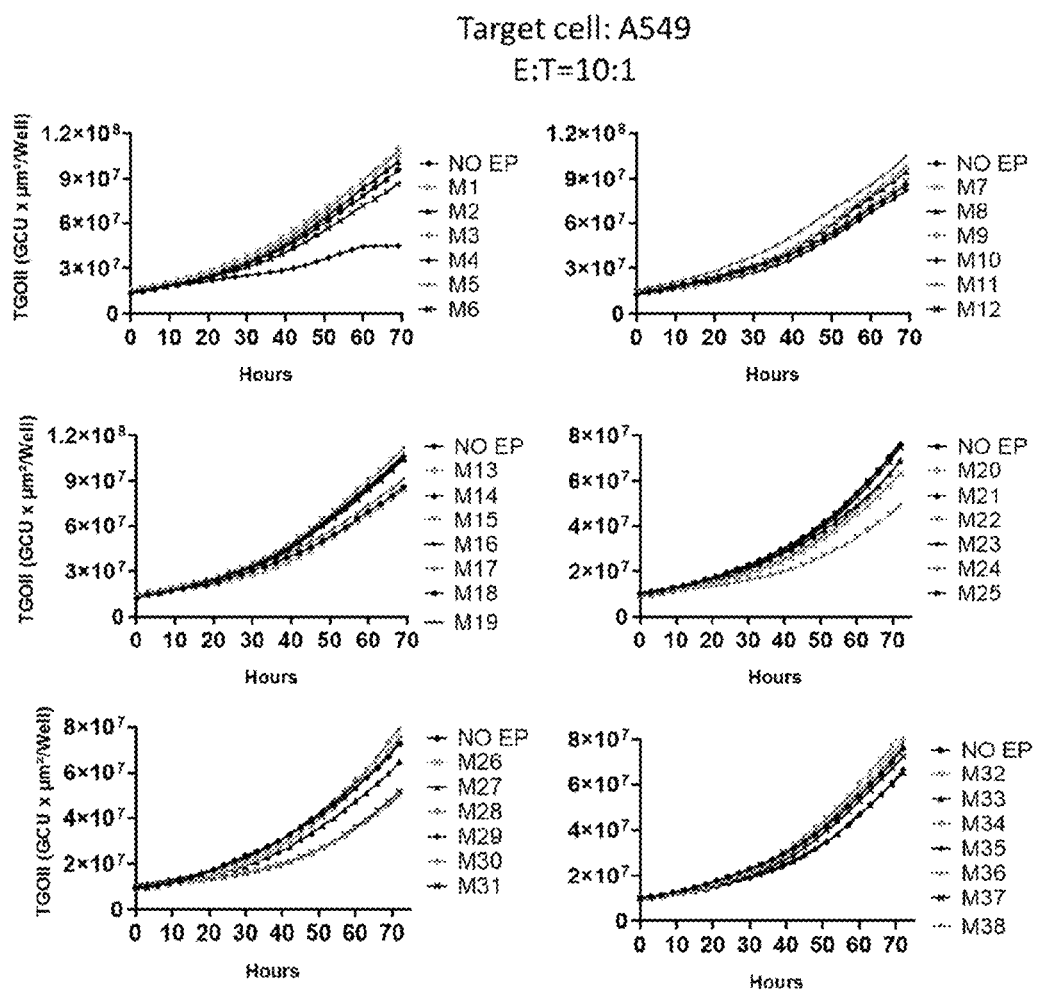

FIG. 5 provides the killing curves of different mRNA-based mesothelin CART cells against A549-GFP tumor cells at E/T ratio=10:1.

Figure 6:
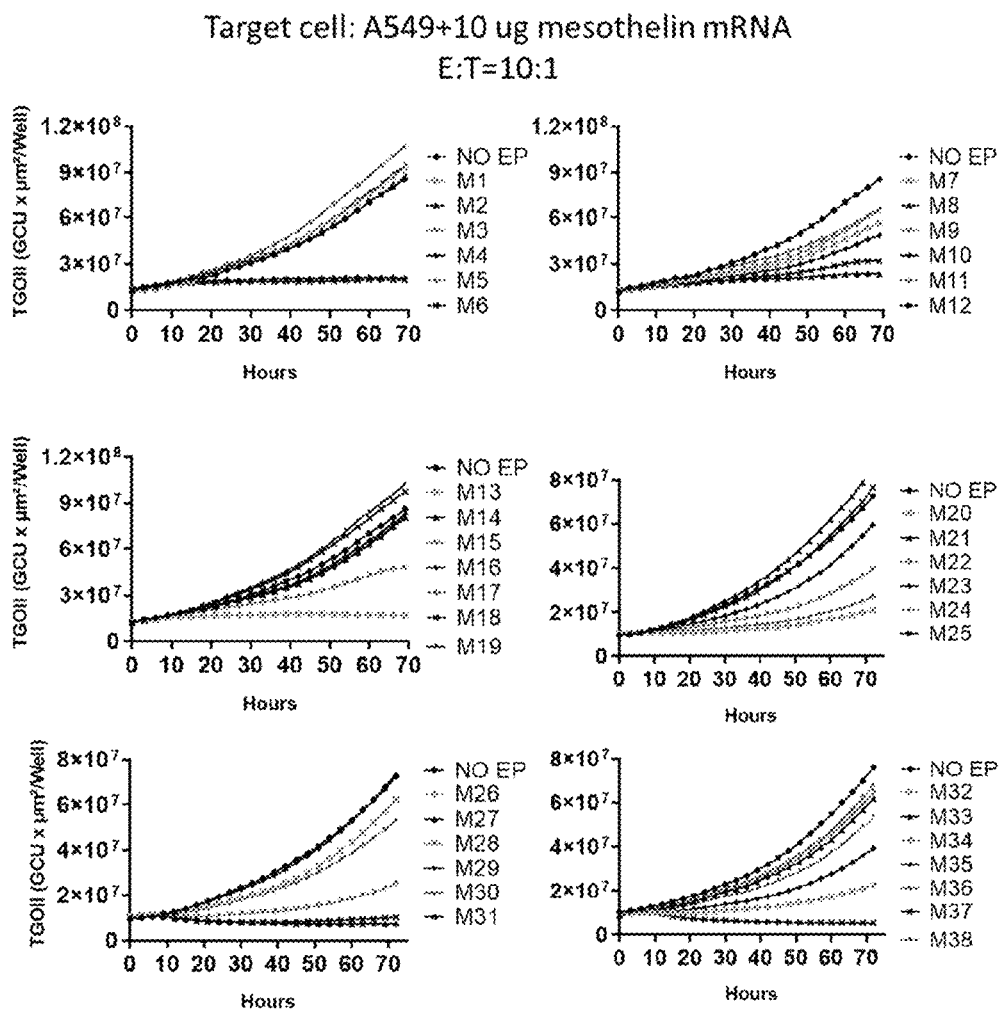

FIG. 6 provides the killing curves of different mRNA-based mesothelin CART cells against A549-GFP tumor cells that were electroporated with 10 μg mesothelin mRNA at E/T ratio=10:1.

Figure 7:
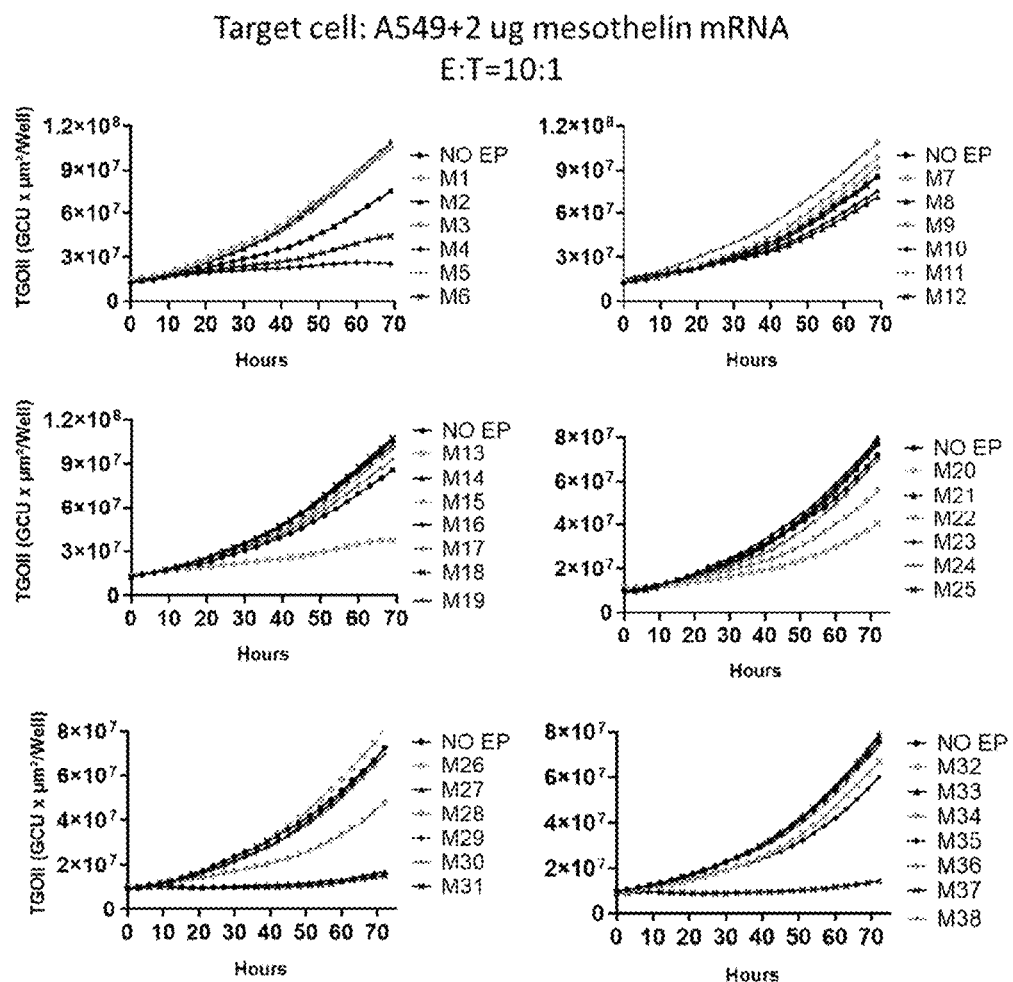

FIG. 7 provides the killing curves of different mRNA-based mesothelin CART cells against A549-GFP tumor cells that were electroporated with 2 μg mesothelin mRNA at E/T ratio=10:1.

Figure 8:
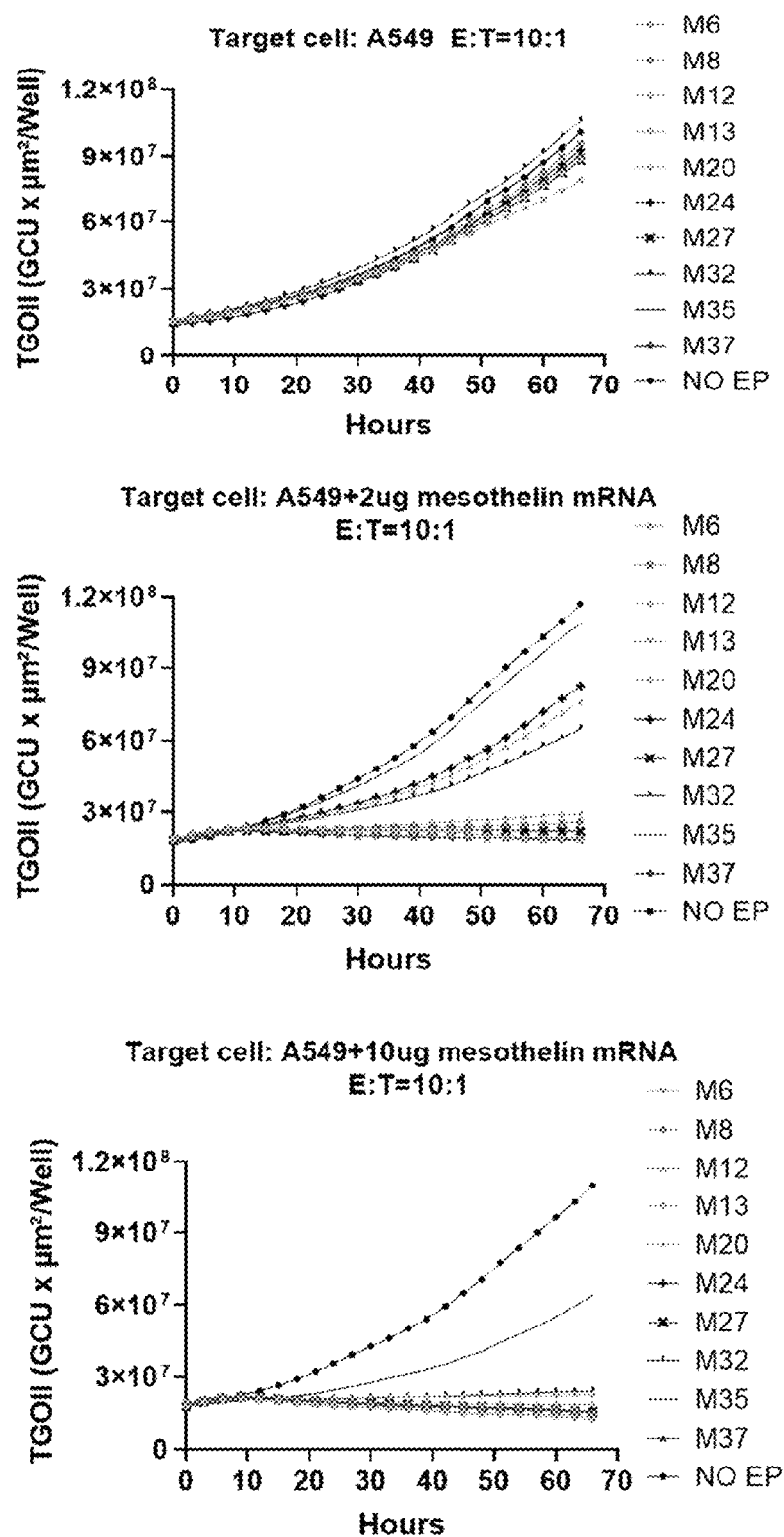

FIG. 8 provides the killing curves of different mRNA-based mesothelin CART cells against A549-GFP tumor cells that were electroporated with 0 μg, 2 μg or 10 μg mesothelin mRNA at E/T ratio=10:1.

Figure 9:
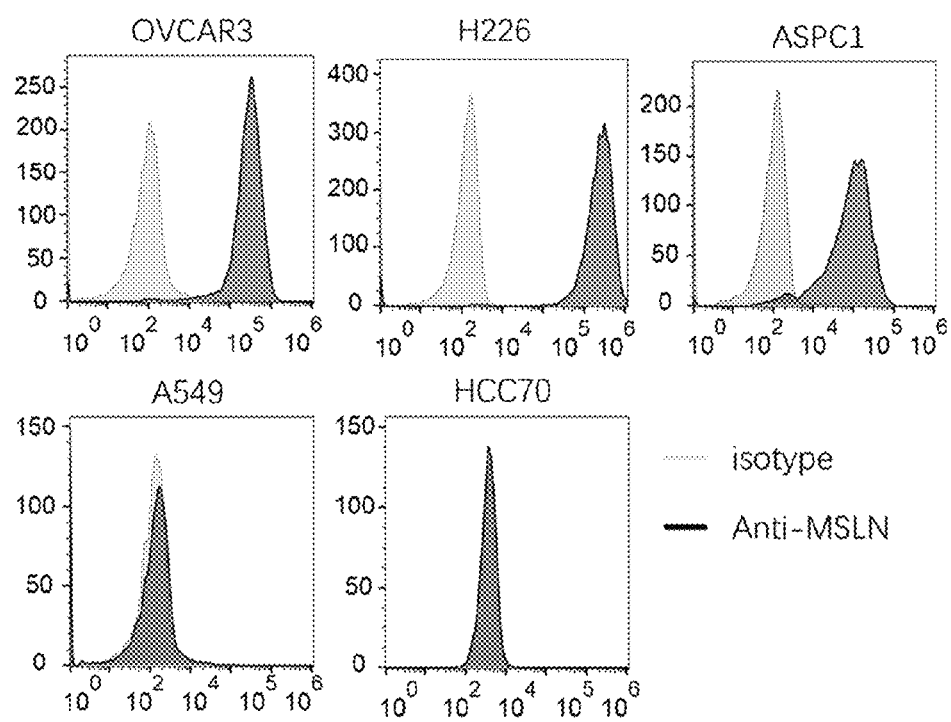

FIG. 9 provides FACS staining of OVCAR3, H226, ASPC1, A549 and HCC70 with isotype control and anti-mesothelin mAb.

Figure 10:
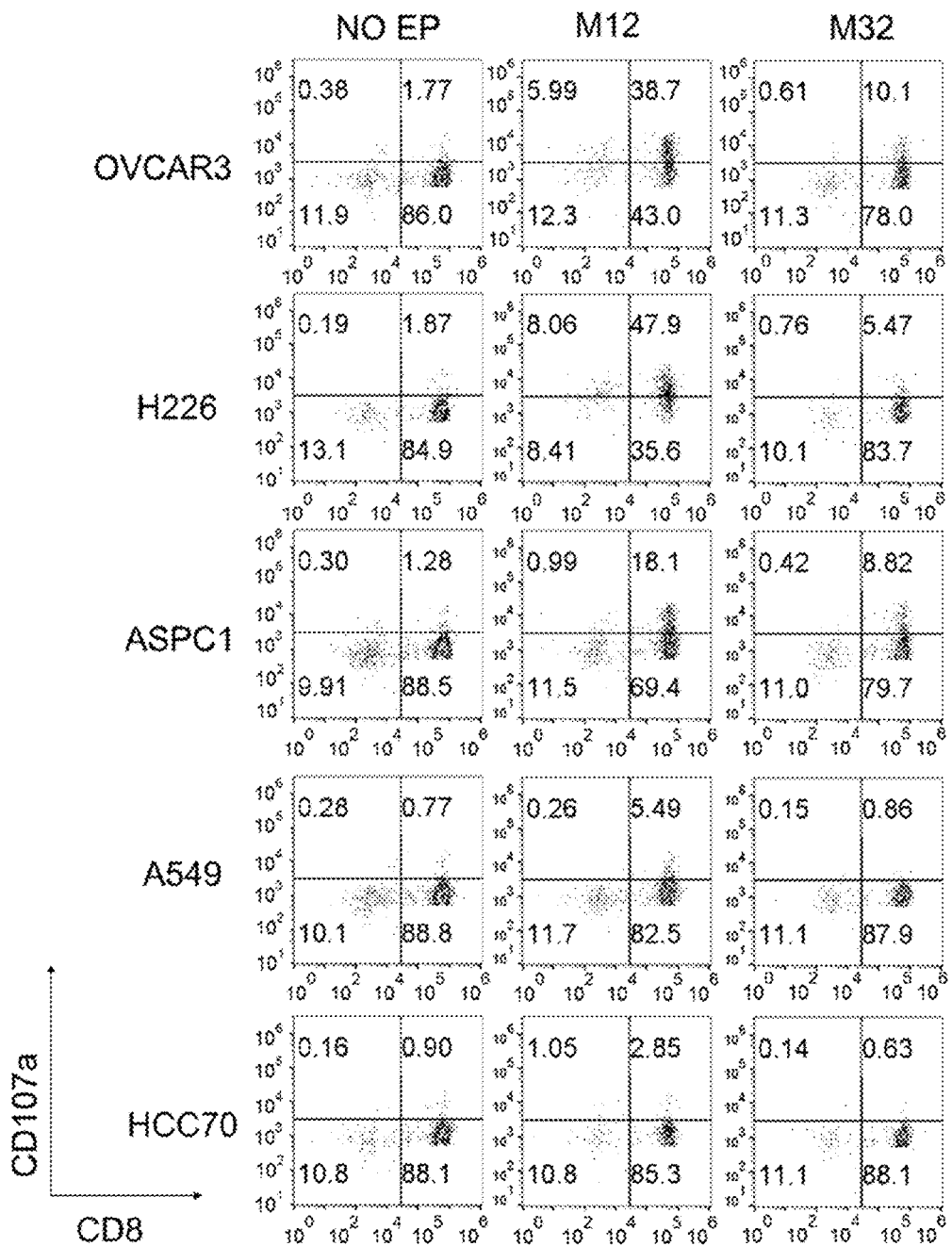

FIG. 10 provides CD107a staining of anti-mesothelin M12 and M32 CART cells in the coculture and killing assay with OVCAR3, H226, ASPC1, A549 and HCC70 tumor cell lines.

5. DETAILED DESCRIPTION

Before the present disclosure is further described, it is to be understood that the disclosure is not limited to the particular embodiments set forth herein, and it is also to be understood that the terminology used herein is for the purpose of describing particular embodiments, and is not intended to be limiting.

The present disclosure provides novel antibodies, including antigen-binding fragments that specifically bind mesothelin (e.g., human mesothelin). Further, the present disclosure also provides chimeric antigen receptors (CARs) that comprise such antibodies or antigen-binding fragments that specifically bind mesothelin (e.g., human mesothelin), as well as engineered immune effector cells (e.g., T cells) and populations of cells that recombinantly express a CAR (e.g., CARTs) that specifically binds mesothelin (e.g., human mesothelin). Pharmaceutical compositions comprising a therapeutically effective amount of such antibodies or antigen-binding fragments, and pharmaceutical compositions comprising a therapeutically effective amount of cells or population of cells are also disclosed herein. Also disclosed herein are uses of such pharmaceutical compositions for treating cancer (e.g., mesothelin-expressing cancer) and methods of cancer treatment.

Mesothelin was originally identified by Pastan and colleagues as a tumor associated antigen due to its limited expression by normal tissues and overexpression on tumors. Chang K, et al., *Cancer Res.* (1992) 52 (1):181-186 and Chang K, et al. *PNAS* (1996) 93 (1):136-140. The mesothelin gene encodes a precursor 71-kDa protein that is processed to yield the 40-kDa protein, mesothelin, which is anchored at the cell membrane by a glycosylphosphatidyl inositol (GPI) linkage and an amino-terminal 31-kDa shed fragment, called megkaryocyte potentiating factor (MPF). Both fragments contain N-glycosylation sites. A soluble splice variant of the 40-kDa carboxyl-terminal fragment called "soluble mesothelin/MPF-related" has been found in the sera of patients with pancreatic ductal adenocarcinoma (PDA). Johnston et al., *Clinical Cancer Research*. (2009) 15 (21):6511. Mesothelin was explored both as a therapeutic target as well as a bio-marker for disease activity and therapeutic response. Argani et al., *Clin Cancer Res*. (2001) 7(12):3862-3868.

Mesothelin is a differentiation antigen that is also present on normal tissues. Using the mouse anti-human mesothelin antibody K1 that was developed by the Pastan group, strong K1 reactivity has been demonstrated within mesothelial cells that line the peritoneal, pleural, and pericardial cavities, although at lower levels than usually seen for malignant tissues. Chang et al., *Cancer Res*. (1992) 52 (1):181-186. Weak K1 reactivity has been detected within the Fallopian tube epithelium, tracheal basal epithelium and tonsils epithelium. Mesothelin has also been found on all layers of the cornea. Jirsova et al. *Experimental eye research* (2010) 91(5):623-629. However, K1 reactivity has not been detected in the majority of normal tissues including the liver, kidneys, spleen, bone marrow, lymph nodes, thymus, cardiac muscle, tongue, skeletal muscle, skin, cerebral cortex, cerebellum, spinal cord, peripheral nerve, pituitary, adrenal, salivary gland, mammary gland, thyroid, parathyroid, testis, prostate, epididymis, cervical epithelium, lung parenchyma, esophagus, small-bowel epithelium, colon epithelium, bladder epithelium, gall-bladder epithelium. Chang 1992, supra.

Mesothelin is overexpressed in the vast majority of primary pancreatic adenocarcinomas with rare and weak expression seen in benign pancreatic tissue. Argani 2001, supra. Epithelial malignant pleural mesothelioma (MPM) universally expresses mesothelin while sarcomatoid MPM does not express mesothelin. Most serous epithelial ovarian carcinomas, and the related primary peritoneal carcinomas, express mesothelin.

Mesothelin is a target of a natural immune response in ovarian cancer, and has been a target for cancer immunotherapy. Bracci et al., *Clin Cancer Res*. (2007) 13 (2 Pt 1):644-653; Moschella et al., *Cancer Res*. (2011) 71 (10): 3528-3539; Sadelain et al., *Nat. Rev. Cancer* (2003) 3(1): 35-45; Muul et al., *Blood* (2003)101 (7):2563-2569; Yee et al., *Proc Natl Acad Sci USA*. (2002)99 (25):16168-16173. The presence of mesothelin-specific CTLs in patients with pancreatic cancer correlates with overall survival. Thomas et al., *J Exp Med*. (2004)200: 297-306. In addition, soluble antibody fragments of an anti-mesothelin antibody conjugated to immunotoxins were used to treat cancer patients with mesothelin-positive tumors, which demonstrated adequate safety and some clinical activity in pancreatic cancer. Hassan et al., *Clin Cancer Res*. (2007)13(17):5144-5149.

5.1 Definitions

Unless otherwise defined herein, scientific and technical terms used in the present disclosures shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The present disclosure provides novel antibodies, including antigen-binding fragments that specifically bind mesothelin (e.g., human mesothelin). The term "mesothelin" includes any variants or isoforms of mesothelin which are naturally expressed by cells. Accordingly, antibodies described herein can cross-react with mesothelin from species other than human (e.g., cynomolgus mesothelin). Alternatively, the antibodies can be specific for human mesothelin and do not exhibit any cross-reactivity with other species. mesothelin or any variants and isoforms thereof, can either be isolated from cells or tissues which naturally express them or be recombinantly produced using well-known techniques in the art and/or those described herein.

The term "antibody," and its grammatical equivalents as used herein refer to an immunoglobulin molecule that recognizes and specifically binds a target, such as a protein, polypeptide, peptide, carbohydrate, polynucleotide, lipid, or a combination of any of the foregoing, through at least one antigen-binding site wherein the antigen-binding site is usually within the variable region of the immunoglobulin molecule. As used herein, the term encompasses intact polyclonal antibodies, intact monoclonal antibodies, single-domain antibodies (sdAbs; e.g., camelid antibodies, alpaca antibodies), single-chain Fv (scFv) antibodies, heavy chain antibodies (HCAbs), light chain antibodies (LCAbs), multispecific antibodies, bispecific antibodies, monospecific antibodies, monovalent antibodies, and any other modified immunoglobulin molecule comprising an antigen-binding site (e.g., dual variable domain immunoglobulin molecules) as long as the antibodies exhibit the desired biological activity. Antibodies also include, but are not limited to, mouse antibodies, camel antibodies, chimeric antibodies, humanized antibodies, and human antibodies. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. Unless expressly indicated otherwise, the term "antibody" as used herein include "antigen-binding fragment" of intact antibodies. The term "antigen-binding fragment" as used herein refers to a portion or fragment of an intact antibody that is the antigenic determining variable region of an intact antibody. Examples of antigen-binding fragments include, but are not limited to, Fab, Fab', F(ab')2, Fv, linear antibodies, single chain antibody molecules (e.g., scFv), heavy chain antibodies (HCAbs), light chain antibodies (LCAbs), disulfide-linked scFv (dsscFv), diabodies, tribodies, tetrabodies, minibodies, dual variable domain antibodies (DVD), single variable domain antibodies (sdAbs; e.g., camelid antibodies, alpaca antibodies), and single variable domain of heavy chain antibodies (VHH), and bispecific or multispecific antibodies formed from antibody fragments.

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulin. In some instances, the Fv framework region residues of a human immunoglobulin are replaced with the corresponding residues in an antibody from a non-human species. In some instances, residues of the CDRs are replaced by residues from the CDRs of a non-human species (e.g., mouse, rat, hamster, camel) that have the desired specificity, affinity, and/or binding capability. The humanized antibody can be further modified by the substitution of additional residues either in the Fv framework region and/or within the replaced non-human residues to refine and optimize antibody specificity, affinity, and/or binding capability. The term "human antibody" as used herein refers to an antibody produced by a human or an antibody having an amino acid sequence corresponding to an antibody produced by a human made using any of the techniques known in the art.

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha ($\alpha$), delta ($\delta$), epsilon ($\varepsilon$), gamma ($\gamma$) and mu ($\mu$), based on the amino acid sequence of the heavy chain constant region. The distinct heavy chains differ in size: $\alpha$, $\delta$ and $\gamma$ contain approximately 450 amino acids, while $\mu$ and $\varepsilon$ contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa ($\kappa$) of lambda ($\lambda$) based on the amino acid sequence of the constant domains. Light chain amino acid sequences are well known in the art. A light chain can be a human light chain.

The term "variable domain" or "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) 5thed. A variable region can be a human variable region.

A CDR refers to one of three hypervariable regions (H1, H2 or H3) within the non-framework region of the immunoglobulin (Ig or antibody) VH $\beta$-sheet framework, or one of three hypervariable regions (L1, L2 or L3) within the non-framework region of the antibody VL $\beta$-sheet framework. Accordingly, CDRs are variable region sequences interspersed within the framework region sequences. CDR regions are well known to those skilled in the art and have been defined by a variety of methods/systems. These systems and/or definitions have been developed and refined over years and include Kabat, Chothia, IMGT, AbM, and Contact. For example, Kabat defines the regions of most hypervariability within the antibody variable (V) domains (Kabat et al, *J. Biol. Chem.* 252:6609-6616 (1977); Kabat, *Adv. Prot. Chem.* 32: 1-75 (1978)). The Chothia definition is based on the location of the structural loop regions, which defines CDR region sequences as those residues that are not part of the conserved β-sheet framework, and thus are able to adapt different conformations (Chothia and Lesk, *J. Mol. Biol.* 196:901-917 (1987)). Both terminologies are well recognized in the art. Additionally, the IMGT system is based on sequence variability and location within the structure of the variable regions. The AbM definition is a compromise between Kabat and Chothia. The Contact definition is based on analyses of the available antibody crystal structures. Software programs (e.g., abYsis) are available and known to those of skill in the art for analysis of antibody sequence and determination of CDRs. The positions of CDRs within a canonical antibody variable domain have been determined by comparison of numerous structures (Al-Lazikani et al, *J. Mol. Biol.* 273:927-948 (1997); Morea et al, *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to either the Kabat (hypervariable) or Chothia (structural) designations, are set forth in the table below.

|        | Kabat[1] | Chothia[2] | Loop Location            |
|--------|----------|------------|--------------------------|
| VHCDR1 | 31-35    | 26-32      | linking B and C strands  |
| VHCDR2 | 50-65    | 53-55      | linking C' and C" strands |
| VHCDR3 | 95-102   | 96-101     | linking F and G strands  |
| VLCDR1 | 24-34    | 26-32      | linking B and C strands  |
| VLCDR2 | 50-56    | 50-52      | linking C' and C" strands |
| VLCDR3 | 89-97    | 91-96      | linking F and G strands  |

[1]Residue numbering follows the nomenclature of Kabat et al., supra
[2]Residue numbering follows the nomenclature of Chothia et al., supra One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to bind to a particular antigen of interest. The CDR regions can be analyzed by, for example, abysis website (http://abysis.org/).

The terms "epitope" and "antigenic determinant" are used interchangeably herein an refer to the site on the surface of a target molecule to which an antibody or antigen-binding fragment binds, such as a localized region on the surface of an antigen. The target molecule can comprise, a protein, a peptide, a nucleic acid, a carbohydrate, or a lipid. An epitope having immunogenic activity is a portion of a target molecule that elicits an immune response in an animal. An epitope of a target molecule having antigenic activity is a portion of the target molecule to which an antibody binds, as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. The term, "epitope" includes linear epitopes and conformational epitopes. A region of a target molecule (e.g., a polypeptide) contributing to an epitope can be contiguous amino acids of the polypeptide or the epitope can come together from two or more non-contiguous regions of the target molecule. The epitope may or may not be a three-dimensional surface feature of the target molecule. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation.

The term "specifically binds," as used herein, means that a polypeptide or molecule interacts more frequently, more rapidly, with greater duration, with greater affinity, or with some combination of the above to the epitope, protein, or target molecule than with alternative substances, including related and unrelated proteins. A binding moiety (e.g., antibody) that specifically binds a target molecule (e.g., antigen) can be identified, for example, by immunoassays, ELISAs, SPR (e.g., Biacore), or other techniques known to those of skill in the art. Typically, a specific reaction will be at least twice background signal or noise and can be more than 10 times background. See, e.g., Paul, ed., 1989, *Fundamental Immunology Second Edition*, Raven Press, New York at pages 332-336 for a discussion regarding antibody specificity. A binding moiety that specifically binds a target molecule can bind the target molecule at a higher affinity than its affinity for a different molecule. In some embodiments, a binding moiety that specifically binds a target molecule can bind the target molecule with an affinity that is at least 20 times greater, at least 30 times greater, at least 40 times greater, at least 50 times greater, at least 60 times greater, at least 70 times greater, at least 80 times greater, at least 90 times greater, or at least 100 times greater, than its affinity for a different molecule. In some embodiments, a binding moiety that specifically binds a particular target molecule binds a different molecule at such a low affinity that binding cannot be detected using an assay described herein or otherwise known in the art. In some embodiments, "specifically binds" means, for instance, that a binding moiety binds a molecule target with a $K_D$ of about 0.1 mM or less. In some embodiments, "specifically binds" means that a polypeptide or molecule binds a target with a $K_D$ of at about 10 μM or less or about 1 μM or less. In some embodiments, "specifically binds" means that a polypeptide or molecule binds a target with a $K_D$ of at about 0.1 μM or less, about 0.01 μM or less, or about 1 nM or less. Because of the sequence identity between homologous proteins in different species, specific binding can include a polypeptide or molecule that recognizes a protein or target in more than one species. Likewise, because of homology within certain regions of polypeptide sequences of different proteins, specific binding can include a polypeptide or molecule that recognizes more than one protein or target. It is understood that, in some embodiments, a binding moiety (e.g., antibody) that specifically binds a first target may or may not specifically bind a second target. As such, "specific binding" does not necessarily require (although it can include) exclusive binding, i.e., binding to a single target. Thus, a binding moiety (e.g., antibody) can, in some embodiments, specifically bind more than one target. For example, an antibody can, in certain instances, comprise two identical antigen-binding sites, each of which specifically binds the same epitope on two or more proteins. In certain alternative embodiments, an antibody can be bispecific and comprise at least two antigen-binding sites with differing specificities.

The term "binding affinity" as used herein generally refers to the strength of the sum total of noncovalent interactions between a binding moiety and a target molecule (e.g., antigen). The binding of a binding moiety and a target molecule is a reversible process, and the affinity of the binding is typically reported as an equilibrium dissociation constant ($K_D$). $K_D$ is the ratio of a dissociation rate ($k_{off}$ or $k_d$) to the association rate ($k_{on}$ or $k_a$). The lower the $K_D$ of a binding pair, the higher the affinity. A variety of methods of measuring binding affinity are known in the art, any of which can be used for purposes of the present disclosure. Specific illustrative embodiments include the following. In some embodiments, the "$K_D$" or "$K_D$ value" can be measured by assays known in the art, for example by a binding assay. The $K_D$ may be measured in a radiolabeled antigen binding assay (RIA) (Chen, et al., (1999) *J. Mol Biol* 293:865-881). The $K_D$ or $K_D$ value may also be measured by using surface plasmon resonance assays by Biacore, using, for example, a BIAcore™-2000 or a BIAcore™-3000 BIAcore, Inc., Piscataway, NJ), or by biolayer interferometry using, for example, the OctetQK384 system (ForteBio, Menlo Park, CA).

The term "variant" as used herein in relation to a protein or a polypeptide with particular sequence features (the "reference protein" or "reference polypeptide") refers to a different protein or polypeptide having one or more (such as, for example, about 1 to about 25, about 1 to about 20, about 1 to about 15, about 1 to about 10, or about 1 to about 5) amino acid substitutions, deletions, and/or additions as compared to the reference protein or reference polypeptide. The changes to an amino acid sequence can be amino acid substitutions. The changes to an amino acid sequence can be conservative amino acid substitutions. A functional fragment or a functional variant of a protein or polypeptide maintains the basic structural and functional properties of the reference protein or polypeptide.

The terms "polypeptide," "peptide," "protein," and their grammatical equivalents as used interchangeably herein refer to polymers of amino acids of any length, which can be linear or branched. It can include unnatural or modified amino acids or be interrupted by non-amino acids. A polypeptide, peptide, or protein can also be modified with, for example, disulfide bond formation, glycosylation, lipidation, acetylation, phosphorylation, or any other manipulation or modification.

The terms "polynucleotide," "nucleic acid," and their grammatical equivalents as used interchangeably herein mean polymers of nucleotides of any length and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical," percent "identity," and their grammatical equivalents as used herein in the context of two or more polynucleotides or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, Megalign, BestFit, GCG Wisconsin Package, and variants thereof. In some embodiments, two polynucleotides or polypeptides provided herein are substantially identical, meaning they have at least 70%, at least 75%, at least 80%, at least 85%, at least 90%, and in some embodiments at least 95%, at least 96%, at least 97%, at least 98%, or at least 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-1000 bases or more, and in some embodiments the sequences are substantially identical over the full length of the sequences being compared, such as a nucleotide sequence encoding a protein of interest.

The term "vector," and its grammatical equivalents as used herein refer to a vehicle that is used to carry genetic material (e.g., a polynucleotide sequence), which can be introduced into a host cell, where it can be replicated and/or expressed. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more polynucleotides are to be co-expressed, both polynucleotides can be inserted, for example, into a single expression vector or in separate expression vectors. For single vector expression, the encoding polynucleotides can be operationally linked to one common expression control sequence or linked to different expression control sequences, such as one inducible promoter and one constitutive promoter. The introduction of polynucleotides into a host cell can be confirmed using methods well known in the art. It is understood by those skilled in the art that the polynucleotides are expressed in a sufficient amount to produce a desired product (e.g., an anti-mesothelin antibody or antigen-binding fragment as described herein), and it is further understood that expression levels can be optimized to obtain sufficient expression using methods well known in the art.

The term "chimeric antigen receptor" or "CAR" as used herein refers to an artificially constructed hybrid protein or polypeptide containing a binding moiety (e.g., an antibody) linked to immune cell (e.g., T cell) signaling or activation domains. In some embodiments, CARs are synthetic receptors that retarget T cells to tumor surface antigens (Sadelain et al., *Nat. Rev. Cancer* 3(1):35-45 (2003); Sadelain et al., *Cancer Discovery* 3(4):388-398 (2013)). CARs can provide both antigen binding and immune cell activation functions onto an immune cell such as a T cell. CARs have the ability to redirect T-cell specificity and reactivity toward a selected target in a non-MHC-restricted manner, exploiting the antigen-binding properties of monoclonal antibodies. The non-MHC-restricted antigen recognition can give T-cells expressing CARs the ability to recognize an antigen independent of antigen processing, thus bypassing a mechanism of tumor escape.

The term "genetic engineering" or its grammatical equivalents when used in reference to a cell is intended to mean alteration of the genetic materials of the cell that is not normally found in a naturally occurring cell. Genetic alterations include, for example, modifications introducing expressible polynucleotides, other additions, mutations/alterations, deletions and/or other functional disruption of the cell's genes. Such modifications can be done in, for example, coding regions and functional fragments thereof of a gene. Additional modifications can be done in, for example, non-coding regulatory regions in which the modifications alter expression of a gene.

The term "transfer," "transduce," "transfect," and their grammatical equivalents as used herein refer to a process by which an exogenous polynucleotide is introduced into the host cell. A "transferred," "transfected," or "transduced" cell is one which has been transferred, transduced, or transfected with an exogenous polynucleotide. The cell includes the primary subject cell and its progeny. A polynucleotide can be "transferred" into a host cell using any type of approaches known in the art, including, e.g., a chemical method, a physical method, or a biological method. A polynucleotide is commonly "transduced" into a host cell using a virus. By contrast, a polynucleotide is commonly "transfected" into a host cell using a non-viral approach. These terms are used interchangeable at times, and a person of ordinary skill in the art would readily understand their meanings in different contexts.

As used herein, the term "encode" and its grammatical equivalents refer to the inherent property of specific sequences of nucleotides in a polynucleotide or a nucleic acid, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein. Unless otherwise specified, a "nucleotide sequence encoding an amino acid sequence" includes all nucleotide sequences that are degenerate versions of each other and that encode the same amino acid sequence. Nucleotide sequences that encode proteins and RNA can include introns.

A polypeptide, peptide, protein, antibody, polynucleotide, vector, cell, or composition which is "isolated" is a polypeptide, peptide, protein, antibody, polynucleotide, vector, cell, or composition which is in a form not found in nature. Isolated polypeptides, peptides, proteins, antibodies, polynucleotides, vectors, cells, or compositions include those which have been purified to a degree that they are no longer in a form in which they are found in nature. In some embodiments, a polypeptide, peptide, protein, antibody, polynucleotide, vector, cell, or composition which is isolated is substantially pure.

The term "immune effector cell" and its grammatical equivalents as used herein and understood in the art refer to cells that are of hematopoietic origin and play a direct role in the immune response against a target, such as a pathogen, a cancer cell, or a foreign substance. Immune effector cells include T cells, B cell, natural killer (NK) cells, NKT cells, macrophages, granulocytes, neutrophils, eosinophils, mast cells, and basophils.

The term "treat" and its grammatical equivalents as used herein in connection with a disease or a condition, or a subject having a disease or a condition refer to an action that suppresses, eliminates, reduces, and/or ameliorates a symptom, the severity of the symptom, and/or the frequency of the symptom associated with the disease or disorder being treated. For example, when used in reference to a cancer or tumor, the term "treat" and its grammatical equivalents refer to an action that reduces the severity of the cancer or tumor, or retards or slows the progression of the cancer or tumor, including (a) inhibiting the growth, or arresting development of the cancer or tumor, (b) causing regression of the cancer or tumor, or (c) delaying, ameliorating or minimizing one or more symptoms associated with the presence of the cancer or tumor.

The term "administer" and its grammatical equivalents as used herein refer to the act of delivering, or causing to be delivered, a therapeutic or a pharmaceutical composition to the body of a subject by a method described herein or otherwise known in the art. The therapeutic can be a compound, a polypeptide, an antibody, a cell, or a population of cells. Administering a therapeutic or a pharmaceutical composition includes prescribing a therapeutic or a pharmaceutical composition to be delivered into the body of a subject. Exemplary forms of administration include oral dosage forms, such as tablets, capsules, syrups, suspensions; injectable dosage forms, such as intravenous (IV), intramuscular (IM), or intraperitoneal (IP); transdermal dosage forms, including creams, jellies, powders, or patches; buccal dosage forms; inhalation powders, sprays, suspensions, and rectal suppositories.

The terms "effective amount," "therapeutically effective amount," and their grammatical equivalents as used herein refer to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to the subject. The therapeutically effective amount can be ascertained by measuring relevant physiological effects. The exact amount required vary from subject to subject, depending on the age, weight, and general condition of the subject, the severity of the condition being treated, the judgment of the clinician, and the like. An appropriate "effective amount" in any individual case can be determined by one of ordinary skill in the art using routine experimentation.

The term "pharmaceutically acceptable carrier" or "pharmaceutically acceptable excipient" refers to a material that is suitable for drug administration to an individual along with an active agent without causing undesirable biological effects or interacting in a deleterious manner with any of the other components of the pharmaceutical composition.

The term "subject" as used herein refers to any animal (e.g., a mammal), including, but not limited to, humans, non-human primates, canines, felines, rodents, and the like, which is to be the recipient of a particular treatment. A subject can be a human. A subject can have a particular disease or condition.

The term "autologous" as used herein refers to any material derived from the same individual to which it is later to be re-introduced into the individual.

The term "allogeneic" as used herein refers to a graft derived from a different animal of the same species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Exemplary genes and polypeptides are described herein with reference to GenBank numbers, GI numbers and/or SEQ ID NOs. It is understood that one skilled in the art can readily identify homologous sequences by reference to sequence sources, including but not limited to GenBank (ncbi.nlm.nih.gov/genbank/) and EMBL (embl.org/).

5.2 Anti-Mesothelin Antibodies and Antigen-Binding Fragments

Provided herein are antibodies or antigen-binding fragments thereof that specifically bind mesothelin (e.g., human mesothelin). In some embodiments, provided herein are anti-mesothelin antibodies. In some embodiments, the antibody is an IgA, IgD, IgE, IgG, or IgM antibody. In some embodiments, the antibody is an IgA antibody. In some embodiments, the antibody is an IgD antibody. In some embodiments, the antibody is an IgE antibody. In some embodiments, the antibody is an IgG antibody. In some embodiments, the antibody is an IgM antibody. In some embodiments, the antibodies provided herein can be an IgG1 antibody, an IgG2 antibody, an IgG3 antibody, or an IgG4 antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody.

In some embodiments, provided herein are antigen-binding fragments of an anti-mesothelin antibody. In some embodiments, antigen-binding fragments provided herein can be a single domain antibody (sdAb), a heavy chain antibody (HCAb), a Fab, a Fab', a F(ab')$_2$, a Fv, a single-chain variable fragment (scFv), or a (scFv)$_2$. In some embodiments, the antigen-binding fragment of an anti-mesothelin antibody is a single domain antibody (sdAb). In some embodiments, the antigen-binding fragment of an anti-mesothelin antibody is a heavy chain antibody (HCAb). In some embodiments, the antigen-binding fragment of an anti-mesothelin antibody is a Fab. In some embodiments, the antigen-binding fragment of an anti-mesothelin antibody is a Fab'. In some embodiments, the antigen-binding fragment of an anti-mesothelin antibody is a F(ab')$_2$. In some embodiments, the antigen-binding fragment of an anti-mesothelin antibody is a Fv. In some embodiments, the antigen-binding fragment of an anti-mesothelin antibody is a scFv. In some embodiments, the antigen-binding fragment of an anti-mesothelin antibody is a disulfide-linked scFv [(scFv)$_2$]. In some embodiments, the antigen-binding fragment of an anti-mesothelin antibody is a diabody (dAb).

In some embodiments, the anti-mesothelin antibodies or antigen-binding fragments provided herein comprise recombinant antibodies or antigen-binding fragments. In some embodiments, the anti-mesothelin antibodies or antigen-binding fragments provided herein comprise monoclonal antibodies or antigen-binding fragments. In some embodiments, the anti-mesothelin antibodies or antigen-binding fragments provided herein comprise polyclonal antibodies or antigen-binding fragments. In some embodiments, the anti-mesothelin antibodies or antigen-binding fragments provided herein comprise camelid (e.g., camels, dromedary and llamas) antibodies or antigen-binding fragments. In some embodiments, the anti-mesothelin antibodies or antigen-binding fragments provided herein comprise chimeric antibodies or antigen-binding fragments. In some embodiments, the anti-mesothelin antibodies or antigen-binding fragments provided herein comprise humanized antibodies or antigen-binding fragments. In some embodiments, the anti-mesothelin antibodies or antigen-binding fragments provided herein comprise human antibodies or antigen-binding fragments. In some embodiments, provided herein are anti-mesothelin human scFvs.

In some embodiments, the anti-mesothelin antibodies or antigen-binding fragments provided herein are isolated. In some embodiments, the anti-mesothelin antibodies or antigen-binding fragments provided herein are substantially pure.

In some embodiments, the anti-mesothelin antibody or antigen-binding fragment provided herein comprises a multispecific antibody or antigen-binding fragment. In some embodiments, the anti-mesothelin antibody or antigen-binding fragment provided herein comprises a bispecific antibody or antigen-binding fragment. In some embodiments, provided herein is a Bi-specific T-cell engager (BiTE). BiTEs are bispecific antibodies that bind to a T cell antigen (e.g., CD3) and a tumor antigen. BiTEs have been shown to induce directed lysis of target tumor cells and thus provide great potential therapies for cancers and other disorders. In some embodiments, provided herein are BiTEs that specifically bind CD3 and mesothelin. In some embodiments, the BiTEs comprises an anti-mesothelin antibody or antigen-binding fragment provided herein. In some embodiments, the BiTEs comprises an anti-mesothelin scFv provided herein.

In some embodiments, the anti-mesothelin antibody or antigen-binding fragment provided herein comprises a monovalent antigen-binding site. In some embodiments, an anti-mesothelin antibody or antigen-binding fragment comprises a monospecific binding site. In some embodiments, an anti-mesothelin antibody or antigen-binding fragment comprises a bivalent binding site.

In some embodiments, an anti-mesothelin antibody or antigen-binding fragment is a monoclonal antibody or antigen-binding fragment. Monoclonal antibodies can be prepared by any method known to those of skill in the art. One exemplary approach is screening protein expression libraries, e.g., phage or ribosome display libraries. Phage display is described, for example, in Ladner et al., U.S. Pat. No. 5,223,409; Smith (1985) *Science* 228:1315-1317; and WO 92/18619. In some embodiments, recombinant monoclonal antibodies are isolated from phage display libraries expressing variable regions or CDRs of a desired species. Screening of phage libraries can be accomplished by various techniques known in the art.

In some embodiments, monoclonal antibodies are prepared using hybridoma methods known to one of skill in the art. For example, using a hybridoma method, a mouse, rat, rabbit, hamster, or other appropriate host animal, is immunized as described above. In some embodiments, lymphocytes are immunized in vitro. In some embodiments, the immunizing antigen is a human protein or a fragment thereof. In some embodiments, the immunizing antigen is a human protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed to a chosen antigen can be identified by a variety of methods including, but not limited to, immunoprecipitation, immunoblotting, and in vitro binding assays (e.g., flow cytometry, FACS, ELISA, SPR (e.g., Biacore), and radioimmunoassay). Once hybridoma cells that produce antibodies of the desired specificity, affinity, and/or activity are identified, the clones may be subcloned by limiting dilution or other techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In some embodiments, a monoclonal antibody is modified by using recombinant DNA technology to generate alternative antibodies. In some embodiments, the constant domains of the light chain and heavy chain of a mouse monoclonal antibody are replaced with the constant regions of a human antibody to generate a chimeric antibody. In some embodiments, the constant regions are truncated or removed to generate a desired antibody fragment of a monoclonal antibody. In some embodiments, site-directed or high-density mutagenesis of the variable region(s) is used to optimize specificity and/or affinity of a monoclonal antibody.

In some embodiments, an anti-mesothelin antibody or antigen-binding fragment is a humanized antibody or antigen-binding fragment. Various methods for generating humanized antibodies are known in the art. Methods are known in the art for achieving high affinity binding with humanized antibodies. A non-limiting example of such a method is hypermutation of the variable region and selection of the cells expressing such high affinity antibodies (affinity maturation). In addition to the use of display libraries, the specified antigen (e.g., recombinant mesothelin or an epitope thereof) can be used to immunize a non-human animal, e.g., a rodent. In certain embodiments, rodent antigen-binding fragments (e.g., mouse antigen-binding fragments) can be generated and isolated using methods known in the art and/or disclosed herein. In some embodiments, a mouse can be immunized with an antigen (e.g., recombinant mesothelin or an epitope thereof).

In some embodiments, an anti-mesothelin antibody or antigen-binding fragment is a human antibody or antigen-binding fragment. Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology can be used to produce human antibodies and antibody fragments in vitro, from immunoglobulin variable region gene repertoires from unimmunized donors. Techniques for the generation and use of antibody phage libraries are well-known in the art. Once antibodies are identified, affinity maturation strategies known in the art, including but not limited to, chain shuffling and site-directed mutagenesis, can be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

The specific CDR sequences defined herein are generally based on a combination of Kabat and Chothia definitions. However, it is understood that reference to a heavy chain CDR or CDRs and/or a light chain CDR or CDRs of a specific antibody encompass all CDR definitions as known to those of skill in the art.

Anti-mesothelin antibodies or antigen-binding fragments provided herein include the followings clones: M12. The sequence features are described below.

In some embodiments, anti-mesothelin antibodies or antigen-binding fragments provided herein comprise one, two, three, four, five, and/or six CDRs of any one of the antibodies described herein. In some embodiments, anti-mesothelin antibodies or antigen-binding fragments provided herein comprise a VL comprising one, two, and/or three, VL CDRs from Table 1. In some embodiments, anti-mesothelin antibodies or antigen-binding fragments provided herein comprise a VH comprising one, two, and/or three VH CDRs from Table 2. In some embodiments, anti-mesothelin antibodies or antigen-binding fragments provided herein comprise one, two, and/or three VL CDRs from Table 1 and one, two, and/or three VH CDRs from Table 2.

TABLE 1

Amino acid sequences of light chain variable region CDRs (VL CDRs) of anti-mesothelin 12

| Antibody | VL CDR1 | VL CDR2 | VL CDR3 |
|---|---|---|---|
| M12 | RASQGGGNYLA (SEQ ID NO: 1) | GASKLQS (SEQ ID NO: 2) | QQLNSYPVT (SEQ ID NO: 3) |

TABLE 2

Amino acid sequences of heavy chain variable region CDRs (VH CDRs) of anti-mesothelin 12

| Antibody | VH CDR1 | VH CDR2 | VH CDR3 |
|---|---|---|---|
| M12 | TYYIH (SEQ ID NO: 4) | IINPSSGSTTYTQKFQG (SEQ ID NO: 5) | GETLRGYFDY (SEQ ID NO: 6) |

In some embodiments, an anti-mesothelin antibody or antigen-binding fragment thereof comprises a humanized antibody or antigen-binding fragment. In some embodiments, an anti-mesothelin antibody or antigen-binding fragment thereof comprises a VL CDR1, VL CDR2, VL CDR3, VH CDR1, VH CDR2, and/or VH CDR3 from an antibody or antigen-binding fragment described herein. In some embodiments, an anti-mesothelin antibody or antigen-binding fragment thereof comprises a variant of an anti-mesothelin antibody or antigen-binding fragment described herein. In some embodiments, a variant of an anti-mesothelin antibody or antigen-binding fragment comprises one to 30 amino acid substitutions, additions, and/or deletions in the anti-mesothelin antibody or antigen-binding fragment. In some embodiments, a variant of an anti-mesothelin antibody or antigen-binding fragment comprises one to 25 amino acid substitutions, additions, and/or deletions in the anti-mesothelin antibody or antigen-binding fragment. In some embodiments, a variant of an anti-mesothelin antibody or antigen-binding fragment comprises one to 20 substitutions, additions, and/or deletions in the anti-mesothelin antibody or antigen-binding fragment. In some embodiments, a variant of an anti-mesothelin antibody or antigen-binding fragment comprises one to 15 substitutions, additions, and/or deletions in the anti-mesothelin antibody or antigen-binding fragment. In some embodiments, a variant of an anti-mesothelin antibody or antigen-binding fragment comprises one to 10 substitutions, additions, and/or deletions in the anti-mesothelin antibody or antigen-binding fragment. In some embodiments, a variant of an anti-mesothelin antibody or antigen-binding fragment comprises one to five conservative amino acid substitutions, additions, and/or deletions in the anti-mesothelin antibody or antigen-binding fragment. In some embodiments, a variant of an anti-mesothelin antibody or antigen-binding fragment comprises one to three amino acid substitutions, additions, and/or deletions in the anti-mesothelin antibody or antigen-binding fragment. In some embodiments, the amino acid substitutions, additions, and/or deletions are conservative amino acid substitutions. In some embodiments, the conservative amino acid substitution(s) is in a CDR of the antibody or antigen-binding fragment. In some embodiments, the conservative amino acid substitution(s) is not in a CDR of the antibody or antigen-binding fragment. In some embodiments, the conservative amino acid substitution(s) is in a framework region of the antibody or antigen-binding fragment.

In some embodiments, provided herein are antibodies or antigen-binding fragments thereof that specifically bind mesothelin (e.g., human mesothelin), comprising a light chain variable region (VL) comprising (1) a light chain CDR1 (VL CDR1) having an amino acid sequence of SEQ ID NO: 1; (2) a light chain CDR2 (VL CDR2) having an amino acid sequence of SEQ ID NO: 2; or (3) a light chain CDR3 (VL CDR3) having an amino acid sequence of SEQ ID NO: 3; or a variant thereof having up to about 3, about 5, about 8, about 10, about 12, or about 15 amino acid substitutions, additions, and/or deletions in the VL CDRs. In some embodiments, the variant has about 5 amino acid substitutions, additions, and/or deletions in the VL CDRs.

In some embodiments, provided herein are antibodies or antigen-binding fragments thereof that specifically bind mesothelin (e.g., human mesothelin), comprising a VL comprising (1) a VL CDR1 having an amino acid sequence of SEQ ID NO: 1; (2) a VL CDR2 having an amino acid sequence of SEQ ID NO: 2; and (3) a VL CDR3 having an amino acid sequence of SEQ ID NO: 3; or a variant thereof having up to about 3, about 5, about 8, about 10, about 12, or about 15 amino acid substitutions, additions, and/or deletions in the VL CDRs. In some embodiments, the variant has up to about 5 amino acid substitutions, additions, and/or deletions in the VL CDRs.

In some embodiments, provided herein are antibodies or antigen-binding fragments thereof that specifically bind mesothelin (e.g., human mesothelin) comprising a heavy chain variable region (VH) comprising (1) a heavy chain CDR1 (VH CDR1) having an amino acid sequence of SEQ ID NO: 4; (2) a heavy chain CDR2 (VH CDR2) having an amino acid sequence of SEQ ID NO: 5; or (3) a heavy chain CDR3 (VH CDR3) having an amino acid sequence of SEQ ID NO: 6; or a variant thereof having up to about 3, about 5, about 8, about 10, about 12, or about 15 amino acid substitutions, additions, and/or deletions in the VH CDRs. In some embodiments, the variant has up about 5 amino acid substitutions, additions, and/or deletions in the VH CDRs.

In some embodiments, provided herein are antibodies or antigen-binding fragments thereof that specifically bind mesothelin (e.g., human mesothelin) comprising a VH comprising (1) a VH CDR1 having an amino acid sequence of SEQ ID NO: 4; (2) a VH CDR2 having an amino acid sequence of SEQ ID NO: 5; and (3) a VH CDR3 having an amino acid sequence of SEQ ID NO: 6; or a variant thereof having up to about 3, about 5, about 8, about 10, about 12, or about 15 amino acid substitutions, additions, and/or deletions in the VH CDRs. In some embodiments, the variant has up about 5 amino acid substitutions, additions, and/or deletions in the VH CDRs.

In some embodiments, provided herein are antibodies or antigen-binding fragments thereof that specifically bind mesothelin (e.g., human mesothelin), comprising (a) a VL comprising (1) a VL CDR1 having an amino acid sequence of SEQ ID NO: 1; (2) a VL CDR2 having an amino acid sequence of SEQ ID NO: 2; and (3) a VL CDR3 having an amino acid sequence of SEQ ID NO: 3; or a variant thereof having up to about 5 amino acid substitutions, additions, and/or deletions in the VL CDRs; and (b) a VH comprising (1) a VH CDR1 having an amino acid sequence of SEQ ID NO: 4; (2) a VH CDR2 having an amino acid sequence of SEQ ID NO: 5; and (3) a VH CDR3 having an amino acid sequence of SEQ ID NO: 6; or a variant thereof having up to about 5 amino acid substitutions, additions, and/or deletions in the VH CDRs.

In some embodiments, provided herein are antibodies or antigen-binding fragments thereof that specifically bind mesothelin (e.g., human mesothelin) having a VL, wherein the VL comprises VL CDR1, CDR2 and CDR3 having the amino acid sequences of SEQ ID NOs: 1, 2, and 3, respectively, or a variant thereof having up to about 3, about 5, about 8, about 10, about 12, or about 15 amino acid substitutions, additions, and/or deletions in the VL CDRs. In some embodiments, the variant has up about 5 amino acid substitutions, additions, and/or deletions in the VL CDRs.

In some embodiments, provided herein are antibodies or antigen-binding fragments thereof that specifically bind mesothelin (e.g., human mesothelin) having a VH, wherein the VH comprises VH CDR1, CDR2 and CDR3 having the amino acid sequences of SEQ ID NOs: 4, 5, and 6, respectively, or a variant thereof having up to about 3, about 5, about 8, about 10, about 12, or about 15 amino acid substitutions, additions, and/or deletions in the VH CDRs. In some embodiments, the variant has up about 5 amino acid substitutions, additions, and/or deletions in the VH CDRs.

In some embodiments, provided herein are antibodies or antigen-binding fragments thereof that specifically bind mesothelin (e.g., human mesothelin) having a VL and a VH. In some embodiments, the VL and VH are connected by a linker. The linker can be a flexible linker or a rigid linker. In some embodiments, the linker has the amino acid sequence of (GGGGS)n, n=1, 2, 3, 4, or 5. For example, the linker may have the amino acid sequence of GGGGS (SEQ ID NO: 14). In some embodiments, the linker has the amino acid sequence of (EAAAK)n, n=1, 2, 3, 4, or 5. For example, the linker may have the amino acid sequence of EAAAK (SEQ ID NO: 15). In some embodiments, the linker has the amino acid sequence of (PA)nP, n=1, 2, 3, 4, or 5. For example, the linker may have the amino acid sequence of PAP (SEQ ID NO: 16). In some embodiments, the linker has the amino acid sequence of GGGGSGGGGSGGGGS (SEQ ID NO: 17).

In some embodiments, provided herein are antibodies or antigen-binding fragments thereof that specifically bind mesothelin (e.g., human mesothelin) having a VL and a VH, wherein (a) the VL comprises VL CDR1, CDR2 and CDR3 having the amino acid sequences of SEQ ID NOs: 1, 2, and 3, respectively, or a variant thereof having up to about 5 amino acid substitutions, additions, and/or deletions in the VL CDRs; and (b) the VH comprises VH CDR1, CDR2 and CDR3 having the amino acid sequences of SEQ ID NOs: 4, 5, and 6, respectively, or a variant thereof having up to about 5 amino acid substitutions, additions, and/or deletions in the VH CDRs.

In some embodiments, provided herein are antibodies or antigen-binding fragments thereof that specifically bind mesothelin (e.g., human mesothelin) having a VL and a VH, wherein the VL comprises VL CDR1, CDR2 and CDR3 and the VH comprises VH CDR1, CDR2 and CDR3, and wherein the VL CDR1, VL CDR2, VL CDR3, VH CDR1, VH CDR2 and VH CDR3 have the amino acid sequences of SEQ ID NOs: 1, 2, 3, 4, 5, and 6, respectively, or a variant thereof having up to about 5 amino acid substitutions, additions, and/or deletions in the CDRs.

In some embodiments, provided herein are antibodies or antigen-binding fragments thereof that specifically bind mesothelin (e.g., human mesothelin) having a VL, comprising (1) a VL CDR1 having the amino acid sequence of SEQ ID NO: 1, (2) a VL CDR2 having the amino acid sequence of SEQ ID NO: 2, or (3) a VL CDR3 having the amino acid sequence of SEQ ID NO: 3. The VL can have VL CDR1, VL CDR2, and VL CDR3 having the amino acid sequences of SEQ ID NOs: 1, 2, and 3, respectively. In some embodiments, provided herein are antibodies or antigen-binding fragments thereof that specifically bind mesothelin (e.g., human mesothelin) having a VH, comprising (1) a VH CDR1 having the amino acid sequence of SEQ ID NO: 4, (2) a VH CDR2 having the amino acid sequence of SEQ ID NO: 5, or (3) a VH CDR3 having the amino acid sequence of SEQ ID NO: 6. The VH can have VH CDR1, VH CDR2, and VH CDR3 having the amino acid sequences of SEQ ID NOs: 4, 5, and 6, respectively. In some embodiments, provided herein are antibodies or antigen-binding fragments thereof that specifically bind mesothelin (e.g., human mesothelin) comprising (a) a VL that comprises VL CDR1, VL CDR2, and VL CDR3 having the amino acid sequences of SEQ ID NOs: 1, 2, and 3, respectively; and (b) a VH that comprises VH CDR1, VH CDR2, and VH CDR3 having the amino acid sequences of SEQ ID NOs: 4, 5, and 6 respectively.

In some embodiments, provided herein are antibodies or antigen-binding fragments thereof that specifically bind mesothelin (e.g., human mesothelin) comprising a VL having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to an amino acid sequence of SEQ ID NO: 7. In some embodiments, provided herein are antibodies or antigen-binding fragments thereof that specifically bind mesothelin (e.g., human mesothelin) comprising a VH having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to an amino acid sequence of SEQ ID NO: 8.

TABLE 3

Amino acid sequences of light chain variable regions (VL) and heavy chain variable region (VH) of anti-mesothelin 12 antibodie

| Antibody | VL | VH |
|---|---|---|
| M12 | AIRLTQSPSLLSASVGDRVTVTCR ASQGGGNYLAWYQQKPGKAPKL LIYGASKLQSGVPSRFSGSGSGTE FTLTISSLQPEDFATYYCQQLNSY PVTFGQGTKVDIK (SEQ ID NO: 7) | EVQLVESGAEVKKPGASVKVSCK ASGYTFTTYYIHWVRQAPGQGLE WMGIINPSSGSTTYTQKFQGRVT MTRDTSTSTVYIELSGLRSEDTAV YYCARGETLRGYFDYWGQGTLV TVSS (SEQ ID NO: 8) |

In some embodiments, provided herein are antibodies or antigen-binding fragments thereof that specifically bind mesothelin (e.g., human mesothelin) comprising: (a) a VL having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity sequence identity to an amino acid sequence of SEQ ID NO: 7; and (b) a VH having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity sequence identity to an amino acid sequence of SEQ ID NO: 8.

In some embodiments, provided herein are antibodies or antigen-binding fragments thereof that specifically bind mesothelin (e.g., human mesothelin) comprising a VL, wherein the VL has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 7. In some embodiments, the anti-mesothelin antibody or antigen-binding fragment thereof has a VL having at least 85% sequence identity to SEQ ID NO: 7. In some embodiments, the anti-mesothelin antibody or antigen-binding fragment thereof has a VL having at least 90% sequence identity to SEQ ID NO: 7. In some embodiments, the anti-mesothelin antibody or antigen-binding fragment thereof has a VL having at least 95% sequence identity to SEQ ID NO: 7. In some embodiments, the anti-mesothelin antibody or antigen-binding fragment thereof has a VL having at least 98% sequence identity to SEQ ID NO: 7. In some embodiments, provided herein are antibodies or antigen-binding fragments thereof that specifically bind mesothelin (e.g., human mesothelin) comprising a VL having the amino acid sequence of SEQ ID NO: 7.

In some embodiments, provided herein are antibodies or antigen-binding fragments thereof that specifically bind mesothelin (e.g., human mesothelin) comprising a VH, wherein the VH has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 8. In some embodiments, the anti-mesothelin antibody or antigen-binding fragment thereof has a VH having at least 85% sequence identity to SEQ ID NO: 8. In some embodiments, the anti-mesothelin antibody or antigen-binding fragment thereof has a VH having at least 90% sequence identity to SEQ ID NO: 8. In some embodiments, the anti-mesothelin antibody or antigen-binding fragment thereof has a VH having at least 95% sequence identity to SEQ ID NO: 8. In some embodiments, the anti-mesothelin antibody or antigen-binding fragment thereof has a VH having at least 98% sequence identity to SEQ ID NO: 8. In some embodiments, provided herein are antibodies or antigen-binding fragments thereof that specifically bind mesothelin (e.g., human mesothelin) comprising a VH having the amino acid sequence of SEQ ID NO: 8.

The anti-mesothelin antibodies or antigen-binding fragments thereof can comprise a combination of any VL disclosed herein and any VH disclosed herein. In some embodiments, the VL and VH are connected by a linker. The linker can be a flexible linker or a rigid linker. In some embodiments, the linker has the amino acid sequence of (GGGGS)n, n=1, 2, 3, 4, or 5. For example, the linker may have the amino acid sequence of GGGGS (SEQ ID NO: 14). In some embodiments, the linker has the amino acid sequence of (EAAAK)n, n=1, 2, 3, 4, or 5. For example, the linker may have the amino acid sequence of EAAAK (SEQ ID NO: 15). In some embodiments, the linker has the amino acid sequence of (PA)nP, n=1, 2, 3, 4, or 5. For example, the linker may have the amino acid sequence of PAP (SEQ ID NO: 16). In some embodiments, the linker has the amino acid sequence of GGGGSGGGGSGGGGS (SEQ ID NO: 17).

In some embodiments, provided herein are antibodies or antigen-binding fragments thereof that specifically bind mesothelin (e.g., human mesothelin) comprising a VL and a VH, wherein the VL and VH have the amino acid sequences of SEQ ID NOs: 7 and 8 respectively.

In some embodiments, provided herein are antibodies or antigen-binding fragments thereof that specifically bind mesothelin (e.g., human mesothelin) comprising (a) a VL comprising VL CDRs 1, 2, and 3 from a VL having an amino acid sequence of SEQ ID NOs: 7; and/or (b) a VH comprising VH CDRs 1, 2, and 3 from a VH having an amino acid sequence of SEQ ID NOs: 8.

In some embodiments, provided herein are antibodies or antigen-binding fragments thereof that specifically bind mesothelin (e.g., human mesothelin) comprising a VL, wherein the VL comprises VL CDRs 1, 2, and 3 from a VL having the amino acid sequence of SEQ ID NO: 7.

In some embodiments, provided herein are antibodies or antigen-binding fragments thereof that specifically bind mesothelin (e.g., human mesothelin) comprising a VH, wherein the VH comprises VH CDRs 1, 2, and 3 from a VH having the amino acid sequence of SEQ ID NO: 8.

In some embodiments, provided herein are antibodies or antigen-binding fragments thereof that specifically bind mesothelin (e.g., human mesothelin) comprising a VL and a VH, wherein the VL comprises VL CDR1, CDR2, and CDR3 from a VL having the amino acid sequence of SEQ ID NO: 7, and the VH comprises VH CDR1, CDR2, and CDR3 from a VH having the amino acid sequence of SEQ ID NO: 8.

In some embodiments, the anti-mesothelin antibody or antigen-binding fragment thereof provided herein is the scFv designated as M12 (SEQ ID NO: 11). In some embodiments, the anti-mesothelin antibody or antigen-binding fragment thereof provided herein has an amino acid sequence that is at least about 80%, about 85%, about 90%, about 91%, about 92%, about 93%, about 94%, about 95%, about 96%, about 97%, about 98%, or about 99% identical to SEQ ID NO: 11. In some embodiments, the anti-mesothelin antibody or antigen-binding fragment thereof provided herein has a VL from M12 (SEQ ID NO: 7). In some embodiments, the anti-mesothelin antibody or antigen-binding fragment thereof provided herein has a VH from M12 (SEQ ID NO: 8). The anti-mesothelin antibody or antigen-binding fragment thereof provided herein can have both a VL and a VH from M12. In some embodiments, the anti-mesothelin antibody or antigen-binding fragment thereof provided herein has a VL that comprises VL CDRs 1, 2, and 3 from the VL from M12 (SEQ ID NO: 7). In some embodiments, the anti-mesothelin antibody or antigen-binding fragment thereof provided herein has a VH that comprises VH CDRs 1, 2, and 3 from the VH from M12 (SEQ ID NO: 8). The anti-mesothelin antibody or antigen-binding fragment thereof provided herein can have a VL comprising VL CDRs 1, 2, and 3 and a VH comprising VH CDRs 1, 2, and 3 from the VL and VH of M12, respectively. In some embodiments, the anti-mesothelin antibody or antigen-binding fragment thereof provided herein is a variant of M12. The M12 variant can have a VL that is a variant of the VL of M12 having up to about 5 amino acid substitutions, additions, and/or deletions in SEQ ID NO: 7. The M12 variant can have a VH that is a variant of the VH of M12 having up to about 5 amino acid substitutions, additions, and/or deletions in SEQ ID NO: 8. The amino acid substitutions, additions, and/or deletions can be in the VH CDRs or VL CDRs. In some embodiments, the amino acid substitutions, additions, and/or deletions are not in the CDRs. In some embodiments, the variant of M12 has up to about 5 conservative amino acid substitutions. In some embodiments, the variant of M12 has up to 3 conservative amino acid substitutions.

In some embodiments, provided herein are also antibodies or antigen-binding fragments that compete with the antibody or antigen-binding fragment provided above for binding to mesothelin (e.g., human mesothelin). Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments, e.g., BIACORE® surface plasmon resonance (SPR) analysis. In some embodiments, an anti-mesothelin antibody or antigen-binding fragment competes with, and inhibits binding of another antibody or antigen-binding fragment to mesothelin by at least 50%, 60%, 70%, 80%, 90% or 100%. Competition assays can be conducted as described, for example, in Ed Harlow and David Lane, Cold Spring Harb Protoc; 2006; doi: 10.H01/pdb.prot4277 or in Chapter 11 of "Using Antibodies" by Ed Harlow and David Lane, Cold Spring Harbor Laboratory Press, Cold Spring Harbor, NY, USA 1999.

In some embodiments, provided herein are antibodies or antigen-binding fragments that compete with M12 for binding to mesothelin.

The present disclosure further contemplates additional variants and equivalents that are substantially homologous to the recombinant, monoclonal, chimeric, humanized, and human antibodies, or antibody fragments thereof, described herein. In some embodiments, it is desirable to improve the binding affinity of the antibody. In some embodiments, it is desirable to modulate biological properties of the antibody, including but not limited to, specificity, thermostability, expression level, effector function(s), glycosylation, immunogenicity, and/or solubility. Those skilled in the art will appreciate that amino acid changes may alter post-translational processes of an antibody, such as changing the number or position of glycosylation sites or altering membrane anchoring characteristics.

Variations can be a substitution, deletion, or insertion of one or more nucleotides encoding the antibody or polypeptide that results in a change in the amino acid sequence as compared with the native antibody or polypeptide sequence. In some embodiments, amino acid substitutions are the result of replacing one amino acid with another amino acid having similar structural and/or chemical properties, such as the replacement of a leucine with a serine, e.g., conservative amino acid replacements. Insertions or deletions can be in the range of about 1 to 5 amino acids. In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. In some embodiments, variations in the amino acid sequence that are biologically useful and/or relevant can be determined by systematically making insertions, deletions, or substitutions in the sequence and testing the resulting variant proteins for activity as compared to the parent protein.

It is known in the art that the constant region(s) of an antibody mediates several effector functions and these effector functions can vary depending on the isotype of the antibody. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production. In some embodiments, anti-mesothelin antibody or antigen-binding fragment described herein comprise at least one constant region of a human IgA antibody. In some embodiments, anti-mesothelin antibody or antigen-binding fragment described herein comprise at least one constant region of a human IgD antibody. In some embodiments, anti-mesothelin antibody or antigen-binding fragment described herein comprise at least one constant region of a human IgE antibody. In some embodiments, anti-mesothelin antibody or antigen-binding fragment described herein comprise at least one constant region of a human IgG antibody. In some embodiments, anti-mesothelin antibody or antigen-binding fragment described herein comprise at least one constant region of a human IgM antibody. In some embodiments, anti-mesothelin antibody or antigen-binding fragment described herein comprise at least one constant region of a human IgG1 antibody. In some embodiments, anti-mesothelin antibody or antigen-binding fragment described herein comprise at least one constant region of a human IgG2 antibody. In some embodiments, anti-mesothelin antibody or antigen-binding fragment described herein comprise at least one constant region of a human IgG3 antibody. In some embodiments, anti-mesothelin antibody or antigen-binding fragment described herein comprise at least one constant region of a human IgG4 antibody.

In some embodiments, at least one or more of the constant regions has been modified or deleted in the anti-mesothelin antibody or antigen-binding fragment described herein. In some embodiments, the antibodies comprise modifications to one or more of the three heavy chain constant regions (CH1, CH2 or CH3) and/or to the light chain constant region (CL). In some embodiments, the heavy chain constant region of the modified antibodies comprises at least one human constant region. In some embodiments, the heavy chain constant region of the modified antibodies comprises more than one human constant region. In some embodiments, modifications to the constant region comprise additions, deletions, or substitutions of one or more amino acids in one or more regions. In some embodiments, one or more regions are partially or entirely deleted from the constant regions of the modified antibodies. In some embodiments, the entire CH2 domain has been removed from an antibody (ΔCH2 constructs). In some embodiments, a deleted constant region is replaced by a short amino acid spacer that provides some of the molecular flexibility typically imparted by the absent constant region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

In some embodiments, an anti-mesothelin antibody or antigen-binding fragment comprises a Fc region. In some embodiments, the Fc region is fused via a hinge. The hinge can be an IgG1 hinge, an IgG2 hinge, or an IgG3 hinge. The amino acid sequences of the Fc region of human IgG1, IgG2, IgG3, and IgG4 are known to those of ordinary skill in the art. In some cases, Fc regions with amino acid variations have been identified in native antibodies. In some embodiments, the modified antibodies (e.g., modified Fc region) provide for altered effector functions that, in turn, affect the biological profile of the antibody. For example, in some embodiments, the deletion or inactivation (through point mutations or other means) of a constant region reduces Fc receptor binding of the modified antibody as it circulates. In some embodiments, the constant region modifications reduce the immunogenicity of the antibody. In some embodiments, the constant region modifications increase the serum half-life of the antibody. In some embodiments, the constant region modifications reduce the serum half-life of the antibody. In some embodiments, the constant region modifications decrease or remove ADCC and/or complement dependent cytotoxicity (CDC) of the antibody. In some embodiments, specific amino acid substitutions in a human IgG1 Fc region with corresponding IgG2 or IgG4 residues reduce effector functions (e.g., ADCC and CDC) in the modified antibody. In some embodiments, an antibody does not have one or more effector functions (e.g., "effectorless" antibodies). In some embodiments, the antibody has no ADCC activity and/or no CDC activity. In some embodiments, the antibody does not bind an Fc receptor and/or complement factors. In some embodiments, the antibody has no effector function(s). In some embodiments, the constant region modifications increase or enhance ADCC and/or CDC of the antibody. In some embodiments, the constant region is modified to eliminate disulfide linkages or oligosaccharide moieties. In some embodiments, the constant region is modified to add/substitute one or more amino acids to provide one or more cytotoxin, oligosaccharide, or carbohydrate attachment sites. In some embodiments, an anti-mesothelin antibody or antigen-binding fragment comprises a variant Fc region that is engineered with substitutions at specific amino acid positions as compared to a native Fc region. In some embodiments, an anti-mesothelin antibody or antigen-binding fragment described herein comprises an IgG1 heavy chain constant region that comprises one or more amino acid substitutions selected from the group consisting of K214R, L234A, L235E, G237A, D356E, and L358M, per EU numbering. In some embodiments, the IgG1 heavy chain constant region comprises one or more amino acid substitutions selected from the group consisting of K214R, L234A, L235E, G237A, A330S, P331S, D356E, and L358M, per EU numbering. In some embodiments, the IgG1 heavy chain constant region comprises one or more amino acid substitutions selected from the group consisting of K214R, C226S, C229S, and P238S, per EU numbering. In some embodiments, the IgG1 heavy chain constant region comprises one or more amino acid substitutions selected from the group consisting of K214R, D356E, and L358M, per EU numbering. In some embodiments, the IgG1 heavy chain constant region comprises one or more amino acid substitutions selected from the group consisting of S131C, K133R, G137E, G138S, Q196K, I199T, N203D, K214R, C226S, C229S, and P238S, per EU numbering.

In some embodiments, variants can include addition of amino acid residues at the amino- and/or carboxyl-terminal end of the antibody or polypeptide. The length of additional amino acids residues can range from one residue to a hundred or more residues. In some embodiments, a variant comprises an N-terminal methionyl residue. In some embodiments, the variant comprises an additional polypeptide/protein (e.g., Fc region) to create a fusion protein. In some embodiments, a variant is engineered to be detectable and may comprise a detectable label and/or protein (e.g., a fluorescent tag or an enzyme).

The variant antibodies or antigen-binding fragments described herein can be generated using methods known in the art, including but not limited to, site-directed mutagenesis, alanine scanning mutagenesis, and PCR mutagenesis.

In some embodiments, a variant of an anti-mesothelin antibody or antigen-binding fragment disclosed herein can retain the ability to bind mesothelin to a similar extent, the same extent, or to a higher extent, as the parent antibody or antigen-binding fragment. In some embodiments, the variant can be at least about 80%, about 85%, about 90%, about 91%, about 92%, about 93%, about 94%, about 95%, about 96%, about 97%, about 98%, about 99% or more identical in amino acid sequence to the parent antibody or antigen-binding fragment. In certain embodiments, a variant of an anti-mesothelin antibody or antigen-binding fragment comprises the amino acid sequence of the parent anti-mesothelin antibody or antigen-binding fragment with one or more conservative amino acid substitution. Conservative amino acid substitutions are known in the art and include amino acid substitutions in which one amino acid having certain physical and/or chemical properties is exchanged for another amino acid that has the same or similar chemical or physical properties.

In some embodiments, a variant of an anti-mesothelin antibody or antigen-binding fragment comprises the amino acid sequence of the parent antibody or antigen-binding fragment with one or more non-conservative amino acid substitutions. In some embodiments, a variant of an anti-mesothelin antibody or antigen-binding fragment comprises the amino acid sequence of the parent binding antibody or antigen-binding fragment with one or more non-conservative amino acid substitution, wherein the one or more non-conservative amino acid substitutions do not interfere with or inhibit one or more biological activities of the variant (e.g., mesothelin binding). In certain embodiments, the one or more conservative amino acid substitutions and/or the one or more non-conservative amino acid substitutions can enhance a biological activity of the variant, such that the biological activity of the functional variant is increased as compared to the parent binding moiety.

In some embodiments, the variant can have 1, 2, 3, 4, or 5 amino acid substitutions in the CDRs (e.g., VH CDR1, VH CDR2, VH CDR3, VL CDR1, VL CDR2 and VL CDR3) of the binding moiety.

In some embodiments, anti-mesothelin antibodies or antigen-binding fragments described herein are chemically modified naturally or by intervention. In some embodiments, the anti-mesothelin antibodies or antigen-binding fragments have been chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications can be carried out by known techniques. The anti-mesothelin antibodies or antigen-binding fragments can comprise one or more analogs of an amino acid (including, for example, unnatural amino acids), as well as other modifications known in the art.

In some embodiments, an anti-mesothelin antibody or antigen-binding fragment (e.g., an antibody) binds mesothelin (e.g., human mesothelin) with a dissociation constant ($K_D$) of about 1 μM or less, about 100 nM or less, about 40 nM or less, about 20 nM or less, about 10 nM or less, about 1 nM or less, about 0.1 nM or less, 50 pM or less, 10 pM or less, or 1 pM or less. In some embodiments, an anti-mesothelin antibody or antigen-binding fragment binds mesothelin (e.g., human mesothelin) with a $K_D$ of about 20 nM or less. In some embodiments, an anti-mesothelin antibody or antigen-binding fragment binds mesothelin (e.g., human mesothelin) with a $K_D$ of about 10 nM or less. In some embodiments, an anti-mesothelin antibody or antigen-binding fragment binds mesothelin (e.g., human mesothelin) with a $K_D$ of about 1 nM or less. In some embodiments, an anti-mesothelin antibody or antigen-binding fragment binds mesothelin (e.g., human mesothelin) with a $K_D$ of about 0.5 nM or less. In some embodiments, an anti-mesothelin antibody or antigen-binding fragment binds mesothelin (e.g., human mesothelin) with a $K_D$ of about 0.1 nM or less. In some embodiments, an anti-mesothelin antibody or antigen-binding fragment binds mesothelin (e.g., human mesothelin) with a $K_D$ of about 50 pM or less. In some embodiments, an anti-mesothelin antibody or antigen-binding fragment binds mesothelin (e.g., human mesothelin) with a $K_D$ of about 25 pM or less. In some embodiments, an anti-mesothelin antibody or antigen-binding fragment binds mesothelin (e.g., human mesothelin) with a $K_D$ of about 10 pM or less. In some embodiments, an anti-mesothelin antibody or antigen-binding fragment binds mesothelin (e.g., human mesothelin) with a $K_D$ of about 1 pM or less. In some embodiments, the dissociation constant of the binding agent (e.g., an antibody) for mesothelin is the dissociation constant determined using a mesothelin protein immobilized on a Biacore chip and the binding agent flowed over the chip. In some embodiments, the dissociation constant of the binding agent (e.g., an antibody) for mesothelin is the dissociation constant determined using the binding agent captured by an anti-human IgG antibody on a Biacore chip and soluble mesothelin flowed over the chip.

The anti-mesothelin antibodies or antigen-binding fragments of the present disclosure can be analyzed for their physical, chemical and/or biological properties by various methods known in the art. In some embodiments, an anti-mesothelin antibody is tested for its ability to bind mesothelin (e.g., human mesothelin). Binding assays include, but are not limited to, SPR (e.g., Biacore), ELISA, and FACS. In addition, antibodies can be evaluated for solubility, stability, thermostability, viscosity, expression levels, expression quality, and/or purification efficiency.

Epitope mapping is a method of identifying the binding site, region, or epitope on a target protein where an antibody binds. A variety of methods are known in the art for mapping epitopes on target proteins. These methods include mutagenesis, including but not limited to, shotgun mutagenesis, site-directed mutagenesis, and alanine scanning; domain or fragment scanning; peptide scanning (e.g., Pepscan technology); display methods (e.g., phage display, microbial display, and ribosome/mRNA display); methods involving proteolysis and mass spectroscopy; and structural determination (e.g., X-ray crystallography and NMR). In some embodiments, anti-mesothelin antibodies or antigen-binding fragments described herein are characterized by assays including, but not limited to, N-terminal sequencing, amino acid analysis, HPLC, mass spectrometry, ion exchange chromatography, and papain digestion.

In some embodiments, an anti-mesothelin antibody or antigen-binding fragment is conjugated to a cytotoxic agent or moiety. In some embodiments, an anti-mesothelin antibody or antigen-binding fragment is conjugated to a cytotoxic agent to form an ADC (antibody-drug conjugate). In some embodiments, the cytotoxic moiety is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic moiety is a microtubule inhibitor including, but not limited to, auristatins, maytansinoids (e.g., DM1 and DM4), and tubulysins. In some embodiments, the cytotoxic moiety is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, an antibody is conjugated to one or more small molecule toxins, such as calicheamicins, maytansinoids, trichothenes, and CC1065.

In some embodiments, an anti-mesothelin antibody or antigen-binding fragment described herein is conjugated to a detectable substance or molecule that allows the agent to be used for diagnosis and/or detection. A detectable substance can include, but is not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), and phycoerythrin; bioluminescent materials, such as luciferase; radioactive materials, such as $^{212}$Bi, $^{14}$C, $^{57}$Co, $^{51}$Cr, $^{67}$Cu, $^{18}$F, $^{68}$Ga, $^{67}$Ga, $^{153}$Gd, $^{159}$Gd, $^{68}$Ge, $^{3}$H, $^{166}$Ho, $^{131}$I, $^{125}$I, $^{123}$I, $^{121}$I, $^{115}$In, $^{113}$In, $^{112}$In, $^{111}$In, $^{140}$La, $^{177}$Lu, $^{54}$Mn, $^{99}$Mo, $^{32}$P, $^{103}$Pd, $^{149}$Pm, $^{142}$Pr, $^{186}$Re, $^{188}$Re, $^{105}$Rh, $^{97}$Ru, $^{35}$S, $^{47}$Sc, $^{75}$Se, $^{153}$Sm, $^{113}$Sn, $^{117}$Sn, $^{85}$Sr, $^{99m}$Tc, $^{201}$Ti, $^{133}$Xe, $^{90}$Y, $^{69}$Yb, $^{175}$Yb, $^{65}$Zn; positron emitting metals; and magnetic metal ions positron emitting metals; and magnetic metal ions.

An anti-mesothelin antibody or antigen-binding fragment described herein can be attached to a solid support. Such solid supports include, but are not limited to, glass, cellulose, polyacrylamide, nylon, polystyrene, polyvinyl chloride, or polypropylene. In some embodiments, an immobilized anti-mesothelin antibody or antigen-binding fragment is used in an immunoassay. In some embodiments, an immobilized anti-mesothelin antibody or antigen-binding fragment is used in purification of the target antigen (e.g., human mesothelin).

5.3 CARs, TCRs and Genetically Engineered Immune Effector Cells

The anti-mesothelin antibodies or antigen-binding fragments described herein can be used as part of a chimeric antigen receptor (CAR) or a T-Cell Receptor (TCR) that can be expressed in an immune effector cell for cancer treatment. As such, provided herein are also CARs and TCRs that specifically bind mesothelin (e.g., human mesothelin), immune effector cells that express such CARs or TCRs, and the uses of such cells.

5.3.1 TCRs

Provided herein are T cell receptors (TCRs) that specifically bind mesothelin ("mesothelin TCR"). TCRs are antigen-specific molecules that are responsible for recognizing antigenic peptides presented in the context of a product of the MHC on the surface of APCs or any nucleated cells. This system endows T cells, via their TCRs, with the potential ability to recognize the entire array of intracellular antigens expressed by a cell (including virus proteins) that are processed into short peptides, bound to an intracellular MHC molecule, and delivered to the surface as a peptide-MHC complex. This system allows foreign protein (e.g., mutated cancer antigen or virus protein) or aberrantly expressed protein to serve a target for T cells (e.g., Davis and Bjorkman (1988) Nature, 334, 395-402; Davis et al. (1998) Annu Rev Immunol, 16, 523-544).

The interaction of a TCR and a peptide-MHC complex can drive the T cell into various states of activation, depending on the affinity (or dissociation rate) of binding. The TCR recognition process allows a T cell to discriminate between a normal, healthy cell and, for example, one that has become transformed via a virus or malignancy, by providing a diverse repertoire of TCRs, wherein there is a high probability that one or more TCRs will be present with a binding affinity for the foreign peptide bound to an MHC molecule that is above the threshold for stimulating T cell activity (Manning and Kranz (1999) Immunology Today, 20, 417-422).

Wild type TCRs isolated from either human or mouse T cell clones that were identified by in vitro culturing have been shown to have relatively low binding affinities ($K_D$=1-300 μM) (Davis et al. (1998) Annu Rev Immunol, 16, 523-544). This is partly because that T cells that develop in the thymus are negatively selected (tolerance induction) on self-peptide-MHC ligands, such that T cells with too high of an affinity are deleted (Starr et al. (2003) Annu Rev Immunol, 21, 139-76). To compensate for these relatively low affinities, T cells have evolved a co-receptor system in which the cell surface molecules CD4 and CD8 bind to the MHC molecules (class II and class I, respectively) and synergize with the TCR in mediating signaling activity. CD8 is particularly effective in this process, allowing TCRs with very low affinity (e.g., $K_D$=300 μM) to mediate potent antigen-specific activity.

Directed evolution can be used to generate TCRs with higher affinity for a specific peptide-MHC complex. Methods that can be used include yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), and T cell display (Chervin et al. (2008) J Immunol Methods, 339, 175-84). All three approaches involve engineering, or modifying, a TCR that exhibits the normal, low affinity of the wild-type TCR, to increase the affinity for the cognate peptide-MHC complex (the original antigen that the T cells were specific for).

As such, in some embodiments, provided herein are TCRs comprising an anti-mesothelin antibody or antigen-binding fragment described herein. The anti-mesothelin antibody or antigen-binding fragment can be any anti-mesothelin antibody or antigen-binding fragment described herein. In some embodiments, the anti-mesothelin antibody or antigen-binding fragment is the scFv designated as M6, M7, M8, M10, M12, M13, M15, M20, M22, M24, M27, M28, M31, M32 or M37 provided herein. For illustrative purposes, in some embodiments, the TCRs provided herein can comprise an anti-mesothelin antibody or antigen-binding fragment having a VL and a VH, wherein the VL comprises VL CDR1, CDR2 and CDR3 and the VH comprises VH CDR1, CDR2 and CDR3, and wherein the VL CDR1, VL CDR2, VL CDR3, VH CDR1, VH CDR2 and VH CDR3 have the amino acid sequences of SEQ ID NOs: 1, 2, 3, 4, 5, and 6 respectively.

In some embodiments, the TCRs provided herein can comprise the scFv designated as M12 as provided herein.

In some embodiments, the TCRs provided herein comprise an alpha (α) chain and a beta (β) chain. The constant region of TCR α chain and β chain are encoded by TRAC and TRBC, respectively. A human TRAC can have an amino acid sequence corresponding to UniProtKB/Swiss-Prot No.: P01848.2 (Accession: P01848.2 GI: 1431906459). A human TRBC can have an amino acid sequence corresponding to the GenBank sequence ALC78509.1 (Accession: ALC78509.1 GI: 924924895). In some embodiments, the TCRs provided herein comprise a TCR α chain comprising an anti-mesothelin antibody or antigen-binding fragment provided herein. In some embodiments, the TCRs provided herein comprise a TCR β chain comprising an anti-mesothelin antibody or antigen-binding fragment provided herein. In some embodiments, the TCR comprises a gamma chain (γ) and a delta (δ) chain. The constant region of TCR γ chain and δ chain are encoded by encoded by TRGC and TRDC, respectively. A human TRGC can have an amino acid sequence corresponding to UniProtKB/Swiss-Prot: POCF51.1 (Accession: POCF51.1 GI: 294863156), or an amino acid sequence corresponding to UniProtKB/Swiss-Prot: P03986.2 (Accession: P03986.2 GI: 1531253869). A human TRDC can have an amino acid sequence corresponding to the UniProtKB/Swiss-Prot: B7Z8K6.2 (Accession: B7Z8K6.2 GI: 294863191). In some embodiments, the TCRs provided herein comprise a TCR γ chain comprising an anti-mesothelin antibody or antigen-binding fragment provided herein. In some embodiments, the TCRs provided herein comprise a TCR δ chain comprising an anti-mesothelin antibody or antigen-binding fragment provided herein.

5.3.2 CARs

CARs are engineered receptors that provide both antigen binding and immune effector cell activation functions. CARs can be used to graft the specificity of an antibody, such as a monoclonal antibody, onto an immune effector cell such as a T cell, a NK cell, or a macrophage. CARs can retarget immune effector cells (e.g., T cells) to tumor surface antigens in HLA-independent manner (Sadelain et al., *Nat. Rev. Cancer.* 3(1):35-45 (2003); Sadelain et al., *Cancer Discovery* 3(4):388-398 (2013); Rafiq and Brentjens (2016). *Nat Rev Clin Oncol* 13(6): 370-383). The typical structure of a CAR molecule includes an extracellular antigen-binding domain (e.g., scFv), a transmembrane domain (TM) and an intracellular signaling domain. The extracellular antigen-binding domain of a CAR is usually derived from a monoclonal antibody (mAb) or from receptors or their ligands. Antigen binding by the CARs triggers phosphorylation of immunoreceptor tyrosine-based activation motifs (ITAMs) in the intracellular domain, initiating a signaling cascade required for cytolysis induction, cytokine secretion, and proliferation. CAR-expressing T cells ("CART"s) can be classified into three generations according to the presence of intracellular co-stimulatory signals.

In some embodiments, provided herein are CARs that specifically binds mesothelin ("mesothelin CAR"). In some embodiments, the CAR can be a "first generation," "second generation" or "third generation" CAR (see, for example, Sadelain et al., *Cancer Discov.* 3(4):388-398 (2013); Jensen et al, *Immunol. Rev.* 257:127-133 (2014); Sharpe et al, *Dis. Model Mech.* 8(4):337-350 (2015); June et al (2018), *Science* 359(6382): 1361-1365).

"First generation" CARs are typically composed of an extracellular antigen binding domain, for example, a single-chain variable fragment (scFv), fused to a transmembrane domain, which is fused to a cytoplasmic/intracellular domain of the T cell receptor chain. "First generation" CARs typically have the intracellular domain from the CD3-chain, which is the primary transmitter of signals from endogenous T cell receptors (TCRs). "First generation" CARs can provide de novo antigen recognition and cause activation of both CD4$^+$ and CD8$^+$ T cells through their CD3ζ chain signaling domain in a single fusion molecule, independent of HLA-mediated antigen presentation. "Second-generation" CARs comprise a cancer antigen-binding domain fused to an intracellular signaling domain capable of activating immune effector cells such as T cells and a co-stimulatory domain designed to augment immune effector cell, such as T cell, potency and persistence (Sadelain et al., *Cancer Discov.* 3:388-398 (2013)). CAR design can therefore combine antigen recognition with signal transduction, two functions that are physiologically borne by two separate complexes, the TCR heterodimer and the CD3 complex. "Second generation" CARs include an intracellular domain from various co-stimulatory receptors, for example, CD28, 4-1BB, ICOS, OX40, and the like, in the cytoplasmic tail of the CAR to provide additional signals to the cell. "Second generation" CARs provide both co-stimulation, for example, by CD28 or 4-1BB domains, and activation, for example, by a CD3ζ signaling domain. Studies have indicated that "Second Generation" CARs can improve the anti-tumor activity of T cells. In 2017, FDA approved two anti-CD19 CART cell products for the treatment of relapsed B-cell precursor acute lymphoblastic leukemia (B-ALL) and B-cell Non-Hodgkin Lymphoma. "Third generation" CARs provide multiple co-stimulation, for example, by comprising both CD28 and 4-1BB domains, and activation, for example, by comprising a CD3ζ activation domain.

As such, provided herein are CARs that specifically binds mesothelin, comprising, from N-terminus to C-terminus: (a) a mesothelin-binding domain comprising an anti-mesothelin antibody or antigen-binding fragment provided herein, (b) a transmembrane domain, and (c) a cytoplasmic domain. The anti-mesothelin antibody or antigen-binding fragment can be any anti-mesothelin antibody or antigen-binding fragment described herein. For illustrative purposes, in some embodiments, the CARs provided herein can comprise an anti-mesothelin antibody or antigen-binding fragment having a VL and a VH, wherein the VL comprises VL CDR1, CDR2 and CDR3 and the VH comprises VH CDR1, CDR2 and CDR3, and wherein the VL CDR1, VL CDR2, VL CDR3, VH CDR1, VH CDR2 and VH CDR3 have the amino acid sequences of SEQ ID NOs: 1, 2, 3, 4, 5, and 6, respectively. In some embodiments, the CARs provided herein can comprise the scFv designated as M12 as provided herein.

In some embodiments, the TCRs provided herein can comprise an anti-mesothelin antibody or antigen-binding fragment that is the scFv designated as M12 provided herein.

In some embodiments, the transmembrane domain of the CARs provided herein comprises a hydrophobic alpha helix that spans at least a portion of the membrane. Different transmembrane domains result in different receptor stability. After antigen recognition, receptors cluster and a signal is transmitted to the cell. In some embodiments, the transmembrane domain of the CAR provided herein can be derived from a protein or polypeptide that is naturally expressed in an immune effector cell. A transmembrane domain derived from a protein or polypeptide means that the transmembrane domain comprises the entire transmembrane region of the protein or polypeptide, or a fragment thereof. In some embodiments, the CAR provided herein can have a transmembrane domain derived from CD8, CD28, CD3ζ, CD4, 4-1BB, OX40, ICOS, CTLA-4, PD-1, LAG-3, 2B4, BTLA, T-cell receptor (TCR) α chain, TCR β chain, or TCR ζ chain, CDR, CD45, CD5, CD8, CD9, CD16, CD22, CD33, CD37, CD64, CD80, CD86, CD134, CD154, or other polypeptides expressed in the immune effector cell. In some embodiments, the transmembrane domain of CARs provided herein comprises the transmembrane region of CD8, CD28, CD3ζ, CD4, 4-1BB, OX40, ICOS, CTLA-4, PD-1, LAG-3, 2B4, BTLA, T-cell receptor (TCR) α chain, TCR β chain, or TCR ζ chain, CD3ε, CD45, CD5, CD8, CD9, CD16, CD22, CD33, CD37, CD64, CD80, CD86, CD134, CD154, or other polypeptides expressed in the immune effector cell.

In some embodiments, the transmembrane domain of CARs provided herein is derived from CD8. In some embodiments, the transmembrane domain comprises the transmembrane region of CD8. In some embodiments, the transmembrane domain is derived from CD28. In some embodiments, the transmembrane domain comprises the transmembrane region of CD28. In some embodiments, the transmembrane domain is derived from CD3ζ. In some embodiments, the transmembrane domain comprises the transmembrane region of CD3ζ. In some embodiments, the transmembrane domain is derived from CD4. In some embodiments, the transmembrane domain comprises the transmembrane region of CD4. In some embodiments, the transmembrane domain is derived from 4-1BB. In some embodiments, the transmembrane domain comprises the transmembrane region of 4-1BB. In some embodiments, the transmembrane domain is derived from OX40. In some embodiments, the transmembrane domain comprises the transmembrane region of OX40. In some embodiments, the transmembrane domain is derived from ICOS. In some embodiments, the transmembrane domain comprises the transmembrane region of ICOS. In some embodiments, the transmembrane domain is derived from CTLA-4. In some embodiments, the transmembrane domain comprises the transmembrane region of CTLA-4. In some embodiments, the transmembrane domain is derived from PD-1. In some embodiments, the transmembrane domain comprises the transmembrane region of PD-1. In some embodiments, the transmembrane domain is derived from LAG-3. In some embodiments, the transmembrane domain comprises the transmembrane region of LAG-3. In some embodiments, the transmembrane domain is derived from 2B4. In some embodiments, the transmembrane domain comprises the transmembrane region of 2B4. In some embodiments, the transmembrane domain is derived from BTLA. In some embodiments, the transmembrane domain comprises the transmembrane region of BTLA. In some embodiments, the transmembrane domain is derived from TCR α chain. In some embodiments, the transmembrane domain comprises the transmembrane region of TCR α chain. In some embodiments, the transmembrane domain is derived from TCR β chain. In some embodiments, the transmembrane domain comprises the transmembrane region of TCR β chain. In some embodiments, the transmembrane domain is derived from TCR ζ chain. In some embodiments, the transmembrane domain comprises the transmembrane region of TCR ζ chain. In some embodiments, the transmembrane domain is derived from CD3ε. In some embodiments, the transmembrane domain comprises the transmembrane region of CD3ε. In some embodiments, the transmembrane domain is derived from CD45. In some embodiments, the transmembrane domain comprises the transmembrane region of CD45. In some embodiments, the transmembrane domain is derived from CD5. In some embodiments, the transmembrane domain comprises the transmembrane region of CD5. In some embodiments, the transmembrane domain is derived from CD8. In some embodiments, the transmembrane domain comprises the transmembrane region of CD8. In some embodiments, the transmembrane domain is derived from CD9. In some embodiments, the transmembrane domain comprises the transmembrane region of CD9. In some embodiments, the transmembrane domain is derived from CD16. In some embodiments, the transmembrane domain comprises the transmembrane region of CD16. In some embodiments, the transmembrane domain is derived from CD22. In some embodiments, the transmembrane domain comprises the transmembrane region of CD22. In some embodiments, the transmembrane domain is derived from CD33. In some embodiments, the transmembrane domain comprises the transmembrane region of CD33. In some embodiments, the transmembrane domain is derived from CD37. In some embodiments, the transmembrane domain comprises the transmembrane region of CD37. In some embodiments, the transmembrane domain is derived from CD64. In some embodiments, the transmembrane domain comprises the transmembrane region of CD64. In some embodiments, the transmembrane domain is derived from CD80. In some embodiments, the transmembrane domain comprises the transmembrane region of CD80. In some embodiments, the transmembrane domain is derived from CD86. In some embodiments, the transmembrane domain comprises the transmembrane region of CD86. In some embodiments, the transmembrane domain is derived from CD134. In some embodiments, the transmembrane domain comprises the transmembrane region of CD134. In some embodiments, the transmembrane domain is derived from CD154. In some embodiments, the transmembrane domain comprises the transmembrane region of CD154. Exemplary transmembrane domains are described below in more detail.

In some embodiments, the transmembrane domain can be synthetic, in which case it comprises predominantly hydrophobic residues such as leucine and valine. Optionally, the transmembrane domain can be derived from a polypeptide that is not naturally expressed in the immune effector cell, so long as the transmembrane domain can function in transducing signal from antigen bound to the CAR to the intracellular signaling and/or co-stimulatory domains. In some embodiments, the transmembrane domain can comprise a triplet of phenylalanine, tryptophan and valine at each end. Optionally, a short oligo- or polypeptide linker, preferably between 2 and 10 amino acids in length can form the linkage between the transmembrane domain and the cytoplasmic signaling domain of the CAR. A glycine-serine doublet provides a particularly suitable linker.

Cytoplasmic domains of CARs provided herein can contain a signaling domain that functions in the immune effector cell expressing the CAR. Such a signaling domain can be, for example, derived from CD3ζ, Fc receptor γ, FcγRIIa, FcRβ (FcεR1b), CD3γ, CD3δ, CD3ε, CD79a, CD79b, DAP10, or DAP12. A signaling domain can also be a combination of signaling domains derived from molecules selected from CD3ζ, Fc receptor γ, FcγRIIa, FcRβ (FcεR1b), CD3γ, CD3δ, CD3ε, CD79a, CD79b, DAP10, and DAP12. A signaling domain derived from a protein or polypeptide refers to the domain of the protein or polypeptide that is responsible for activating the immune effector cell (e.g., a T cell), or a fragment thereof that retains its activation function. In general, the signaling domain induces persistence, trafficking and/or effector functions in the transduced immune effector cells such as T cells (Sharpe et al., *Dis. Model Mech.* 8:337-350 (2015); Finney et al., *J. Immunol.* 161:2791-2797 (1998); Krause et al., *J. Exp. Med.* 188:619-626 (1998)). The signaling domain of a protein or polypeptide can be the intracellular domain of the protein or polypeptide. In some embodiments, the signaling domain comprises the intracellular domain of CD3ζ, FcRγ, FcγRIIa, FcRβ, CD3γ, CD3δ, CD3ε, CD5, CD22, CD79a, CD79b, DAP10, DAP12, or any combination thereof.

In some embodiments, the cytoplasmic domain of CARs provided herein comprises a signaling domain derived from CD3ζ. In some embodiments, the signaling domain comprises the intracellular domain of CD3ζ. In some embodiments, the cytoplasmic domain comprises a signaling domain derived from FcRγ. In some embodiments, the signaling domain comprises the intracellular domain of FcRγ. In some embodiments, the cytoplasmic domain comprises a signaling domain derived from FcγRIIa. In some embodiments, the signaling domain comprises the intracellular domain of FcγRIIa. In some embodiments, the cytoplasmic domain comprises a signaling domain derived from FcRβ. In some embodiments, the signaling domain comprises the intracellular domain of FcRβ. In some embodiments, the cytoplasmic domain comprises a signaling domain derived from CD3γ. In some embodiments, the signaling domain comprises the intracellular domain of CD3γ. In some embodiments, the cytoplasmic domain comprises a signaling domain derived from CD3δ. In some embodiments, the signaling domain comprises the intracellular domain of CD3δ. In some embodiments, the cytoplasmic domain comprises a signaling domain derived from CD3ε. In some embodiments, the signaling domain comprises the intracellular domain of CD3ε. In some embodiments, the cytoplasmic domain comprises a signaling domain derived from CD5. In some embodiments, the signaling domain comprises the intracellular domain of CD5. In some embodiments, the cytoplasmic domain comprises a signaling domain derived from CD22. In some embodiments, the signaling domain comprises the intracellular domain of CD22. In some embodiments, the cytoplasmic domain comprises a signaling domain derived from CD79a. In some embodiments, the signaling domain comprises the intracellular domain of CD79a. In some embodiments, the cytoplasmic domain comprises a signaling domain derived from CD79b. In some embodiments, the signaling domain comprises the intracellular domain of CD79b. In some embodiments, the cytoplasmic domain comprises a signaling domain derived from DAP10. In some embodiments, the signaling domain comprises the intracellular domain of DAP10. In some embodiments, the cytoplasmic domain comprises a signaling domain derived from DAP12. In some embodiments, the signaling domain comprises the intracellular domain of DAP12. Exemplary signaling domains are described below in more detail.

In some embodiments, the cytoplasmic domain of CARs provided herein further comprises a co-stimulatory domain. In some embodiments, the cytoplasmic domain of CARs provided herein further comprises two co-stimulatory domains. Such a co-stimulatory domain can provide increased activation of an immune effector cell (e.g., T cell). A co-stimulatory signaling domain can be derived from, for example, CD28, 4-1BB (CD137), OX40, ICOS, DAP10, 2B4, CD27, CD30, CD40, CD2, CD7, LIGHT, TIGIT, GITR, TLR, DR3, or CD43. A co-stimulatory domain derived from a protein or polypeptide refers to the domain of the protein or polypeptide that is responsible for providing increased activation of an immune effector cell (e.g., T cell), or a fragment thereof that retains its activation function. In some embodiments, the co-stimulatory domain of CARs provided herein comprises the intracellular domain of CD28, 4-1BB (CD137), OX40, ICOS, DAP10, 2B4, CD27, CD30, CD40, CD2, CD7, LIGHT, TIGIT, GITR, TLR, DR3, or CD43. In some embodiments, the cytoplasmic domain of CARs provided herein comprises a co-stimulatory domain derived from CD28. In some embodiments, the co-stimulatory domain comprises the intracellular domain of CD28. In some embodiments, the cytoplasmic domain comprises a co-stimulatory domain derived from 4-1BB. In some embodiments, the co-stimulatory domain comprises the intracellular domain of 4-1BB. In some embodiments, the cytoplasmic domain comprises a co-stimulatory domain derived from OX40. In some embodiments, the co-stimulatory domain comprises the intracellular domain of OX40. In some embodiments, the cytoplasmic domain comprises a co-stimulatory domain derived from ICOS. In some embodiments, the co-stimulatory domain comprises the intracellular domain of ICOS. In some embodiments, the cytoplasmic domain comprises a co-stimulatory domain derived from DAP10. In some embodiments, the co-stimulatory domain comprises the intracellular domain of DAP10. In some embodiments, the cytoplasmic domain comprises a co-stimulatory domain derived from 2B4. In some embodiments, the co-stimulatory domain comprises the intracellular domain of 2B4. In some embodiments, the cytoplasmic domain comprises a co-stimulatory domain derived from CD27. In some embodiments, the co-stimulatory domain comprises the intracellular domain of CD27. In some embodiments, the cytoplasmic domain comprises a co-stimulatory domain derived from CD30. In some embodiments, the co-stimulatory domain comprises the intracellular domain of CD30. In some embodiments, the cytoplasmic domain comprises a co-stimulatory domain derived from CD40. In some embodiments, the co-stimulatory domain comprises the intracellular domain of CD40. In some embodiments, the cytoplasmic domain comprises a co-stimulatory domain derived from CD2. In some embodiments, the co-stimulatory domain comprises the intracellular domain of CD2. In some embodiments, the cytoplasmic domain comprises a co-stimulatory domain derived from CD7. In some embodiments, the co-stimulatory domain comprises the intracellular domain of CD7. In some embodiments, the cytoplasmic domain comprises a co-stimulatory domain derived from LIGHT. In some embodiments, the co-stimulatory domain comprises the intracellular domain of LIGHT. In some embodiments, the cytoplasmic domain comprises a co-stimulatory domain derived from TIGIT. In some embodiments, the co-stimulatory domain comprises the intracellular domain of TIGIT. In some embodiments, the cytoplasmic domain comprises a co-stimulatory domain derived from GITR. In some embodiments, the co-stimulatory domain comprises the intracellular domain of GITR. In some embodiments, the cytoplasmic domain comprises a co-stimulatory domain derived from TLR. In some embodiments, the co-stimulatory domain comprises the intracellular domain of TLR. In some embodiments, the cytoplasmic domain comprises a co-stimulatory domain derived from DR3. In some embodiments, the co-stimulatory domain comprises the intracellular domain of DR3. In some embodiments, the cytoplasmic domain comprises a co-stimulatory domain derived from CD43. In some embodiments, the co-stimulatory domain comprises the intracellular domain of CD43. Exemplary co-stimulatory domains are described below in more detail.

CARs comprising an intracellular domain that comprises a co-stimulatory domain derived from 4-1BB, ICOS or DAP-10 have been described previously (see U.S. Pat. No. 7,446,190, which is incorporated herein by reference, which also describes representative sequences for 4-1BB, ICOS and DAP-10). In some embodiments, the cytoplasmic domain of a CAR can comprise two co-stimulatory domains derived from two co-stimulatory receptors, such as CD28 and 4-1BB (see Sadelain et al., *Cancer Discov.* 3(4):388-398 (2013)), or CD28 and OX40, or other combinations of co-stimulatory ligands, as disclosed herein.

The extracellular domain of a CAR can be fused to a leader or a signal peptide that directs the nascent protein into the endoplasmic reticulum and subsequent translocation to the cell surface. It is understood that, once a polypeptide containing a signal peptide is expressed at the cell surface, the signal peptide has generally been proteolytically removed during processing of the polypeptide in the endoplasmic reticulum and translocation to the cell surface. Thus, a polypeptide such as a CAR is generally expressed at the cell surface as a mature protein lacking the signal peptide, whereas the precursor form of the polypeptide includes the signal peptide. A signal peptide or leader can be essential if a CAR is to be glycosylated and/or anchored in the cell membrane. The signal sequence or leader is a peptide sequence generally present at the N-terminus of newly synthesized proteins that directs their entry into the secretory pathway. The signal peptide is covalently joined to the N-terminus of the extracellular antigen-binding domain of a CAR as a fusion protein. Any suitable signal peptide, as are well known in the art, can be applied to a CAR to provide cell surface expression in an immune cell (see Gierasch Biochem. 28:923-930 (1989); von Heijne, J. Mol. Biol. 184 (1):99-105 (1985)). Particularly useful signal peptides can be derived from cell surface proteins naturally expressed in the immune cell provided herein, including any of the signal peptides of the polypeptides disclosed herein. Thus, any suitable signal peptide can be utilized to direct a CAR to be expressed at the cell surface of an immune effector cell provided herein.

NP_932170 for reference to domains within CD3ζ, for example, signal peptide, amino acids 1 to 21; extracellular domain, amino acids 22 to 30; transmembrane region, amino acids 31 to 51; intracellular domain, amino acids 52 to 164. In some embodiments, a CAR can have a transmembrane domain derived from CD3ζ. The transmembrane domain can comprise the transmembrane region of CD3ζ (e.g., amino acids 31 to 51 of the sequence below), or a fragment thereof. In some embodiments, the cytoplasmic domain of a CAR can comprise a signaling domain derived from CD3ζ. In some embodiments, a signaling domain of CD3ζ can comprise the intracellular domain of CD3ζ (e.g., amino acids 52 to 164 of the sequence below), or a fragment thereof. It is understood that sequences of CD3ζ that are shorter or longer than a specific delineated domain can be included in a CAR, if desired.

(SEQ ID NO: 18)

```
  1   MKWKALFTAA ILQAQLPITE AQSFGLLDPK LCYLLDGILF IYGVILTALF LRVKFSRSAD
 61   APAYQQGQNQ LYNELNLGRR EEYDVLDKRR GRDPEMGGKP QRRKNPQEGL YNELQKDKMA
121   EAYSEIGMKG ERRRGKGHDG LYQGLSTATK DTYDALHMQA LPPR
```

In some embodiments, a CAR can also comprise a spacer region or sequence that links the domains of the CAR to each other. For example, a spacer can be included between a signal peptide and an antigen binding domain, between the antigen binding domain and the transmembrane domain, between the transmembrane domain and the intracellular domain, and/or between domains within the intracellular domain, for example, between a stimulatory domain and a co-stimulatory domain. The spacer region can be flexible enough to allow interactions of various domains with other polypeptides, for example, to allow the antigen binding domain to have flexibility in orientation in order to facilitate antigen recognition. The spacer region can be, for example, the hinge region from an IgG, the CH$_2$CH$_3$ (constant) region of an immunoglobulin, and/or portions of CD3 (cluster of differentiation 3) or some other sequence suitable as a spacer. In some embodiments, a CAR disclosed herein comprises a hinge domain that connects the mesothelin binding domain and the transmembrane domain. In some embodiments, the hinge domain comprises human CD8 hinge domain. In some embodiments, the hinge domain comprises human CD28 hinge domain.

Provided below are some exemplary molecules from which domains of the CARs provided herein can be derived.

CD3ζ. CD3ζ comprises 3 Immune-receptor-Tyrosine-based-Activation-Motifs (ITAMs), and transmits an activation signal to the cell, for example, a cell of the lymphoid lineage such as a T cell, after antigen is bound. A CD3ζ polypeptide can have an amino acid sequence corresponding to the sequence having GenBank No. NP_932170 (NP_932170.1, GI:37595565; see below), or fragments thereof. In some embodiments, a CD3ζ signaling domain has an amino acid sequence of amino acids 52 to 164 of the CD3ζ polypeptide sequence provided below, or a fragment thereof that is sufficient for signaling activity. See GenBank FcRγ Activating types of IgG receptor FcγRs form multimeric complexes including the Fc receptor common γ chain (FcRγ) that contains an intracellular tyrosine-based activating motif (ITAM), whose activation triggers oxidative bursts, cytokine release, phagocytosis, antibody-dependent cell-mediated cytotoxicity, and degranulation. An FcRγ polypeptide can have an amino acid sequence corresponding to the sequence having NCBI Reference Sequence: NP_004097.1 (GI: 4758344) or fragments thereof. See GenBank NP_004097 for reference to domains within FcRγ, for example, signal peptide, amino acids 1 to 18; extracellular domain, amino acids 19 to 23; transmembrane region, amino acids 24 to 44; intracellular domain, amino acids 45 to 86. In some embodiments, a CAR can comprise a transmembrane domain derived from FcRγ. In some embodiments, the transmembrane domain of the CAR comprises the transmembrane region of FcRγ, or a fragment thereof. In some embodiments, the cytoplasmic domain of a CAR can comprise a signaling domain derived from FcRγ. In some embodiments, the signaling domain comprises the intracellular domain of FcRγ, or a fragment thereof. It is understood that sequences of FcRγ that are shorter or longer than a specific delineated domain can be included in a CAR, if desired.

FcγRIIa is a cell surface receptor found on phagocytic cells such as macrophages and neutrophils, and is involved in the process of phagocytosis and clearing of immune complexes. By binding to IgG it initiates cellular responses against pathogens and soluble antigens. FcγRIIa also promotes phagocytosis of opsonized antigens. An FcγRIIa polypeptide can have an amino acid sequence corresponding to the sequence having NCBI Reference Sequence: NP_001129691.1, or fragments thereof. See NCBI Reference Sequence NP_001129691.1 for reference to domains within FcγRIIa, for example, signal peptide, amino acids 1 to 33; extracellular domain, amino acids 34 to 217; transmembrane region, amino acids 218 to 240; intracellular domain, amino acids 241 to 317. In some embodiments, a CAR can comprise a transmembrane domain derived from FcγRIIa. In some embodiments, the transmembrane domain of the CAR comprises the transmembrane region of FcγRIIa, or a fragment thereof. In some embodiments, the cytoplasmic domain of a CAR can comprise a signaling domain derived from FcγRIIa. In some embodiments, the signaling domain comprises the intracellular domain of FcγRIIa, or a fragment thereof. It is understood that sequences of FcγRIIa that are shorter or longer than a specific delineated domain can be included in a CAR, if desired.

FcRβ (FcεR1b) is a high affinity receptor that binds to the Fc region of immunoglobulins epsilon. Aggregation of FcRβ by multivalent antigens is required for the full mast cell response, including the release of preformed mediators (such as histamine) by degranulation and de novo production of lipid mediators and cytokines. FcRβ also mediates the secretion of important lymphokines. Binding of allergen to receptor-bound IgE leads to cell activation and the release of mediators responsible for the manifestations of allergy. An FcRβ polypeptide can have an amino acid sequence corresponding to the sequence having NCBI Reference Sequence: NP_000130.1, or fragments thereof. See NCBI Reference Sequence: NP_000130.1 for reference to domains within FcRβ, for example, intracellular domain, amino acids 1 to 59, 118 to 130, and 201 to 244; transmembrane region, amino acids 60 to 79, 98 to 117, 131 to 150, and 181 to 200; extracellular domain, amino acids 80 to 97, and 151 to 180. In some embodiments, the cytoplasmic domain of a CAR can comprise a signaling domain derived from FcRβ. In some embodiments, the signaling domain comprises an intracellular domain of FcRβ, or a fragment thereof. It is understood that sequences of FcRβ that are shorter or longer than a specific delineated domain can be included in a CAR, if desired.

CD3γ (T-cell surface glycoprotein CD3 gamma chain), is part of the TCR-CD3 complex present on T-lymphocyte cell surface that plays an essential role in adaptive immune response. CD3γ contains immunoreceptor tyrosine-based activation motifs (ITAMs) in its cytoplasmic domain. In addition to this role of signal transduction in T-cell activation, CD3γ plays an essential role in the dynamic regulation of TCR expression at the cell surface. A CD3γ polypeptide can have an amino acid sequence corresponding to the sequence having NCBI Reference Sequence: NP_004097.1 (GI: 4758344), or fragments thereof. See GenBank NP_004097 for reference to domains within CD3γ, for example, signal peptide, amino acids 1 to 22; extracellular domain, amino acids 23 to 116; transmembrane region, amino acids 117 to 137; intracellular domain, amino acids 138 to 182. In some embodiments, a CAR can comprise a transmembrane domain derived from CD3γ. In some embodiments, the transmembrane domain of the CAR comprises the transmembrane region of CD3γ, or a fragment thereof. In some embodiments, the cytoplasmic domain of a CAR can comprise a signaling domain derived from CD3γ. In some embodiments, the signaling domain comprises the intracellular domain of CD3γ, or a fragment thereof. It is understood that sequences of CD3γ that are shorter or longer than a specific delineated domain can be included in a CAR, if desired.

CD3δ (T-cell surface glycoprotein CD3 delta chain), is part of the TCR-CD3 complex present on T-lymphocyte cell surface that plays an essential role in adaptive immune response. CD3δ contains immunoreceptor tyrosine-based activation motifs (ITAMs) in its cytoplasmic domain. In addition of this role of signal transduction in T-cell activation, CD3δ plays an essential role in thymocyte differentiation and participates in correct intracellular TCR-CD3 complex assembly and surface expression. CD3δ interacts with CD4 and CD8 and thus serves to establish a functional link between the TCR and coreceptors CD4 and CD8, which is needed for activation and positive selection of CD4 or CD8 T-cells. A CD3δ polypeptide can have an amino acid sequence corresponding to the sequence having NCBI Reference Sequence: NP_000723.1, or fragments thereof. See NCBI Reference Sequence: NP_000723.1 for reference to domains within CD3δ, for example, signal peptide, amino acids 1 to 21; extracellular domain, amino acids 22 to 105; transmembrane region, amino acids 106 to 126; intracellular domain, amino acids 127 to 171. In some embodiments, a CAR can comprise a transmembrane domain derived from CD3δ. In some embodiments, the transmembrane domain of the CAR comprises the transmembrane region of CD3δ, or a fragment thereof. In some embodiments, the cytoplasmic domain of a CAR can comprise a signaling domain derived from CD3δ. In some embodiments, the signaling domain comprises the intracellular domain of CD3δ, or a fragment thereof. It is understood that sequences of CD3δ that are shorter or longer than a specific delineated domain can be included in a CAR, if desired.

CD3ε (T-cell surface glycoprotein CD3 epsilon chain), is part of the TCR-CD3 complex present on T-lymphocyte cell surface that plays an essential role in adaptive immune response. CD3ε contains immunoreceptor tyrosine-based activation motifs (ITAMs) in its cytoplasmic domain. In addition of this role of signal transduction in T-cell activation, CD3ε plays an essential role in correct T-cell development. CD3ε initiates the TCR-CD3 complex assembly by forming the two heterodimers CD3δ/CD3γ and CD3γ/CD3γ. A CD3ε polypeptide can have an amino acid sequence corresponding to the sequence having NCBI Reference Sequence: NP_000724.1, or fragments thereof. See NCBI Reference Sequence: NP_000724.1 for reference to domains within CD3ε, for example, signal peptide, amino acids 1 to 22; extracellular domain, amino acids 23 to 126; transmembrane region, amino acids 127 to 152; intracellular domain, amino acids 153 to 207. In some embodiments, a CAR can comprise a transmembrane domain derived from CD3ε. In some embodiments, the transmembrane domain of the CAR comprises the transmembrane region of CD3ε, or a fragment thereof. In some embodiments, the cytoplasmic domain of a CAR can comprise a signaling domain derived from CD3ε. In some embodiments, the signaling domain comprises the intracellular domain of CD3ε, or a fragment thereof. It is understood that sequences of CD3ε that are shorter or longer than a specific delineated domain can be included in a CAR, if desired.

CD79a (B-cell antigen receptor complex-associated protein alpha chain) is required in cooperation with CD79b for initiation of the signal transduction cascade activated by binding of antigen to the B-cell antigen receptor complex (BCR) which leads to internalization of the complex, trafficking to late endosomes and antigen presentation. CD79a stimulates SYK autophosphorylation and activation. CD79a also binds to BLNK, bringing BLNK into proximity with SYK and allowing SYK to phosphorylate BLNK, and interacts with and increases activity of some Src-family tyrosine kinases. A CD79a polypeptide can have an amino acid sequence corresponding to the sequence having NCBI Reference Sequence: NP_001774.1, or fragments thereof. See NCBI Reference Sequence: NP_001774.1 for reference to domains within CD79a, for example, signal peptide, amino acids 1 to 32; extracellular domain, amino acids 33 to 143; transmembrane region, amino acids 144 to 165; intracellular domain, amino acids 166 to 226. In some embodiments, a CAR can comprise a transmembrane domain derived from CD79a. In some embodiments, the transmembrane domain of the CAR comprises the transmembrane region of CD79a, or a fragment thereof. In some embodiments, the cytoplasmic domain of a CAR can comprise a signaling domain derived from CD79a. In some embodiments, the signaling domain comprises the intracellular domain of CD79a, or a fragment thereof. It is understood that sequences of CD79a that are shorter or longer than a specific delineated domain can be included in a CAR, if desired.

CD79b (B-cell antigen receptor complex-associated protein beta chain) is required in cooperation with CD79a for initiation of the signal transduction cascade activated by the B-cell antigen receptor complex (BCR) which leads to internalization of the complex, trafficking to late endosomes and antigen presentation. CD79b enhances phosphorylation of CD79a. A CD79b polypeptide can have an amino acid sequence corresponding to the sequence having NCBI Reference Sequence: NP_000617.1, or fragments thereof. See NCBI Reference Sequence: NP_000617.1 for reference to domains within CD79b, for example, signal peptide, amino acids 1 to 28; extracellular domain, amino acids 29 to 159; transmembrane region, amino acids 160 to 180; intracellular domain, amino acids 181 to 229. In some embodiments, a CAR can comprise a transmembrane domain derived from CD79b. In some embodiments, the transmembrane domain of the CAR comprises the transmembrane region of CD79b, or a fragment thereof. In some embodiments, the cytoplasmic domain of a CAR can comprise a signaling domain derived from CD79b. In some embodiments, the signaling domain comprises the intracellular domain of CD79b, or a fragment thereof. It is understood that sequences of CD79b that are shorter or longer than a specific delineated domain can be included in a CAR, if desired.

DAP10. DAP10, also referred to as hematopoietic cell signal transducer, is a signaling subunit that associates with a large family of receptors in hematopoietic cells. A DAP10 polypeptide can have an amino acid sequence corresponding to the sequence having GenBank No. NP_055081.1 (GI: 15826850), or fragments thereof. See GenBank NP_055081 for reference to domains within DAP10, for example, signal peptide, amino acids 1 to 18; extracellular domain, amino acids 19 to 48; transmembrane region, amino acids 49 to 69; intracellular domain, amino acids 70 to 93. In some embodiments, the cytoplasmic domain of a CAR can comprise a signaling domain derived from DAP10. In some embodiments, the signaling domain comprises the intracellular domain of DAP10, or a fragment thereof. In some embodiments, the cytoplasmic domain comprises a co-stimulatory domain derived from DAP10. In some embodiments, the co-stimulatory domain comprises the intracellular domain of DAP10, or a fragment thereof. It is understood that sequences of DAP10 that are shorter or longer than a specific delineated domain can be included in a CAR, if desired.

DAP12. DAP12 is found in cells of the myeloid lineage, such as macrophages and granulocytes, where it associates, for instance, with the triggering receptor expressed on myeloid cell members (TREM) and MDL1 (myeloid DAP12-associating lectin 1/CLEC5A), both involved in inflammatory responses against pathogens like viruses and bacteria. In the lymphoid lineage, DAP12 is expressed in NK cells and associates with activating receptors such as the C-type lectin receptor NKG2C, the natural cytotoxicity receptor NKp44, and the short-tailed KIR3DS1 and KIR2DS1/2/5, respectively. In particular, NGK2C is the dominant activating NK cell receptor for controlling CMV infection in both humans and mice. It was found that a DAP12-containing CAR generated sufficient activating signals in NK cells upon cross-linking with its Ag. Töpfer et al., *J Immunol* 194:3201-12 (2015). A DAP12 polypeptide can have an amino acid sequence corresponding to the sequence having GenBank No. AAD09437.1 (GI: 2905996), or fragments thereof. See GenBank No. AAD09437.1 for reference to domains within DAP12, for example, signal peptide, amino acids 1 to 21; extracellular domain, amino acids 22 to 40; transmembrane region, amino acids 41 to 61; intracellular domain, amino acids 62 to 113. In some embodiments, the cytoplasmic domain of a CAR can comprise a signaling domain derived from DAP12. In some embodiments, the signaling domain comprises the intracellular domain of DAP12, or a fragment thereof. In some embodiments, the cytoplasmic domain comprises a co-stimulatory domain derived from DAP12. In some embodiments, the co-stimulatory domain comprises the intracellular domain of DAP12, or a fragment thereof. It is understood that sequences of DAP12 that are shorter or longer than a specific delineated domain can be included in a CAR, if desired.

CD28. Cluster of Differentiation 28 (CD28) is a protein expressed on T cells that provides co-stimulatory signals for T cell activation and survival. CD28 is the receptor for CD80 (B7.1) and CD86 (B7.2) proteins. A CD28 polypeptide can have an amino acid sequence corresponding to the sequence having GenBank No. P10747 (P10747.1, GI:115973) or NP_006130 (NP_006130.1, GI:5453611), as provided below, or fragments thereof. See GenBank NP_006130 for reference to domains within CD28, for example, signal peptide, amino acids 1 to 18; extracellular domain, amino acids 19 to 152; transmembrane domain, amino acids 153 to 179; intracellular domain, amino acids 180 to 220. In some embodiments, a CAR can comprise a hinge domain derived from CD28 (e.g., amino acids 114 to 152 of the sequence below, or a fragment thereof). In some embodiments, a CAR can comprise a transmembrane domain derived from CD28. In some embodiments, the transmembrane domain of the CAR comprises the transmembrane region of CD28 (e.g., amino acids 153 to 179 of the sequence below), or a fragment thereof. In some embodiments, the cytoplasmic domain of a CAR can comprise a co-stimulatory domain derived from CD28. In some embodiments, the co-stimulatory domain comprises the intracellular domain of CD28 (e.g., amino acids 180 to 220 of the sequence below), or a fragment thereof. In some embodiments, a CAR can comprise two domains derived from CD28, a co-stimulatory signaling domain and a transmembrane domain. In some embodiments, a CAR has an amino acid sequence comprising the transmembrane domain and the intracellular domain of CD28 and comprises amino acids 153 to 220 of CD28. In some embodiments, a CAR can comprise three domains derived from CD28, a transmembrane domain, a hinge domain and a co-stimulatory signaling domain. In another embodiment, a CAR comprises amino acids 114 to 220 of CD28. It is understood that sequences of CD28 that are shorter or longer than a specific delineated domain can be included in a CAR, if desired.

```
                                                                        (SEQ ID NO: 19)
  1    MLRLLLALNL  FPSIQVTGNK  ILVKQSPMLV  AYDNAVNLSC  KYSYNLFSRE  FRASLHKGLD

61    SAVEVCVVYG  NYSQQLQVYS  KTGFNCDGKL  GNESVTFYLQ  NLYVNQTDIY  FCKIEVMYPP

121    PYLDNEKSNG  TIIHVKGKHL  CPSPLFPGPS  KPFWVLVVVG  GVLACYSLLV  TVAFIIFWVR

181    SKRSRLLHSD  YMNMTPRRPG  PTRKHYQPYA  PPRDFAAYRS
```

4-1BB. 4-1BB, also referred to as tumor necrosis factor receptor superfamily member 9, can act as a tumor necrosis factor (TNF) ligand and have stimulatory activity. A 4-1BB polypeptide can have an amino acid sequence corresponding to the sequence having GenBank No. P41273 (P41273.1, GI:728739) or NP_001552 (NP_001552.2, GI:5730095) or fragments thereof. See GenBank NP_001552 for reference to domains within 4-1BB, for example, signal peptide, amino acids 1 to 17; extracellular domain, amino acids 18 to 186; transmembrane domain, amino acids 187 to 213; intracellular domain, amino acids 214 to 255. In some embodiments, a CAR can comprise a transmembrane domain derived from 4-1BB. In some embodiments, the transmembrane domain of the CAR comprises the transmembrane region of 4-1BB (e.g., amino acids 187 to 213 of the sequence below), or a fragment thereof. In some embodiments, the cytoplasmic domain of a CAR can comprise a co-stimulatory domain derived from 4-1BB. In some embodiments, the co-stimulatory domain comprises the intracellular domain of 4-1BB (e.g., amino acids 214 to 255 of the sequence below), or a fragment thereof. In some embodiments, a CAR can comprise two domains derived from 4-1BB, a co-stimulatory signaling domain and a transmembrane domain. In some embodiments, a CAR has an amino acid sequence comprising the transmembrane domain and the intracellular domain of 4-1BB and comprises amino acids 187 to 255 of 4-1BB. It is understood that sequences of 4-1BB that are shorter or longer than a specific delineated domain can be included in a CAR, if desired.

CAR can comprise a co-stimulatory domain derived from OX40. In some embodiments, the co-stimulatory domain comprises the intracellular domain of OX40, or a fragment thereof. In some embodiments, a CAR can comprise two domains derived from OX40, a co-stimulatory signaling domain and a transmembrane domain. In some embodiments, a CAR has an amino acid sequence comprising the transmembrane domain and the intracellular domain of OX40 and comprises amino acids 215 to 277 of OX40.

ICOS. Inducible T-cell co-stimulator precursor (ICOS), also referred to as CD278, is a CD28-superfamily co-stimulatory receptor that is expressed on activated T cells. An ICOS polypeptide can have an amino acid sequence corresponding to the sequence having GenBank No. NP_036224 (NP_036224.1, GI:15029518), or fragments thereof. See GenBank NP_036224 for reference to domains within ICOS, for example, signal peptide, amino acids 1 to 20; extracellular domain, amino acids 21 to 140; transmembrane domain, amino acids 141 to 161; intracellular domain, amino acids 162 to 199. In some embodiments, a CAR can comprise a transmembrane domain derived from ICOS. In some embodiments, the transmembrane domain of the CAR comprises the transmembrane region of ICOS, or a fragment thereof. In some embodiments, the cytoplasmic domain of a CAR can comprise a co-stimulatory domain derived from ICOS. In some embodiments, the co-stimulatory domain comprises the intracellular domain of ICOS, or a fragment thereof. In some embodiments, a CAR can comprise two domains derived from ICOS, a co-stimulatory signaling

```
                                                                        (SEQ ID NO: 20)
  1    MGNSCYNIVA  TLLLVLNFER  TRSLQDPCSN  CPAGTFCDNN  RNQICSPCPP  NSFSSAGGQR

61    TCDICRQCKG  VFRTRKECSS  TSNAECDCTP  GFHCLGAGCS  MCEQDCKQGQ  ELTKKGCKDC

121    CFGTFNDQKR  GICRPWTNCS  LDGKSVLVNG  TKERDVVCGP  SPADLSPGAS  SVTPPAPARE

181    PGHSPQIISF  FLALTSTALL  FLLFFLTLRF  SVVKRGRKKL  LYIFKQPFMR  PVQTTQEEDG

241    CSCRFPEEEE  GGCEL
```

OX40. OX40, also referred to as tumor necrosis factor receptor superfamily member 4 precursor or CD134, is a member of the TNFR-superfamily of receptors. An OX40 polypeptide can have an amino acid sequence corresponding to the sequence having GenBank No. P43489 (P43489.1, GI:1171933) or NP_003318 (NP_003318.1, GI:4507579), or fragments thereof. See GenBank NP_003318 for reference to domains within OX40, for example, signal peptide, amino acids 1 to 28; extracellular domain, amino acids 29 to 214; transmembrane domain, amino acids 215 to 235; intracellular domain, amino acids 236 to 277. It is understood that sequences of OX40 that are shorter or longer than a specific delineated domain can be included in a CAR, if desired. In some embodiments, a CAR can comprise a transmembrane domain derived from OX40. In some embodiments, the transmembrane domain of the CAR comprises the transmembrane region of OX40, or a fragment thereof. In some embodiments, the cytoplasmic domain of a domain and a transmembrane domain. In some embodiments, a CAR has an amino acid sequence comprising the transmembrane domain and the intracellular domain of ICOS and comprises amino acids 141 to 199 of ICOS. It is understood that sequences of ICOS that are shorter or longer than a specific delineated domain can be included in a CAR, if desired.

2B4. 2B4 (CD244) is a co-stimulatory receptor expressed on both NK cells and CD8+ T cells. It targets a non-MHC like molecule (CD48) expressed on hematopoietic cells, including B and T cells, as well as on activated monocytes and granulocytes. Activation of 2B4 by binding of its ligand on target cells leads to NK (or T cell) activation, and target killing. A 2B4 polypeptide can have an amino acid sequence corresponding to the sequence having Accession No: Q9BZW8.2 (NP_001160135.1; GI: 47605541), or fragments thereof. See GenBank NP_001160135.1 for reference to domains within 2B4, for example, signal peptide, amino acids 1 to 21; extracellular domain, amino acids 22 to 229; transmembrane domain, amino acids 230 to 250; intracellular domain, amino acids 251 to 370. In some embodiments, a CAR can comprise a transmembrane domain derived from 2B4. In some embodiments, the transmembrane domain of the CAR comprises the transmembrane region of 2B4, or a fragment thereof. In some embodiments, the cytoplasmic domain of a CAR can comprise a co-stimulatory domain derived from 2B4. In some embodiments, the co-stimulatory domain comprises the intracellular domain of 2B4, or a fragment thereof. In some embodiments, a CAR can comprise two domains derived from 2B4, a co-stimulatory signaling domain and a transmembrane domain. In some embodiments, a CAR has an amino acid sequence comprising the transmembrane domain and the intracellular domain of 2B4 and comprises amino acids 230 to 370 of 2B4. It is understood that sequences of 2B4 that are shorter or longer than a specific delineated domain can be included in a CAR, if desired.

CD27: CD27 (TNFRSF7) is a transmembrane receptor expressed on subsets of human CD8+ and CD4+ T-cells, NKT cells, NK cell subsets and hematopoietic progenitors and induced in FOXP3+CD4 T-cells and B cell subsets. Previously studies have found that CD27 can either actively provide costimulatory signals that improve human T-cell survival and anti-tumor activity in vivo. (See Song and Powell; *Oncoimmunology* 1, no. 4 (2012): 547-549). A CD27 polypeptide can have an amino acid sequence corresponding to the sequence having UniProtKB/Swiss-Prot No.: P26842.2 (GenBank NP_001233.1; GI: 269849546), or fragments thereof. See GenBank NP_001233 for reference to domains within CD27, for example, signal peptide, amino acids 1 to 19; extracellular domain, amino acids 20 to 191; transmembrane domain, amino acids 192 to 212; intracellular domain, amino acids 213 to 260. In some embodiments, a CAR can comprise a transmembrane domain derived from CD27. In some embodiments, the transmembrane domain of the CAR comprises the transmembrane region of CD27, or a fragment thereof. In some embodiments, the cytoplasmic domain of a CAR can comprise a co-stimulatory domain derived from CD27. In some embodiments, the co-stimulatory domain comprises the intracellular domain of CD27, or a fragment thereof. In some embodiments, a CAR can comprise two domains derived from CD27, a co-stimulatory signaling domain and a transmembrane domain. In some embodiments, a CAR has an amino acid sequence comprising the transmembrane domain and the intracellular domain of CD27 and comprises amino acids 192 to 260 of CD27. It is understood that sequences of CD27 that are shorter or longer than a specific delineated domain can be included in a CAR, if desired.

CD30: CD30 and its ligand (CD30L) are members of the tumor necrosis factor receptor (TNFR) and tumor necrosis factor (TNF) superfamilies, respectively. CD30, in many respects, behaves similarly to Ox40 and enhances proliferation and cytokine production induced by TCR stimulation. (Goronzy and Weyand, *Arthritis research & therapy* 10, no. S1 (2008): S3.) A CD30 polypeptide can have an amino acid sequence corresponding to the sequence having GenBank No.: AAA51947.1 (GenBank NP_001234.3; GI: 180096), or fragments thereof. See GenBank NP_001234.3 for reference to domains within CD30, for example, signal peptide, amino acids 1 to 18; extracellular domain, amino acids 19 to 385; transmembrane domain, amino acids 386 to 406; intracellular domain, amino acids 407 to 595. In some embodiments, a CAR can comprise a transmembrane domain derived from CD30. In some embodiments, the transmembrane domain of the CAR comprises the transmembrane region of CD30, or a fragment thereof. In some embodiments, the cytoplasmic domain of a CAR can comprise a co-stimulatory domain derived from CD30. In some embodiments, the co-stimulatory domain comprises the intracellular domain of CD30, or a fragment thereof. In some embodiments, a CAR can comprise two domains derived from CD30, a co-stimulatory signaling domain and a transmembrane domain. In some embodiments, a CAR has an amino acid sequence comprising the transmembrane domain and the intracellular domain of CD30 and comprises amino acids 386 to 595 of CD30. It is understood that sequences of CD30 that are shorter or longer than a specific delineated domain can be included in a CAR, if desired.

CD40: CD40 is a 48 kD transmembrane glycoprotein surface receptor that is a member of the Tumor Necrosis Factor Receptor superfamily (TNFRSF). Exemplary amino acid sequences of human CD40 are described (see, e.g., Accession: ALQ33424.1, GenBank NP_001241.1, GI: 957949089), CD40 was initially characterized as a co-stimulatory receptor expressed on APCs that played a central role in B and T cell activation. The ligand for CD40, CD154 (also known as TRAP, T-BAM, CD40 Ligand or CD40L) is a type II integral membrane protein. See GenBank NP_001241.1 for reference to domains within CD40, for example, signal peptide, amino acids 1 to 20; extracellular domain, amino acids 21 to 193; transmembrane domain, amino acids 194 to 215; intracellular domain, amino acids 216 to 277. In some embodiments, a CAR can comprise a transmembrane domain derived from CD40. In some embodiments, the transmembrane domain of the CAR comprises the transmembrane region of CD40, or a fragment thereof. In some embodiments, the cytoplasmic domain of a CAR can comprise a co-stimulatory domain derived from CD40. In some embodiments, the co-stimulatory domain comprises the intracellular domain of CD40, or a fragment thereof. In some embodiments, a CAR can comprise two domains derived from CD40, a co-stimulatory signaling domain and a transmembrane domain. In some embodiments, a CAR has an amino acid sequence comprising the transmembrane domain and the intracellular domain of CD40 and comprises amino acids 194 to 277 of CD40. It is understood that sequences of CD40 that are shorter or longer than a specific delineated domain can be included in a CAR, if desired.

CD2 The engagement of the CD2 molecule by its ligand CD58 co-stimulates proliferation, cytokine production, and effector function in this T cells, especially the CD28-deficient T cells subset. CD58 is broadly expressed on APCs including dendritic cells. Engagement of CD2 amplifies TCR signals in $CD28^-CD8^+$ T cells, demonstrating that the CD2-CD58 interaction has a genuine costimulatory effect. CD2 signals could promote the control of viral infection by $CD28^-CD8^+$ T cells, but they could also contribute to the continuous expansion of $CD28^-CD8^+$ T cells during chronic stimulation by persistent Ag. (Judith Leitner J et al., *Immunol*, 2015, 195 (2) 477-487). A CD2 polypeptide can have an amino acid sequence corresponding to the sequence having Accession: NP_001758.2 GI: 156071472, or fragments thereof. See GenBank NP_001758.2 for reference to domains within CD2, for example, signal peptide, amino acids 1 to 24; extracellular domain, amino acids 25 to 209; transmembrane domain, amino acids 210 to 235; intracellular domain, amino acids 236 to 351. In some embodiments, a CAR can comprise a transmembrane domain derived from CD2. In some embodiments, the transmembrane domain of the CAR comprises the transmembrane region of CD2, or a fragment thereof. In some embodiments, the cytoplasmic domain of a CAR can comprise a co-stimulatory domain derived from CD2. In some embodiments, the co-stimulatory domain comprises the intracellular domain of CD2, or a fragment thereof. In some embodiments, a CAR can comprise two domains derived from CD2, a co-stimulatory domain and a transmembrane domain. In some embodiments, a CAR has an amino acid sequence comprising the transmembrane domain and the intracellular domain of CD2 and comprises amino acids 210 to 351 of CD2. It is understood that sequences of CD2 that are shorter or longer than a specific delineated domain can be included in a CAR, if desired.

LIGHT TNF superfamily member 14 (also known as LTg, CD258, HVEML, LIGHT) is a co-stimulatory receptor involved in cellular immune responses. LIGHT can function as a costimulatory factor for the activation of lymphoid cells and as a deterrent to infection by herpesvirus. LIGHT has been shown to stimulate the proliferation of T cells, and trigger apoptosis of various tumor cells. LIGHT is found in T cells and stromal cells. LIGHT is expressed on immature dendritic cells (DCs) generated from human PBMCs. Engagement of LIGHT co-stimulates human T cell proliferation, amplifies the NF-κB signaling pathway, and preferentially induces the production of IFN-γ, but not IL-4, in the presence of an antigenic signal. (Tamada K et al., *J Immunol*, 2000, 164 (8) 4105-4110). A LIGHT polypeptide can have an amino acid sequence corresponding to the sequence provided as Accession: NP_001363816.1 GI: 1777376047, or fragments thereof. See GenBank NP_001363816.1 for reference to domains within LIGHT, for example, intracellular domain, amino acids 1 to 37; transmembrane domain, amino acids 38 to 58; extracellular domain, amino acids 59 to 240. In some embodiments, the cytoplasmic domain of a CAR can comprise a co-stimulatory domain derived from LIGHT. In some embodiments, the co-stimulatory domain comprises the intracellular domain of LIGHT or a fragment thereof. It is understood that sequences of LIGHT that are shorter or longer than a specific delineated domain can be included in a CAR, if desired.

GITR TNF receptor superfamily member 18 (also known as TNFRSF18, AITR, GITR; CD357; GITR-D; ENERGEN) has been shown to have increased expression upon T-cell activation. Stimulation of T cells through GITR has been shown to enhance immunity to tumors and viral pathogens, and to exacerbate autoimmune disease. The effects of stimulation through GITR are generally thought to be caused by attenuation of the effector activity of immunosuppressive CD4+CD25+ regulatory T (TReg) cells. (Shevach, E. and Stephens, G. *Nat Rev Immunol* 6, 613-618 (2006)). A GITR polypeptide can have an amino acid sequence corresponding to the sequence provided as Accession: AAI52382.1, GenBank NP_004186.1, GI: 158931986, or fragments thereof. See GenBank NP_004186.1 for reference to domains within GITR, for example, signal peptide, amino acids 1 to 25; extracellular domain, amino acids 26 to 162; transmembrane domain, amino acids 163 to 183; intracellular domain, amino acids 184 to 241. In some embodiments, a CAR can comprise a transmembrane domain derived from GITR. In some embodiments, the transmembrane domain of the CAR comprises the transmembrane region of GITR, or a fragment thereof. In some embodiments, the cytoplasmic domain of a CAR can comprise a co-stimulatory domain derived from GITR. In some embodiments, the co-stimulatory domain comprises the intracellular domain of GITR, or a fragment thereof. In some embodiments, a CAR can comprise two domains derived from GITR, a co-stimulatory signaling domain and a transmembrane domain. In some embodiments, a CAR has an amino acid sequence comprising the transmembrane domain and the intracellular domain of GITR and comprises amino acids 163 to 241 of GITR. It is understood that sequences of GITR that are shorter or longer than a specific delineated domain can be included in a CAR, if desired.

DR3 TNF receptor superfamily member 25 (also known as DR3, TR3, DDR3, LARD, APO-3, TRAMP, WSL-1, GEF720, WSL-LR, PLEKHG5, or TNFRSF12) is expressed preferentially in the tissues enriched in lymphocytes, and it plays a role in regulating lymphocyte homeostasis. This receptor has been shown to stimulate NF-kappa B activity and regulate cell apoptosis. The signal transduction of this receptor is mediated by various death domain containing adaptor proteins. Multiple alternatively spliced transcript variants of this gene encoding distinct isoforms have been reported, most of which are potentially secreted molecules. The alternative splicing of this gene in B and T cells encounters a programmed change upon T-cell activation, which predominantly produces full-length, membrane bound isoforms, and is involved in controlling lymphocyte proliferation induced by T-cell activation. A DR3 polypeptide can have an amino acid sequence corresponding to the sequence provided as Accession: Accession: Accession: AAI17190.1, GenBank NP_003781.1 GI: 109658976, or fragments thereof. See GenBank NP_003781.1 for reference to domains within DR3, for example, signal peptide, amino acids 1 to 24; extracellular domain, amino acids 25 to 199; transmembrane domain, amino acids 200 to 220; intracellular domain, amino acids 221 to 417. In some embodiments, a CAR can comprise a transmembrane domain derived from DR3. In some embodiments, the transmembrane domain of the CAR comprises the transmembrane region of DR3, or a fragment thereof. In some embodiments, the cytoplasmic domain of a CAR can comprise a co-stimulatory domain derived from DR3. In some embodiments, the co-stimulatory domain comprises the intracellular domain of DR3, or a fragment thereof. In some embodiments, a CAR can comprise two domains derived from DR3, a co-stimulatory signaling domain and a transmembrane domain. In some embodiments, a CAR has an amino acid sequence comprising the transmembrane domain and the intracellular domain of DR3 and comprises amino acids 200 to 417 of DR3. It is understood that sequences of DR3 that are shorter or longer than a specific delineated domain can be included in a CAR, if desired.

CD43 CD43 (also known as SPN sialophorin, LSN, GALGP, GPL115) is a highly sialylated glycoprotein that functions in antigen-specific activation of T cells, and is found on the surface of thymocytes, T lymphocytes, monocytes, granulocytes, and some B lymphocytes. It contains a mucin-like extracellular domain, a transmembrane region and a carboxy-terminal intracellular region. In stimulated immune effector cells, proteolytic cleavage of the extracellular domain occurs in some cell types, releasing a soluble extracellular fragment. A CD43 polypeptide can have an amino acid sequence corresponding to the sequence provided as GenBank NP_003114.1, Accession: EAW80016.1 GI: 119600422, or fragments thereof. See GenBank NP_003114.1 for reference to domains within CD43, for example, signal peptide, amino acids 1 to 19; extracellular domain, amino acids 20 to 253; transmembrane domain, amino acids 254 to 276; intracellular domain, amino acids 277 to 400. In some embodiments, a CAR can comprise a transmembrane domain derived from CD43. In some embodiments, the transmembrane domain of the CAR comprises the transmembrane region of CD43, or a fragment thereof. In some embodiments, the cytoplasmic domain of a CAR can comprise a co-stimulatory domain derived from CD43. In some embodiments, the co-stimulatory domain comprises the intracellular domain of CD43, or a fragment thereof. In some embodiments, a CAR can comprise two domains derived from CD43, a co-stimulatory signaling domain and a transmembrane domain. In some embodiments, a CAR has an amino acid sequence comprising the transmembrane domain and the intracellular domain of CD43 and comprises amino acids 254 to 400 of CD43. It is understood that sequences of CD43 that are shorter or longer than a specific delineated domain can be included in a CAR, if desired.

CD4. Cluster of differentiation 4 (CD4), also referred to as T-cell surface glycoprotein CD4, is a glycoprotein found on the surface of immune cells such as T helper cells, monocytes, macrophages, and dendritic cells. In some embodiments, a CAR can comprise a transmembrane domain derived from CD4. CD4 exists in various isoforms. It is understood that any isoform can be selected to achieve a desired function. Exemplary isoforms include isoform 1 (NP_000607.1, GI:10835167), isoform 2 (NP_001181943.1, GI:303522479), isoform 3 (NP_001181944.1, GI:303522485; or NP_001181945.1, GI:303522491; or NP_001181946.1, GI:303522569). See GenBank NP_000607.1 for reference to domains within CD4, for example, signal peptide, amino acids 1 to 25; extracellular domain, amino acids 26 to 396; transmembrane domain amino acids, 397 to 418; intracellular domain, amino acids 419 to 458. In some embodiments, a CAR can comprise a transmembrane domain derived from CD4. In some embodiments, the transmembrane domain of the CAR comprises the transmembrane region of CD4, or a fragment thereof. It is understood that additional sequence of CD4 beyond the transmembrane domain of amino acids 397 to 418 can be included in a CAR, if desired. It is further understood that sequences of CD4 that are shorter or longer than a specific delineated domain can be included in a CAR, if desired.

CD8. Cluster of differentiation 8 (CD8) is a transmembrane glycoprotein that serves as a co-receptor for the T cell receptor (TCR). CD8 binds to a major histocompatibility complex (MHC) molecule and is specific for the class I MHC protein. In some embodiments, a CAR can comprise a transmembrane domain derived from CD8. A CD8 polypeptide can have an amino acid sequence corresponding to the sequence having GenBank No. NP_001139345.1 (GI: 225007536), as provided below, or fragments thereof. See GenBank NP_001139345.1 for reference to domains within CD8, for example, signal peptide, amino acids 1 to 21; extracellular domain, amino acids 22 to 182; transmembrane domain amino acids, 183 to 203; intracellular domain, amino acids 204 to 235. In some embodiments, a CAR can comprise a hinge domain derived from CD8. In some embodiments, the hinge domain can comprise amino acids 137 to 182 of the CD8 polypeptide provided below. In some embodiments, a CAR can comprise a transmembrane domain derived from CD8. In some embodiments, the transmembrane domain of the CAR comprises the transmembrane region of CD8 (e.g., amino acids 183 to 203 of the sequence below), or a fragment thereof. In another embodiment, a CAR can comprise amino acids 137 to 203 of the CD8 polypeptide provided below. In yet another embodiment, a CAR can comprise amino acids 137 to 209 of the CD8 polypeptide provided below. It is understood that additional sequence of CD8 beyond the hinge domain of amino acids 137 to 182 and the transmembrane domain of amino acids 183 to 203 can be included in a CAR, if desired. It is further understood that sequences of CD8 that are shorter or longer than a specific delineated domain can be included in a CAR, if desired.

```
                                                            (SEQ ID NO: 21)
  1    MALPVTALLL  PLALLLHAAR  PSQFRVSPLD  RTWNLGETVE  LKCQVLLSNP  TSGCSWLFQP

61    RGAAASPTFL  LYLSQNKPKA  AEGLDTQRFS  GKRLGDTFVL  TLSDFRRENE  GYYFCSALSN

121    SIMYFSHFVP  VFLPAKPTTT  PAPRPPTPAP  TIASQPLSLR  PEACRPAAGG  AVHTRGLDFA

181    CDIYIWAPLA  GTCGVLLLSL  VITLYCNHRN  RRRVCKCPRP  VVKSGDKPSL  SARYV
```

As such, for exemplary purposes, a CAR disclosed herein can comprise, from N-terminus to the C-terminus, an anti-mesothelin antibody or antigen-binding fragment (e.g., scFvs disclosed herein), a hinge (e.g., CD8 hinge or CD28 hinge), a transmembrane region (e.g., CD8 transmembrane region or CD28 transmembrane region), a costimulatory domain (e.g., the intracellular domain of 4-1BB, CD28, or both), and a signaling domain (e.g., the T cell signaling domain of CD3).

5.4 Polynucleotides and Vectors

Also provided herein are polynucleotides that encode a polypeptide (e.g., an anti-mesothelin antibody or antigen-binding fragment or a CAR that specifically binds mesothelin) described herein. The term "polynucleotide that encode a polypeptide" encompasses a polynucleotide which includes only coding sequences for the polypeptide as well as a polynucleotide which includes additional coding and/or non-coding sequences. The polynucleotides of the disclosure can be in the form of RNA or in the form of DNA. DNA can be cDNA, genomic DNA, or synthetic DNA, and can be double-stranded or single-stranded. Single stranded DNA can be the coding strand or non-coding (anti-sense) strand. The polynucleotides of the disclosure can be mRNA.

Expressly contemplated herein are polynucleotides encode any anti-mesothelin antibody or antigen-binding fragment disclosed herein. For illustrative purposes, in some embodiments, the polynucleotides provided herein encode an anti-mesothelin antibody or antigen-binding fragment comprising (a) a VL comprising (1) a VL CDR1 having an amino acid sequence of SEQ ID NO: 1; (2) a VL CDR2 having an amino acid sequence of SEQ ID NO: 2; and (3) a VL CDR3 having an amino acid sequence of SEQ ID NO: 3; or a variant thereof having up to about 5 amino acid substitutions, additions, and/or deletions in the VL CDRs; and/or (b) a VH comprising (1) a VH CDR1 having an amino acid sequence of SEQ ID NO: 4; (2) a VH CDR2 having an amino acid sequence of SEQ ID NO: 5; and (3) a VH CDR3 having an amino acid sequence of SEQ ID NO: 6; or a variant thereof having up to about 5 amino acid substitutions, additions, and/or deletions in the VH CDRs. In some embodiments, the polynucleotides provided herein encode an anti-mesothelin antibody or antigen-binding fragment comprising (a) a VL having at least 85%, at least 90%, at least 95%, at least 98%, or 100% sequence identity to an amino acid sequence of SEQ ID NO: 7; and/or (b) a VH having at least 85%, at least 90%, at least 95%, at least 98%, or 100% sequence identity to an amino acid sequence of SEQ ID NO: 8. The polynucleotides can be in the form of DNA. The polynucleotides can be in the form of mRNA.

In some embodiments, the polynucleotides provided herein encode an anti-mesothelin antibody or antigen-binding fragment disclosed herein comprising a VL and a VH, wherein the VL comprises VL CDR1, CDR2 and CDR3 and the VH comprises VH CDR1, CDR2 and CDR3, and wherein the VL CDR1, VL CDR2, VL CDR3, VH CDR1, VH CDR2 and VH CDR3 have the amino acid sequences of SEQ ID NOs: 1, 2, 3, 4, 5, and 6, respectively, or a variant thereof having up to about 5 amino acid substitutions, additions, and/or deletions in the VL CDRs. The polynucleotides can be in the form of DNA. The polynucleotides can be in the form of mRNA.

In some embodiments, the polynucleotides provided herein encode an anti-mesothelin antibody or antigen-binding fragment disclosed herein comprising a VL and a VH, wherein the VL and VH have the amino acid sequences of SEQ ID NOs: 7 and 8, respectively. The polynucleotides can be in the form of DNA. The polynucleotides can be in the form of mRNA.

In some embodiments, the VL and VH are connected by a linker. The linker can be a flexible linker or a rigid linker. In some embodiments, the linker has the amino acid sequence of (GGGGS)n, n=1, 2, 3, 4, or 5. For example, the linker may have the amino acid sequence of GGGGS (SEQ ID NO: 14). In some embodiments, the linker has the amino acid sequence of (EAAAK)n, n=1, 2, 3, 4, or 5. For example, the linker may have the amino acid sequence of EAAAK (SEQ ID NO: 15). In some embodiments, the linker has the amino acid sequence of (PA)nP, n=1, 2, 3, 4, or 5. For example, the linker may have the amino acid sequence of PAP (SEQ ID NO: 16). In some embodiments, the linker has the amino acid sequence of GGGGSGGGGSGGGGS (SEQ ID NO: 17).

In some embodiments, the polynucleotides provided herein encode an anti-mesothelin antibody or antigen-binding fragment disclosed herein comprising a VL having at least 85%, at least 90%, at least 95%, at least 98%, or 100% sequence identity to an amino acid sequence of SEQ ID NO: 7.

In some embodiments, the polynucleotides provided herein have a nucleotide sequence at least 80%, at least 85%, at least 90%, at least 95%, at least 96%, at least 97%, at least 98%, at least 99%, or 100% identical to a nucleotide sequence of SEQ ID NOs: 9. Also provided is a polynucleotide that hybridizes to a polynucleotide having a nucleotide sequence of SEQ ID NO: 9. In some embodiments, the hybridization is under conditions of high stringency as is known to those skilled in the art. The polynucleotides can be in the form of DNA. The polynucleotides can be in the form of mRNA.

In some embodiments, the polynucleotides provided herein encode an anti-mesothelin antibody or antigen-binding fragment disclosed herein comprising a VH having at least 85%, at least 90%, at least 95%, at least 98%, or 100% sequence identity to an amino acid sequence of SEQ ID NO: 8.

In some embodiments, the polynucleotides provided herein have a nucleotide sequence at least 80%, at least 85%, at least 90%, at least 95%, at least 96%, at least 97%, at least 98%, at least 99%, or 100% identical to a nucleotide sequence of SEQ ID NO: 10. Also provided is a polynucleotide that hybridizes to a polynucleotide having a nucleotide sequence of SEQ ID NO: 10. In some embodiments, the hybridization is under conditions of high stringency as is known to those skilled in the art. The polynucleotides can be in the form of DNA. The polynucleotides can be in the form of mRNA.

The present disclosure also provides variants of the polynucleotides described herein, wherein the variants encode, for example, fragments, analogs, and/or derivatives of an anti-mesothelin antibody or antigen-binding fragment disclosed herein. In some embodiments, the present disclosure provides a polynucleotide having a nucleotide sequence at least about 80% identical, at least about 85% identical, at least about 90% identical, at least about 95% identical, at least about 96% identical, at least about 97% identical, at least about 98% identical, or at least about 99% identical to a polynucleotide sequence encoding an anti-mesothelin antibody or antigen-binding fragment described herein. In some embodiments, the present disclosure provides a polynucleotide having a nucleotide sequence at least about 80% identical, at least about 85% identical, at least about 90% identical, at least about 95% identical, at least about 96% identical, at least about 97% identical, at least about 98% identical, or at least about 99% identical to a polynucleotide sequence encoding an anti-mesothelin antibody or antigen-binding fragment described herein.

In some embodiments, the polynucleotides provided herein encode an anti-mesothelin antibody or antigen-binding fragment that is the scFv designated as M12. In some embodiments, the polynucleotides provided herein encode an anti-mesothelin antibody or antigen-binding fragment having the amino acid sequence of SEQ ID NO:11.

Provided herein are also polynucleotides that encode the TCRs disclosed herein. In some embodiments, provided herein are polynucleotides that encode a TCR α chain that comprises an anti-mesothelin antibody or antigen-binding fragment described herein. In some embodiments, provided herein are polynucleotides that encode a TCR β chain that comprises an anti-mesothelin antibody or antigen-binding fragment described herein. In some embodiments, provided herein are polynucleotides that encode a TCR γ chain that comprises an anti-mesothelin antibody or antigen-binding fragment described herein. In some embodiments, provided herein are polynucleotides that encode a TCR δ chain that comprises an anti-mesothelin antibody or antigen-binding fragment described herein. The polynucleotides can be in the form of DNA. The polynucleotides can be in the form of mRNA.

Provided herein are also polynucleotides that encode the CARs disclosed herein. In some embodiments, provided herein are polynucleotides encoding CARs that specifically binds mesothelin, comprising, from N-terminus to C-terminus: (a) a mesothelin-binding domain comprising an anti-mesothelin antibody or antigen-binding fragment provided herein, (b) a transmembrane domain, and (c) a cytoplasmic domain. The transmembrane and cytoplasmic domains can be any transmembrane and cytoplasmic domains disclosed herein. For illustrative purposes, provided herein are, for example, polynucleotides that encode the CARs that specifically binds mesothelin, comprising, from N-terminus to C-terminus: (a) a mesothelin-binding domain comprising an anti-mesothelin scFv provided herein, (b) a transmembrane domain comprising the CD28 transmembrane region, and (c) a cytoplasmic domain comprising a CD3ζ signaling domain and a 4-1BB co-stimulatory domain. The polynucleotides can be in the form of DNA. The polynucleotides can be in the form of mRNA.

In some embodiments, the polynucleotides provided herein encode an anti-mesothelin CAR having at least 85%, at least 90%, at least 95%, at least 98%, or 100% sequence identity to an amino acid sequence of SEQ ID NO:12.

In some embodiments, the polynucleotides provided herein have a nucleotide sequence at least 80%, at least 85%, at least 90%, at least 95%, at least 96%, at least 97%, at least 98%, at least 99%, or 100% identical to a nucleotide sequence of SEQ ID NO:13.

As used herein, the phrase "a polynucleotide having a nucleotide sequence at least about 95% identical to a polynucleotide sequence" means that the nucleotide sequence of the polynucleotide is identical to a reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (e.g., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, a polynucleotide comprises the coding sequence for a polypeptide (e.g., a CAR or an antibody) fused in the same reading frame to a polynucleotide which aids in expression and secretion of a polypeptide from a host cell (e.g., a leader sequence which functions as a secretory sequence for controlling transport of a polypeptide). The polypeptide can have the leader sequence cleaved by the host cell to form a "mature" form of the polypeptide.

In some embodiments, a polynucleotide comprises the coding sequence for a polypeptide (e.g., a CAR or an antibody) fused in the same reading frame to a marker or tag sequence. For example, in some embodiments, a marker sequence is a hexa-histidine tag (HIS-tag) that allows for efficient purification of the polypeptide fused to the marker. In some embodiments, a marker sequence is a hemagglutinin (HA) tag derived from the influenza hemagglutinin protein when a mammalian host (e.g., COS-7 cells) is used. In some embodiments, the marker sequence is a FLAG™ tag. In some embodiments, a marker can be used in conjunction with other markers or tags.

In some embodiments, a polynucleotide is isolated. In some embodiments, a polynucleotide is substantially pure.

Vectors and cells comprising the polynucleotides described herein are also provided. In some embodiments, provided herein are vectors comprising a polynucleotide provided herein. The vectors can be expression vectors. In some embodiments, vectors provided herein comprise a polynucleotide encoding an anti-mesothelin antibody or antigen-binding fragment described herein. In some embodiments, vectors provided herein comprise a polynucleotide encoding a polypeptide that is part of an anti-mesothelin antibody or antigen-binding fragment described herein. In some embodiments, vectors provided herein comprise a polynucleotide encoding a CAR or TCR described herein. In some embodiments, vectors provided herein comprise a polynucleotide encoding a polypeptide that is part of a CAR or TCR described herein.

In some embodiments, provided herein are recombinant expression vectors, which can be used to amplify and express a polynucleotide encoding a CAR/TCR described herein that specifically binds mesothelin or an anti-mesothelin antibody or antigen-binding fragment described herein. For example, a recombinant expression vector can be a replicable DNA construct that includes synthetic or cDNA-derived DNA fragments encoding a CAR/TCR or a polypeptide chain of an anti-mesothelin antibody, operatively linked to suitable transcriptional and/or translational regulatory elements derived from mammalian, microbial, viral or insect genes. In some embodiments, a viral vector is used. DNA regions are "operatively linked" when they are functionally related to each other. For example, a promoter is operatively linked to a coding sequence if it controls the transcription of the sequence; or a ribosome binding site is operatively linked to a coding sequence if it is positioned so as to permit translation. In some embodiments, structural elements intended for use in certain expression systems include a leader sequence enabling extracellular secretion of translated protein by a host cell. In some embodiments, in situations where recombinant protein is expressed without a leader or transport sequence, a polypeptide can include an N-terminal methionine residue.

A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

In some embodiments, a CAR/TCR described herein or an anti-mesothelin antibody or antigen-binding fragment described herein is expressed from one or more vectors.

Suitable host cells for expression include prokaryotes, yeast cells, insect cells, or higher eukaryotic cells under the control of appropriate promoters. Appropriate cloning and expression vectors for use with bacterial, fungal, yeast, and mammalian cellular hosts, as well as methods of protein production, including antibody production are well-known in the art.

Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

The present disclosure also provides host cells comprising the polypeptides described herein, polynucleotides encoding polypeptides described herein, or vectors comprising such polynucleotides. In some embodiments, provided herein are host cells comprising a vector comprising a polynucleotide disclosed herein. In some embodiments, host cells provided herein comprise a vector comprising a polynucleotide encoding an anti-mesothelin antibody or antigen-binding fragment described herein. In some embodiments, host cells provided herein comprise a vector comprising a polynucleotide encoding a polypeptide that is part of an anti-mesothelin antibody or antigen-binding fragment described herein. In some embodiments, host cells provided herein comprise a polynucleotide encoding an anti-mesothelin antibody or antigen-binding fragment described herein. In some embodiments, the cells produce the anti-mesothelin antibodies or antigen-binding fragments described herein. In some embodiments, host cells provided herein comprise a vector comprising a polynucleotide encoding a CAR or TCR described herein. In some embodiments, host cells provided herein comprise a vector comprising a polynucleotide molecule encoding a polypeptide that is part of a CAR or TCR described herein. In some embodiments, host cells provided herein comprise a polynucleotide encoding a CAR or TCR described herein. In some embodiments, the host cells produce the mesothelin CARs or TCR described herein.

5.5 Cells

Provided herein are cells comprising the polynucleotides disclosed herein. In some embodiments, provided herein are cells comprising a polynucleotide that encodes a polypeptide disclosed herein. In some embodiments, provided herein are cells comprising a vector having a polynucleotide disclosed herein. In some embodiments, provided herein are cells recombinantly expressing a polypeptide disclosed herein. The polypeptide can be an anti-mesothelin antibody or antigen-binding fragment. The polypeptide can be mesothelin CAR. The polypeptide can be a mesothelin TCR.

In some embodiments, cells provided herein are immune effector cells. In some embodiments, the immune effector cells are selected from the group consisting of T cells, B cell, natural killer (NK) cells, NKT cells, macrophages, granulocytes, neutrophils, eosinophils, mast cells, and basophils. In some embodiments, the immune effector cells provided herein are selected from the group consisting of T cells, NK cells, NKT cells, macrophages, neutrophils, and granulocytes. In some embodiments, the immune effector cell provided herein is a T cell. In some embodiments, the immune effector cell provided herein is an NK cell. In some embodiments, the immune effector cell provided herein is an NKT cell. In some embodiments, the immune effector cell provided herein is a macrophage. In some embodiments, the immune effector cell provided herein is a neutrophil. In some embodiments, the immune effector cell provided herein is a granulocyte.

In some embodiments, the immune effector cells provided herein can be genetically engineered. In some embodiments, the genetically engineered immune effector cells provided herein are isolated. In some embodiments, the genetically engineered immune effector cells provided herein are substantially pure.

As such, in some embodiments, provided herein are immune effector cells recombinantly expressing a polypeptide (e.g., an antibody or a CAR) disclosed herein. Provided herein are also immune effector cells (e.g., T cells) comprising a polynucleotide encoding a polypeptide (e.g., an antibody or a CAR) disclosed herein, or a vector having a polynucleotide disclosed herein. In some embodiments, provided herein are immune effector cells (e.g., T cells) comprising a polynucleotide that encodes an anti-mesothelin antibody or antigen-binding fragment disclosed herein. In some embodiments, provided herein are immune effector cells (e.g., T cells) recombinantly expressing an anti-mesothelin antibody or antigen-binding fragment disclosed herein. In some embodiments, provided herein are immune effector cells comprising a polynucleotide that encodes a mesothelin CAR disclosed herein. In some embodiments, provided herein are immune effector cells (e.g., T cells) recombinantly expressing a mesothelin CAR disclosed herein (e.g., mesothelin CART cell). In some embodiments, provided herein are immune effector cells comprising a polynucleotide that encodes a mesothelin TCR disclosed herein. In some embodiments, provided herein are immune effector cells (e.g., T cells) recombinantly expressing a mesothelin TCR disclosed herein (e.g., mesothelin TCRT cell).

In some embodiments, the immune effector cell provided herein is a T cell. The T cell can be a cytotoxic T cell, a helper T cell, or a gamma delta T, a CD4+/CD8+ double positive T cell, a CD4+ T cell, a CD8+ T cell, a CD4/CD8 double negative T cell, a CD3+ T cell, a naive T cell, an effector T cell, a cytotoxic T cell, a helper T cell, a memory T cell, a regulator T cell, a Th0 cell, a Th1 cell, a Th2 cell, a Th3 (Treg) cell, a Th9 cell, a Th17 cell, a Th$\alpha\beta$ helper cell, a Tfh cell, a stem memory TSCM cell, a central memory TCM cell, an effector memory TEM cell, an effector memory TEMRA cell, or a gamma delta T cell. In some embodiments, the T cell is a cytotoxic T cell. In some embodiments, the T cell is genetically engineered. In some embodiments, the T cells provided herein are isolated. In some embodiments, the T cells provided herein are substantially pure.

In some embodiments, genetically engineered cells provided herein are derived from cells isolated from a subject. As used herein, a genetically engineered cell that is "derived from" a source cell means that the genetically engineered cell is obtained by taking the source cell and genetically manipulating the source cell. The source cell can be from a natural source. For example, the source cell can be a primary cell isolated from a subject. The subject can be an animal or a human. The source cell can also be a cell that has undergone passages or genetically manipulation in vitro.

In some embodiments, genetically engineered cells provided herein are derived from cells isolated from a human. Immune effector cells (e.g., T cells) can be obtained from many sources, including peripheral blood mononuclear cells, bone marrow, lymph node tissue, cord blood, thymus tissue, tissue from a site of infection, ascites, pleural effusion, spleen tissue, and tumors. In certain embodiments, T cell lines available in the art can be used. In some embodiments, genetically engineered cells provided herein are derived from cells isolated from peripheral blood. In some embodiments, genetically engineered cells provided herein are derived from cells isolated from bone marrow. In some embodiments, genetically engineered cells provided herein are derived from cells isolated from peripheral blood mononuclear cells (PBMC).

In some embodiments, genetically engineered cells provided herein are derived from cells differentiated in vitro from a stem or progenitor cell. In some embodiments, the stem or progenitor cell is selected from the group consisting of a T cell progenitor cell, a hematopoietic stem and progenitor cell, a hematopoietic multipotent progenitor cell, an embryonic stem cell, and an induced pluripotent cell. In some embodiments, genetically engineered cells provided herein are derived from cells differentiated in vitro from a T cell progenitor cell. In some embodiments, genetically engineered cells provided herein are derived from cells differentiated in vitro from a hematopoietic stem and progenitor cell. In some embodiments, genetically engineered cells provided herein are derived from cells differentiated in vitro from a hematopoietic multipotent progenitor cell. In some embodiments, genetically engineered cells provided herein are derived from cells differentiated in vitro from an embryonic stem cell. In some embodiments, genetically engineered cells provided herein are derived from cells differentiated in vitro from an induced pluripotent cell.

In some embodiments, provided herein are a population of cells comprising a cell disclosed herein. The cells disclosed herein can comprise a polynucleotide that encodes a polypeptide disclosed herein or recombinantly express a polypeptide disclosed herein. The polypeptide can be an anti-mesothelin antibody or antigen-binding fragment, a mesothelin CAR, or a mesothelin TCR. The population of cells can be a homogenous population of cells. The population of cells can be a heterogeneous population of cells. In some embodiments, the population of cells can be a heterogeneous population of cells comprising any combination of the cells disclosed herein. In some embodiments, the population of cells are derived from peripheral blood mononuclear cells (PBMC), peripheral blood leukocytes (PBL), tumor infiltrating lymphocytes (TIL), cytokine-induced killer cells (CIK), lymphokine-activated killer cells (LAK), or marrow infiltrate lymphocytes (MILs). In some embodiments, the population of cells provided herein are derived from PBMC. In some embodiments, the population of cells provided herein are derived from PBL. In some embodiments, the population of cells provided herein are derived from TIL. In some embodiments, the population of cells provided herein are derived from CIK. In some embodiments, the population of cells provided herein are derived from LAK. In some embodiments, the population of cells provided herein are derived from MILS. The population of cells can be genetically engineered to recombinantly expressing a polypeptide (e.g., an antibody or a CAR) disclosed herein. In some embodiments, provided herein are population of cells comprising a polynucleotide encoding a polypeptide (e.g., an antibody or a CAR) disclosed herein, or a vector having a polynucleotide disclosed herein. In some embodiments, provided herein are population of cells comprising a polynucleotide that encodes an anti-mesothelin antibody or antigen-binding fragment disclosed herein. In some embodiments, provided herein are population of cells recombinantly expressing an anti-mesothelin antibody or antigen-binding fragment disclosed herein. In some embodiments, provided herein are population of cells comprising a polynucleotide that encodes a mesothelin CAR disclosed herein. In some embodiments, provided herein are population of cells recombinantly expressing a mesothelin CAR disclosed herein (e.g., mesothelin CART cell). In some embodiments, provided herein are population of cells comprising a polynucleotide that encodes a mesothelin TCR disclosed herein. In some embodiments, provided herein are population of cells recombinantly expressing a mesothelin TCR disclosed herein (e.g., mesothelin TCRT cell).

5.6 Pharmaceutical Compositions

Provided herein are also pharmaceutical compositions comprising the anti-mesothelin antibodies or antigen-binding fragments disclosed herein. Provided herein are also pharmaceutical compositions comprising the genetically engineered immune effector cells disclosed herein. In some embodiments, the pharmaceutical composition comprises a therapeutically effective amount of the anti-mesothelin antibodies or antigen-binding fragments disclosed herein and a pharmaceutically acceptable carrier. In some embodiments, the pharmaceutical composition comprises a therapeutically effective amount of genetically engineered cells disclosed herein and a pharmaceutically acceptable carrier. In some embodiments, the pharmaceutical compositions are useful in immunotherapy. In some embodiments, the pharmaceutical compositions are useful in immuno-oncology. In some embodiments, the pharmaceutical compositions are useful in inhibiting tumor growth in a subject (e.g., a human patient). In some embodiments, the pharmaceutical compositions are useful in treating cancer in a subject (e.g., a human patient).

In some embodiments, the pharmaceutical compositions provided herein comprise anti-mesothelin antibodies or antigen-binding fragments provided herein. The anti-mesothelin antibodies or antigen-binding fragments can be present at various concentrations. In some embodiments, the pharmaceutical compositions provided herein comprise soluble anti-mesothelin antibodies or antigen-binding fragments provided herein at 1-1000 mg/ml. In some embodiments, the pharmaceutical compositions comprise soluble anti-mesothelin antibodies or antigen-binding fragments provided herein at 10-500 mg/ml, 10-400 mg/ml, 10-300 mg/ml, 10-200 mg/ml, 10-100 mg/ml, 20-100 mg/ml, or 50-100 mg/ml. In some embodiments, the pharmaceutical compositions provided herein comprise anti-mesothelin antibodies or antigen-binding fragments provided herein at about 10 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 120 mg/ml, about 150 mg/ml, about 180 mg/ml, about 200 mg/ml, about 300 mg/ml, about 500 mg/ml, about 800 mg/ml, or about 1000 mg/ml.

The pharmaceutical compositions comprising genetically engineered immune effector cells (e.g., T cells) disclosed herein can comprise a purified population of cells. Those skilled in the art can readily determine the percentage of cells in a cell population using various well-known methods, as described herein. The ranges of purity in cell populations comprising genetically engineered cells provided herein can be from about 20% to about 25%, from about 25% to about 30%, from about 30% to about 35%, from about 35% to about 40%, from about 40% to about 45%, from about 45% to about 50%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. In some embodiments, the ranges of purity in cell populations comprising immune effector cells provided herein can be from about 20% to about 30%, from about 20% to about 50%, from about 20% to about 80%, from about 20% to about 100%, from about 50% to about 80%, or from about 50% to about 100%. Dosages can be readily adjusted by those skilled in the art; for example, a decrease in purity may require an increase in dosage.

Provided herein are also kits for preparation of pharmaceutical compositions having the anti-mesothelin antibodies or antigen-binding fragments disclosed herein. In some embodiments, the kit comprises the anti-mesothelin antibodies or antigen-binding fragments disclosed herein and a pharmaceutically acceptable carrier in one or more containers. In another embodiment, the kits can comprise anti-mesothelin antibodies or antigen-binding fragments disclosed herein for administration to a subject. In specific embodiments, the kits comprise instructions regarding the preparation and/or administration of the anti-mesothelin antibodies or antigen-binding fragments.

Provided herein are also kits for preparation of immune effector cells (e.g., T cells) disclosed herein. In some embodiments, the kits comprise one or more vectors for generating a genetically engineered cell, such as a T cell, that expresses the anti-mesothelin antibodies or antigen-binding fragments disclosed herein. The kits can be used to generate genetically engineered immune effector cells (e.g., T cells) from autologous or non-autologous cells to be administered to a compatible subject. In another embodiment, the kits can comprise immune effector cells disclosed herein for administration to a subject. In specific embodiments, the kits comprise the immune effector cells disclosed herein in one or more containers. In specific embodiments, the kits comprise instructions regarding the preparation and/or administration of the immune effector cells.

In some embodiments, provided herein is a pharmaceutical composition comprising anti-mesothelin antibodies or antigen-binding fragments or cells provided herein wherein the composition is suitable for local administration. In some embodiments, local administration comprises intratumoral injection, peritumoral injection, juxtatumoral injection, intralesional injection and/or injection into a tumor draining lymph node, or essentially any tumor-targeted injection where the antitumor agent is expected to leak into primary lymph nodes adjacent to targeted solid tumor.

Pharmaceutically acceptable carriers that can be used in compositions provided herein include any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). Depending on the route of administration, the active ingredient (i.e., anti-mesothelin antibodies or antigen-binding fragments or immune effector cells provided herein), can be coated in a material to protect the active ingredient from the action of acids and other natural conditions that can inactivate the active ingredient.

Provided herein are also pharmaceutical compositions or formulations that improve the stability of the anti-mesothelin antibodies or antigen-binding fragments to allow for their long-term storage. In some embodiments, the pharmaceutical composition or formulation disclosed herein comprises: (a) anti-mesothelin antibodies or antigen-binding fragments disclosed herein; (b) a buffering agent; (c) a stabilizing agent; (d) a salt; (e) a bulking agent; and/or (f) a surfactant. In some embodiments, the pharmaceutical composition or formulation is stable for at least 1 month, at least 2 months, at least 3 months, at least 6 months, at least 1 year, at least 2 years, at least 3 years, at least 5 years or more. In some embodiments, the pharmaceutical composition or formulation is stable when stored at 4° C., 25° C., or 40° C.

Buffering agents useful in the pharmaceutical compositions or formulations disclosed herein can be a weak acid or base used to maintain the acidity (pH) of a solution near a chosen value after the addition of another acid or base. Suitable buffering agents can maximize the stability of the pharmaceutical formulations by maintaining pH control of the formulation. Suitable buffering agents can also ensure physiological compatibility or optimize solubility. Rheology, viscosity and other properties can also depend on the pH of the formulation. Common buffering agents include, but are not limited to, histidine, citrate, succinate, acetate and phosphate. In some embodiments, a buffering agent comprises histidine (e.g., L-histidine) with isotonicity agents and potentially pH adjustment with an acid or a base known in the art. In certain embodiments, the buffering agent is L-histidine. In certain embodiments, the pH of the formulation is maintained between about 2 and about 10, or between about 4 and about 8.

Stabilizing agents are added to a pharmaceutical product to stabilize that product. Such agents can stabilize proteins in different ways. Common stabilizing agents include, but are not limited to, amino acids such as glycine, alanine, lysine, arginine, or threonine, carbohydrates such as glucose, sucrose, trehalose, raffinose, or maltose, polyols such as glycerol, mannitol, sorbitol, cyclodextrins or destrans of any kind and molecular weight, or PEG. In some embodiments, the stabilizing agent is chosen to maximize the stability of FIX polypeptide in lyophilized preparations. In certain embodiments, the stabilizing agent is sucrose and/or arginine.

Bulking agents can be added to a pharmaceutical composition or formulation to add volume and mass to the product, thereby facilitating precise metering and handling thereof. Common bulking agents include, but are not limited to, lactose, sucrose, glucose, mannitol, sorbitol, calcium carbonate, or magnesium stearate.

Surfactants are amphipathic substances with lyophilic and lyophobic groups. A surfactant can be anionic, cationic, zwitterionic, or nonionic. Examples of nonionic surfactants include, but are not limited to, alkyl ethoxylate, nonylphenol ethoxylate, amine ethoxylate, polyethylene oxide, polypropylene oxide, fatty alcohols such as cetyl alcohol or oleyl alcohol, cocamide MEA, cocamide DEA, polysorbates, or dodecyl dimethylamine oxide. In some embodiments, the surfactant is polysorbate 20 or polysorbate 80.

The pharmaceutical compositions disclosed herein can further comprise one or more of a buffer system, a preservative, a tonicity agent, a chelating agent, a stabilizer and/or a surfactant, as well as various combinations thereof. The use of preservatives, isotonic agents, chelating agents, stabilizers and surfactants in pharmaceutical compositions is well-known to the skilled person. Reference may be made to *Remington: The Science and Practice of Pharmacy*, 19$^{th}$ edition, 1995.

In some embodiments, the pharmaceutical composition is an aqueous formulation. Such a formulation is typically a solution or a suspension, but can also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In some embodiments, the pharmaceutical compositions disclosed herein are freeze-dried, to which the physician or the patient adds solvents and/or diluents prior to use.

Pharmaceutical compositions disclosed herein can also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that can be employed in the pharmaceutical compositions or formulations described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition or formulation can comprise a preservative or can be devoid of a preservative. Supplementary active compounds can be incorporated into the compositions.

Pharmaceutical compositions or formulations typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, the compositions can include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

The amount of active ingredient which can be combined with a carrier material in the pharmaceutical compositions or formulations disclosed herein can vary. In some embodiments, the amount of active ingredient which can be combined with a carrier material is the amount that produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

The pharmaceutical compositions disclosed herein can be prepared with carriers that protect the active ingredient against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and poly lactic acid. Many methods for the preparation of such formulations are patented or generally known to those skilled in the art. See. e.g., *Sustained and Controlled Release Drug Delivery Systems*, J. R. Robinson, ed., Marcel Dekker, Inc., New York, 1978.

In some embodiments, the anti-mesothelin antibodies or antigen-binding fragments or immune effector cells (e.g., T cells) described herein can be formulated to ensure proper distribution in vivo. For example, the blood-brain barrier (BBB) excludes many highly hydrophilic compounds. To ensure that the activate ingredient described herein cross the BBB (if desired, e.g., for brain cancers), they can be formulated, for example, in liposomes. For methods of manufacturing liposomes, see, e.g., U.S. Pat. Nos. 4,522,811; 5,374,548; and 5,399,331. The liposomes can comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al) mannosides (Umezawa et al, (1988) *Biochem. Biophys. Res. Commun.* 153: 1038); antibodies (P. G. Bloeman et al. (1995) *FEBS Lett.* 357: 140; M. Owais et al. (1995) *Antimicrob. Agents Chemother.* 39: 180); surfactant protein A receptor (Briscoe et al. (1995) *Am. J. Physiol.* 1233: 134); p 120 (Schreier et al. (1994) *J. Biol. Chem.* 269:9090); see also K. Keinanen; M. L. Laukkanen (1994) *FEBS Lett.* 346: 123; J. J. Killion; I. J. Fidler (1994) *Immunomethods* 4:273.

5.7 Methods and Uses

The present disclosure also provides methods of uses of the anti-mesothelin antibodies or antigen-binding fragments, mesothelin CARs, mesothelin TCRs, polynucleotides encoding such anti-mesothelin antibodies or antigen-binding fragments and mesothelin CARs/TCRs, vectors comprising such polynucleotides, mesothelin CAR/TCR-expressing cells or pharmaceutical compositions having such cells disclosed herein in treating cancer. Without being bound by theory, the anti-mesothelin antibodies or antigen-binding fragments and the mesothelin CAR/TCR-expressing cells disclosed herein can specifically target mesothelin-expressing cancer cells in vivo, thereby delivering their therapeutic effect of eliminating, lysing and/or killing cancer cells. In some embodiments, the methods include administering a therapeutically effective amount of the anti-mesothelin antibodies or antigen-binding fragments disclosed herein to a subject in need thereof. In some embodiments, the methods include administering a therapeutically effective amount of mesothelin CAR-expressing immune effector cells disclosed herein to a subject in need thereof. In one embodiment, the methods can include administering a therapeutically effective amount of mesothelin CARTs disclosed herein to a subject in need thereof.

In some embodiments, provided herein are methods of treating tumor or cancer in a subject in need thereof, comprising administering to the subject a therapeutically effective amount of the anti-mesothelin antibodies or antigen-binding fragments disclosed herein. In some embodiments, provided herein are uses of the anti-mesothelin antibodies or antigen-binding fragments disclosed herein in the treatment of tumor or cancer. In some embodiments, provided herein are uses of the anti-mesothelin antibodies or antigen-binding fragments provided herein for the preparation of a medicament for the treatment of tumor or cancer.

In some embodiments, provided herein are methods of treating tumor or cancer in a subject in need thereof, comprising administering to the subject a therapeutically effective amount of the immune effector cells (e.g., mesothelin CARTs) disclosed herein. In some embodiments, provided herein are uses of the immune effector cells disclosed herein (e.g., mesothelin CARTs) in treatment of tumor or cancer. In some embodiments, provided herein are uses of the immune effector cells (e.g., mesothelin CARTs) provided herein for the preparation of a medicament for the treatment of tumor or cancer. In some embodiments, a population of cells comprising the immune effector cell disclosed herein is used in the treatment. The population of cells can be homogenous. The population of cells can be heterogenous.

In some embodiments, provided herein are methods of treating tumor or cancer in a subject in need thereof, comprising administering to the subject a therapeutically effective amount of the pharmaceutical composition disclosed herein. In some embodiments, provided herein are uses of the pharmaceutical composition disclosed herein in treatment of tumor or cancer. In some embodiments, provided herein are uses of the pharmaceutical composition provided herein for the preparation of a medicament for the treatment of tumor or cancer.

Actual dosage levels of the active ingredients (i.e., the anti-mesothelin antibodies or antigen-binding fragments or the immune effector cells provided herein) in the pharmaceutical compositions described herein can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts.

The anti-mesothelin antibodies or antigen-binding fragments can be administered as a sustained release formulation, in which case less frequent administration is required. Dosage and frequency vary depending on the half-life of the anti-mesothelin antibodies or antigen-binding fragments in the patient. In therapeutic applications, a relatively high dosage at relatively short intervals is sometimes required until progression of the disease is reduced or terminated, and until the patient shows partial or complete amelioration of symptoms of disease.

In some embodiments, immune effector cells provided herein that recombinantly express the mesothelin CARs or TCRs disclosed herein can be used in the therapeutic methods disclosed herein. When a cell therapy is adopted, the cells provided herein can be administered as a dose based on cells per kilogram (cells/kg) of body weight of the subject to which the cells are administered. The cell doses can be in the range of about $10^4$ to about $10^{10}$ cells/kg of body weight, for example, about $10^5$ to about $10^9$, about $10^5$ to about $10^8$, about $10^5$ to about $10^7$, or about $10^5$ to $10^6$ cells/kg of body weight, depending on the mode and location of administration. In general, in the case of systemic administration, a higher dose is used than in regional administration, where the immune effector cells are administered in the region of a tumor. The precise determination of what would be considered an effective dose can be based on factors individual to each subject, including their size, age, sex, weight, and condition of the particular subject, as described above. Dosages can be readily determined by those skilled in the art based on the disclosure herein and knowledge in the art.

The anti-mesothelin antibodies or antigen-binding fragments, immune effector cells, and pharmaceutical compositions provided herein can be administered to a subject by any methods known in the art, including, but not limited to, pleural administration, intravenous administration, subcutaneous administration, intranodal administration, intratumoral administration, intramuscular administration, intradermal administration, intrathecal administration, intrapleural administration, intraperitoneal administration, intracranial administration, spinal or other parenteral routes of administration, for example by injection or infusion, or direct administration to the thymus. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion. In some embodiments, subcutaneous administration is adopted. In some embodiments, intravenous administration is adopted. In some embodiments, oral administration is adopted. In one embodiment, the cells provided herein can be delivered regionally to a tumor using well known methods, including but not limited to, hepatic or aortic pump; limb, lung or liver perfusion; in the portal vein; through a venous shunt; in a cavity or in a vein that is nearby a tumor, and the like. In another embodiment, the cells provided herein can be administered systemically. In a preferred embodiment, the cells are administered regionally at the site of a tumor. The cells can also be administered intratumorally, for example, by direct injection of the cells at the site of a tumor and/or into the tumor vasculature. For example, in the case of malignant pleural disease, mesothelioma or lung cancer, administration is preferably by intrapleural administration (see Adusumilli et al., *Science Translational Medicine* 6(261):261ra151 (2014)). One skilled in the art can select a suitable mode of administration based on the type of cancer and/or location of a tumor to be treated. The cells can be introduced by injection or catheter. In one embodiment, the cells are pleurally administered to the subject in need, for example, using an intrapleural catheter. Optionally, expansion and/or differentiation agents can be administered to the subject prior to, during or after administration of cells to increase production of the cells provided herein in vivo.

Proliferation of the cells provided herein is generally done ex vivo, prior to administration to a subject, and can be desirable in vivo after administration to a subject (see Kaiser et al., *Cancer Gene Therapy* 22:72-78 (2015)). Cell proliferation should be accompanied by cell survival to permit cell expansion and persistence, such as with T cells.

Cancers or tumors to be treated using the anti-mesothelin antibodies or antigen-binding fragments, cells, or pharmaceutical compositions provided herein comprise cancers typically responsive to immunotherapy. The anti-mesothelin antibodies or antigen-binding fragments, cells, or pharmaceutical compositions disclosed herein can be used to treat treating diseases and disorders associated with mesothelin. Mesothelioma, for example, is a disease associated with mesothelin.

Malignant mesothelioma is a type of cancer that occurs in the thin layer of cells lining the body's internal organs, known as the mesothelium. There are three recognized types of mesothelioma. Pleural mesothelioma (e.g., malignant pleural mesothelioma, or MPM) is the most common form of the disease, accounting for roughly 70% of cases, and occurs in the lining of the lung known as the pleura. Peritoneal mesothelioma occurs in the lining of the abdominal cavity, known as the peritoneum. Pericardial mesothelioma originates in the pericardium, which lines the heart. In some embodiments, anti-mesothelin antibodies or antigen-binding fragments, cells, or pharmaceutical compositions disclosed herein can be used to treat mesothelioma. In some embodiments, the mesothelioma is pleural mesothelioma. In some embodiments, the mesothelioma is peritoneal mesothelioma. In some embodiments, the mesothelioma is pericardial mesothelioma.

Symptoms of pleural mesothelioma include, e.g., lower back pain or side chest pain, and shortness of breath. Other symptoms include difficulty swallowing, persistent cough, fever, weight loss or fatigue. Additional symptoms that some patients experience include muscle weakness, loss of sensory capability, coughing up blood, facial and arm swelling, and hoarseness. In the early stages of the disease, such as stage 1 mesothelioma, symptoms can be mild. Patients usually report pain in one area of the chest that never seems to go away, weight loss and fever.

Peritoneal mesothelioma originates in the abdomen and as a result, symptoms often include abdominal pain, weight loss, nausea, and vomiting. Fluid buildup may occur in the abdomen as well as a result of the cancer. Peritoneal mesothelioma originates in the abdomen and will frequently spread to other organs in area including the liver, spleen or bowel. Severe abdominal pain is the most common complaint that patients first experience. There can also be a discomfort level with fluid buildup in the abdomen as well. Other symptoms of peritoneal mesothelioma may include difficult bowel movements, nausea and vomiting, fever and swollen feet.

Pericardial mesothelioma is the least common form of mesothelioma. Pericardial mesothelioma involves the heart. This rare type of mesothelioma cancer invades the pericardium. As the cancer progresses, the heart is not able to deliver oxygen as efficiently to the body causing further decline in health at an increasingly rapid rate. The symptoms most commonly associated with pericardial mesothelioma mimic those of a heart attack: nausea, pain in the chest and shortness of breath.

In some embodiments, methods provided herein can treat a subject having mesothelioma. In some embodiments, methods provided herein can treat a subject at risk to develop mesothelioma. A subject can be at risk to develop mesothelioma if the subject has been exposed to asbestos. Exposure to asbestos and the inhalation of asbestos particles can cause mesothelioma. In most cases, mesothelioma symptoms will not appear in a subject exposed to asbestos until many years after the exposure has occurred. In some embodiments, methods provided herein can treat a subject suspected of having mesothelioma, e.g., as evidenced by the presence of one or more of the symptoms described herein and/or exposure to asbestos. In some embodiments, the subject that can be treated with the methods disclosed herein can have a precancerous condition such as, e.g., pleural plaques, benign mesothelioma or mesothelial hyperplasia.

Another example of a disease or disorder associated with mesothelin is pancreatic cancer. In some embodiments, the anti-mesothelin antibodies or antigen-binding fragments, cells, or pharmaceutical compositions provided herein can be used to treat pancreatic cancer. Pancreatic cancers that can be treated with methods described herein include, but are not limited to, exocrine pancreatic cancers and endocrine pancreatic cancers. Exocrine pancreatic cancers include, but are not limited to, adenocarcinomas, acinar cell carcinomas, adenosquamous carcinomas, colloid carcinomas, undifferentiated carcinomas with osteoclast-like giant cells, hepatoid carcinomas, intraductal papillarymucinous neoplasms, mucinous cystic neoplasms, pancreatoblastomas, serous cystadenomas, signet ring cell carcinomas, solid and pseuodpapillary tumors, pancreatic ductal carcinomas, and undifferentiated carcinomas. In some embodiments, the exocrine pancreatic cancer is pancreatic ductal carcinoma. Endocrine pancreatic cancers include, but are not limited to, insulinomas and glucagonomas.

In some embodiments, the pancreatic cancer is any of early stage pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, recurrent pancreatic cancer, pancreatic cancer in an adjuvant setting, or pancreatic cancer in a neoadjuvant setting. In some embodiments, the pancreatic cancer is locally advanced pancreatic cancer, unresectable pancreatic cancer, or metastatic pancreatic ductal carcinoma. In some embodiments, the pancreatic cancer is resistant to the gemcitabine-based therapy. In some embodiments, the pancreatic cancer is refractory to the gemcitabine-based therapy.

Ovarian cancer can also be associated with mesothelin expression. In some embodiments, the anti-mesothelin antibodies or antigen-binding fragments, cells, or pharmaceutical compositions provided herein can be used to treat ovarian cancer. Ovarian cancer is classified according to the histology of the tumor. Surface epithelial-stromal tumor, also known as ovarian epithelial carcinoma, is the most common type of ovarian cancer. It includes serous tumor (including serous papillary cystadenocarcinoma), endometrioid tumor and mucinous cystadenocarcinoma.

The methods described herein can be used to treat various stages of ovarian cancer, e.g., stage I, stage II, stage III or stage IV. Staging can be performed, e.g., when the ovarian cancer is removed. Ovarian cancer is staged as follows: Stage I cancer is confined to one or both ovaries. The cancer is stage II if either one or both of the ovaries is involved and has spread to the uterus and/or the fallopian tubes or other sites in the pelvis. The cancer is stage III cancer if one or both of the ovaries is involved and has spread to lymph nodes or other sites outside of the pelvis but is still within the abdominal cavity, such as the surface of the intestine or liver. The cancer is stage IV cancer if one or both ovaries are involved and the cancer has spread outside the abdomen or to the inside of the liver.

In some embodiments, the ovarian cancer is resistant to one or more chemotherapeutic agent. In some embodiments, the ovarian cancer is refractory to the one or more chemotherapeutic agent.

Other cancers that can be treated with the anti-mesothelin antibodies or antigen-binding fragments, cells, or pharmaceutical compositions provided herein include, e.g., brain cancer, bladder cancer, breast cancer, cervical cancer, colorectal cancer, liver cancer, kidney cancer, lymphoma, leukemia, lung cancer (e.g., lung adenocarcinoma), melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

In cancer treatment, eliminating cancer or tumor cells in a subject can occur, but any clinical improvement constitutes a benefit. An anti-tumor effect can be manifested by a decrease in tumor volume, a decrease in the number of tumor cells, a decrease in the number of metastases, an increase in life expectancy, or amelioration of various physiological symptoms associated with the cancerous condition. An anti-tumor effect can also be manifested by the ability of the cells or pharmaceutical compositions provided herein in prevention of the occurrence of tumor in the first place. In some embodiments, an "anti-tumor effect" can be manifested by the reduction in cancer-induced immunosuppression. Clinical improvement comprises decreased risk or rate of progression or reduction in pathological consequences of the cancer or tumor. It is also understood that a method of treating cancer can include any effect that ameliorates a sign or symptom associated with cancer. Such signs or symptoms include, but are not limited to, reducing tumor burden, including inhibiting growth of a tumor, slowing the growth rate of a tumor, reducing the size of a tumor, reducing the number of tumors, eliminating a tumor, all of which can be measured using routine tumor imaging techniques well known in the art. Other signs or symptoms associated with cancer include, but are not limited to, fatigue, pain, weight loss, and other signs or symptoms associated with various cancers.

In some embodiments, the methods or uses provided herein can reduce tumor burden. Thus, administration of the anti-mesothelin antibodies or antigen-binding fragments, cells or pharmaceutical compositions disclosed herein can reduce the number of tumor cells, reduce tumor size, and/or eradicate the tumor in the subject. Methods for monitoring patient response to administration of a pharmaceutical composition disclosed herein are known in the art and can be employed in accordance with methods disclosed herein.

In the methods disclosed herein, a therapeutically effective amount of the anti-mesothelin antibodies or antigen-binding fragments, cells or pharmaceutical compositions disclosed herein is administered to a subject in need of cancer treatment. The subject can be a mammal. In some embodiments, the subject is a human. In some embodiments, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts and are suitably defined for different types of cancers. Features typical of high-risk subgroups are those in which the tumor has invaded neighboring tissues, or who show involvement of lymph nodes.

Anti-mesothelin antibodies or antigen-binding fragments, cells, or pharmaceutical compositions provided herein can be administered with medical devices known in the art. For example, in some embodiments, a needleless hypodermic injection device can be used, such as the devices disclosed in U.S. Pat. Nos. 5,399,163; 5,383,851; 5,312,335; 5,064,413; 4,941,880; 4,790,824; or 4,596,556. Examples of well-known implants and modules for use described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Combination therapy using agents with different mechanisms of action can result in additive or synergetic effects. Combination therapy can allow for a lower dose of each agent than is used in monotherapy, thereby reducing toxic side effects and/or increasing the therapeutic index of the agent disclosed herein. Combination therapy can decrease the likelihood that resistant cancer cells will develop. In some embodiments, the additional therapy results in an increase in the therapeutic index of the cells or pharmaceutical compositions described herein. In some embodiments, the additional therapy results in a decrease in the toxicity and/or side effects of cells or pharmaceutical compositions described herein. In some embodiments, the anti-mesothelin antibodies or antigen-binding fragments, cells, or pharmaceutical compositions described herein can be administered in combination with an additional therapy. In some embodiments, the additional therapy can be surgical resection, radiotherapy, or chemotherapy.

The additional therapy can be administered prior to, concurrently with, or subsequent to administration of the anti-mesothelin antibodies or antigen-binding fragments, cells, or pharmaceutical compositions described herein. Combined administration can include co-administration, either in a single pharmaceutical formulation or using separate formulations, or consecutive administration in either order but generally within a time period such that all active agents can exert their biological activities simultaneously. A person skilled in the art can readily determine appropriate regimens for administering a pharmaceutical composition described herein and an additional therapy in combination, including the timing and dosing of an additional agent to be used in a combination therapy, based on the needs of the subject being treated.

5.8 Methods of Production 5.8.1 Polynucleotides, Polypeptides, and Antibodies

Polynucleotides provided herein can be prepared, manipulated, and/or expressed using any of the well-established techniques known and available in the art. Many vectors can be used. Examples of vectors are plasmid, autonomously replicating sequences, and transposable elements. Exemplary transposon systems such as Sleeping Beauty and PiggyBac can be used, which can be stably integrated into the genome (e.g., Ivics et al., Cell, 91 (4): 501-510 (1997); Cadiñanos et al., (2007) Nucleic Acids Research. 35 (12): e87). Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pClneo vectors (Promega) for expression in mammalian cells; pLenti4/V5-DEST™, pLenti6N5-DEST™, and pLenti6.2/V5-GW/lacZ (Invitrogen) for lentivirus-mediated gene transfer and expression in mammalian cells.

In some embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. In some embodiments, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus. Typically, the host cell comprises the viral replication transactivator protein that activates the replication.

"Expression control sequences," "control elements," or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements can vary in their strength and specificity. Depending on the vector system and host utilized, any number of suitable transcription and translation elements, including ubiquitous promoters and inducible promoters can be used.

Illustrative ubiquitous expression control sequences that can be used in present disclosure include, but are not limited to, a cytomegalovirus (CMV) immediate early promoter, a viral simian virus 40 (SV40) promoter (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc. The anti-mesothelin antibodies or antigen-binding fragments described herein can be produced by any method known in the art, including chemical synthesis and recombinant expression techniques. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) MOLECULAR CLONING: A LABORATORY MANUAL, Cold Spring Harbor Laboratory Press; Sambrook et al. (1989), MOLECULAR CLONING: A LABORATORY MANUAL, Second Edition, Cold Spring Harbor Laboratory Press; Sambrook et al. (2001) MOLECULAR CLONING: A LABORATORY MANUAL, Cold Spring Harbor Laboratory Press, Cold Spring Harbor, NY; Ausubel et al., CURRENT PROTOCOLS IN MOLECULAR BIOLOGY, John Wiley & Sons (1987 and annual updates); CURRENT PROTOCOLS IN IMMUNOLOGY, John Wiley & Sons (1987 and annual updates) Gait (ed.) (1984) OLIGONUCLEOTIDE SYNTHESIS: A PRACTICAL APPROACH, IRL Press; Eckstein (ed.) (1991) OLIGONUCLEOTIDES AND ANALOGUES: A PRACTICAL APPROACH, IRL Press; Birren et al. (eds.) (1999) GENOME ANALYSIS: A LABORATORY MANUAL, Cold Spring Harbor Laboratory Press; Borrebaeck (ed.) (1995) ANTIBODY ENGINEERING, Second Edition, Oxford University Press; Lo (ed.) (2006) ANTIBODY ENGINEERING: METHODS AND PROTOCOLS (METHODS IN MOLECULAR BIOLOGY); Vol. 248, Humana Press, Inc; each of which is incorporated herein by reference in its entirety.

The polypeptides described herein (e.g., the anti-mesothelin antibodies or antigen-binding fragments, or CARs/TCRs) can be produced and isolated using methods known in the art. Peptides can be synthesized, in whole or in part, using chemical methods (see, e.g., Caruthers (1980). *Nucleic Acids Res. Symp. Ser.* 215; Horn (1980); and Banga, A. K., THERAPEUTIC PEPTIDES AND PROTEINS, FORMULATION, PROCESSING AND DELIVERY SYSTEMS (1995) Technomic Publishing Co., Lancaster, PA). Peptide synthesis can be performed using various solid phase techniques (see, e.g., Roberge, *Science* 269:202 (1995); Merrifield, *Methods. Enzymol.* 289:3 (1997)) and automated synthesis may be achieved, e.g., using the ABI 431A Peptide Synthesizer (Perkin Elmer) in accordance with the manufacturer's instructions. Peptides can also be synthesized using combinatorial methodologies. Synthetic residues and polypeptides can be synthesized using a variety of procedures and methodologies known in the art (see, e.g., ORGANIC SYNTHESES COLLECTIVE VOLUMES, Gilman, et al. (Eds) John Wiley & Sons, Inc., NY). Modified peptides can be produced by chemical modification methods (see, for example, Belousov, *Nucleic Acids Res.* 25:3440 (1997); Frenkel, *Free Radic. Biol. Med.* 19:373 (1995); and Blommers, *Biochemistry* 33:7886 (1994)). Peptide sequence variations, derivatives, substitutions and modifications can also be made using methods such as oligonucleotide-mediated (site-directed) mutagenesis, alanine scanning, and PCR based mutagenesis. Site-directed mutagenesis (Carter et al., *Nucl. Acids Res.*, 13:4331 (1986); Zoller et al., *Nucl. Acids Res.* 10:6487 (1987)), cassette mutagenesis (Wells et al, *Gene* 34:315 (1985)), restriction selection mutagenesis (Wells et al., *Philos. Trans. R. Soc. London SerA* 317:415 (1986)) and other techniques can be performed on cloned DNA to produce invention peptide sequences, variants, fusions and chimeras, and variations, derivatives, substitutions and modifications thereof.

The polypeptides described herein can be prepared using a wide variety of techniques known in the art including the use of hybridoma and recombinant technologies, or a combination thereof. In some embodiments, a recombinant expression vector is used to express a polynucleotide encoding a polypeptide described herein. For example, a recombinant expression vector can be a replicable DNA construct that includes synthetic or cDNA-derived DNA fragments encoding a polypeptide operatively linked to suitable transcriptional and/or translational regulatory elements derived from mammalian, microbial, viral or insect genes. In some embodiments, coding sequences of polypeptides disclosed herein can be ligated into such expression vectors for their expression in mammalian cells. In some embodiments, a viral vector is used. DNA regions are "operatively linked" when they are functionally related to each other. For example, a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide can include an N-terminal methionine residue.

A wide variety of expression host/vector combinations can be employed. Suitable host cells for expression include prokaryotes, yeast cells, insect cells, or higher eukaryotic cells under the control of appropriate promoters. Appropriate cloning and expression vectors for use with bacterial, fungal, yeast, and mammalian cellular hosts, as well as methods of protein production, including antibody production are well-known in the art. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Useful expression vectors for eukaryotic hosts include, for example, vectors comprising expression control sequences from SV40, bovine papilloma virus, adenovirus, and cytomegalovirus. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Provided herein are anti-mesothelin antibodies and antigen-binding fragments thereof that include but are not limited to monoclonal antibodies, polyclonal antibodies, synthetic antibodies, human antibodies, humanized antibodies, and antigen-binding fragments thereof.

Methods of antibody production are well-known in the art. See for example, in Harlow et al., Antibodies: A Laboratory Manual, (Cold Spring Harbor Laboratory Press, 2nd ed. 1988); Hammerling et al., in: MONOCLONAL ANTIBODIES AND T-CELL HYBRIDOMAS 563 681 (Elsevier, N.Y., 1981), each of which is incorporated herein by reference in its entirety. For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. For example, anti-mesothelin antibodies directed against the human mesothelin antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (*Int. Rev. Immunol.*, 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al, *Proc. Natl. Acad. Sci. USA*, 90:2551 (1993); Jakobovits et al., *Nature*, 362:255-258 (1993); Brugermann et al., *Year in Immunol.*, 7:33 (1993); and Duchosal et al., *Nature*, 355:258 (1992).

Human antibodies can also be derived from phage-display libraries (Hoogenboom et al., *J. Mol. Biol.*, 227:381 (1991); Marks et al., *J. Mol. Biol.*, 222:581-597 (1991); Vaughan et al., *Nature Biotech.*, 14:309 (1996)). Phage display technology (McCafferty et al, *Nature*, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson and Chiswell, *Current Opinion in Structural Biology* 3:564-571 (1993).

Several sources of V-gene segments can be used for phage display. Clackson et al., *Nature*, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., *J. Mol. Biol.*, 222:581-597 (1991), or Griffith et al., *EMBO* 1, 12:725-734 (1993). See, also, U.S. Pat. Nos. 5,565,332 and 5,573,905, each of which is incorporated herein by reference in its entirety.

Human antibodies can also be generated by in vitro activated B cells (see, U.S. Pat. Nos. 5,567,610 and 5,229,275, each of which is incorporated herein by reference in its entirety). Human antibodies can also be generated in vitro using hybridoma techniques such as, but not limited to, that described by Roder et al. (*Methods Enzymol.*, 121:140-167 (1986)).

Alternatively, in some embodiments, a non-human antibody is humanized, where specific sequences or regions of the antibody are modified to increase similarity to an antibody naturally produced in a human. In some embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, *Molecular Immunology*, 28(4/5): 489-498; Studnicka et al., 1994, *Protein Engineering*, 7(6): 805-814; and Roguska et al., 1994, *PNAS*, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., *J. Immunol.*, 169:1119-25 (2002), Caldas et al., *Protein Eng.*, 13(5):353-60 (2000), Morea et al., *Methods*, 20(3):267-79 (2000), Baca et al., *J. Biol. Chem.*, 272(16):10678-84 (1997), Roguska et al., *Protein Eng.*, 9(10):895-904 (1996), Couto et al., *Cancer Res.*, 55 (23 Supp):5973s-5977s (1995), Couto et al., *Cancer Res.*, 55(8):1717-22 (1995), Sandhu J S, *Gene*, 150(2):409-10 (1994), and Pedersen et al., *J. Mol. Biol.*, 235(3):959-73 (1994), each of which is incorporated herein in its entirety by reference. Often, framework residues in the framework regions can be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, *Nature*, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FR residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., *Protein Engineering,* 7(6):805-814 (1994); and Roguska et al., *PNAS,* 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.,* 151:2296 (1993); Chothia et al., *J. Mol. Biol.,* 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993), the contents of which are incorporated herein by reference herein in their entirety).

Antibodies can be humanized with retention of high affinity for the target antigen and other favorable biological properties. For example, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody, for example, the ability to bind human mesothelin antigen. However, using certain methods of humanization, the affinity and/or specificity of binding of the antibody for a particular antigen can be increased using methods of "directed evolution," as described by Wu et al., *J Mol. Biol.,* 294:151 (1999), the contents of which are incorporated herein by reference herein in their entirety.

5.8.2 Genetically Engineered Immune Effector Cells

In some embodiments, provided herein is a genetically engineered immune effector cell that comprises a polynucleotide encoding a mesothelin CAR or TCR disclosed herein. In some embodiments, provided herein is a genetically engineered immune effector cell that recombinantly expresses a mesothelin CAR or TCR disclosed herein. In some embodiments, provided herein is a genetically engineered immune effector cell that comprises a vector comprising a polynucleotide encoding a mesothelin CAR or TCR disclosed herein. In some embodiments, the immune effector cells are T cells.

5.8.2.1 Methods of Genetic Engineering

With respect to generating cells recombinantly expressing a mesothelin CAR or TCR disclosed herein, one or more polynucleotides encoding the mesothelin CAR or TCR is introduced into the target cell using a suitable expression vector. The target immune effector cells (e.g., T cells) are transferred with one or more polynucleotides encoding a mesothelin CAR or TCR. The genetically engineered cells can also express the anti-mesothelin antibodies or antigen-binding fragments disclosed herein.

In some embodiments, provided herein are methods of genetically engineering an immune effector cell by transferring a polynucleotide provided herein into the cell using a non-viral delivery system. The mesothelin CAR or TCR encoding polynucleotide can be mRNA, which allows transient expression and the self-elimination of the immune effector cells expressing such mesothelin CAR or TCR. Physical methods for introducing a polynucleotide into a host cell include calcium phosphate precipitation, lipofection, particle bombardment, microinjection, electroporation, and the like. In some embodiments, RNA electroporation can be used (Van Driessche et al. *Folia histochemica et cytobiologica* 43:4 213-216 (2005)). The methods can further include preparing the mRNA by in vitro transcribing the polynucleotides described herein. In some embodiments, provided herein are methods of genetically engineering an immune effector cell by transferring a polynucleotide encoding anti-mesothelin antibodies or antigen-binding fragments disclosed herein into the cell using electroporation. In some embodiments, provided herein are methods of genetically engineering an immune effector cell by transferring a polynucleotide encoding mesothelin CARs or TCRs disclosed herein into the cell using electroporation.

In some embodiments, DNA transfection and transposon can be used. In some embodiments, the Sleeping Beauty system or PiggyBac system is used (e.g., Ivics et al., *Cell,* 91 (4): 501-510 (1997); Cadiñanos et al. (2007) *Nucleic Acids Research.* 35 (12): e87). Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

For example, a polynucleotide encoding a mesothelin CAR or TCR disclosed herein can be cloned into a suitable vector, and introduced into the target cell using well known molecular biology techniques (see Ausubel et al., *Current Protocols in Molecular Biology*, John Wiley and Sons, Baltimore, MD (1999)). Any vector suitable for expression in a cell, particularly a human cell, can be used. The vectors contain suitable expression elements such as promoters that provide for expression of the encoded nucleic acids in the target cell.

The use of retroviral vectors for expression in T cells or other immune effector cells, including engineered T cells, has been described (see Scholler et al., *Sci. Transl. Med.* 4:132-153 (2012; Parente-Pereira et al, *J. Biol. Methods* 1(2):e7 (1-9)(2014); Lamers et al., *Blood* 117(1):72-82 (2011); Reviere et al., *Proc. Natl. Acad. Sci. USA* 92:6733-6737 (1995)). In some embodiments, the vector is a gamma retroviral vector. In one embodiment, the vector is an SGF retroviral vector such as an SGF γ-retroviral vector, which is Moloney murine leukemia-based retroviral vector. SGF vectors have been described previously (see, for example, Wang et al., *Gene Therapy* 15:1454-1459 (2008)). In the case of a retroviral vector, cells can optionally be activated to increase transduction efficiency (see Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al., *Mol. Ther.* 8:29-41 (2003); Agarwal et al., *J. Virol.* 72:3720-3728 (1998); Pollok et al., *Hum. Gene Ther.* 10:2221-2236 (1998); Quinn et al., *Hum. Gene Ther.* 9:1457-1467 (1998); see also commercially available methods such as Dynabeads™ human T cell activator products, Thermo Fisher Scientific, Waltham, MA). It is understood that any suitable viral vector or non-viral delivery system can be used. Combinations of a retroviral vector and an appropriate packaging line are also suitable, where the capsid proteins will be functional for infecting human cells. Various amphotropic virus-producing cell lines are known, including, but not limited to, PA12 (Miller et al, *Mot Cell. Biol.* 5:431-437 (1985)); PA317 (Miller et al., *Mol. Cell. Biol.* 6:2895-2902(1986)); and CRIP (Danos et al., *Proc. Natl. Acad. Sci. USA* 85:6460-6464 (1988)). Non-amphotropic particles are suitable too, for example, particles pseudotyped with VSVG, RD114 or GALV envelope and any other known in the art (Relander et al., *Mol. Therap.* 11:452-459 (2005)). Possible methods of transduction also include direct co-culture of the cells with producer cells (for example, Bregni et al., *Blood* 80:1418-1422 (1992)), or culturing with viral supernatant alone or concentrated vector stocks with or without appropriate growth factors and polycations (see, for example, Xu et al., *Exp. Hemat.* 22:223-230 (1994); Hughes, et al. *J. Clin. Invest.* 89:1817-1824 (1992)).

Other viral vectors that can be used include, for example, adenoviral, lentiviral, and adeno-associated viral vectors, vaccinia virus, a bovine papilloma virus derived vector, or a herpes virus, such as Epstein-Barr Virus (see, for example, Miller, *Hum. Gene Ther.* 1(1):5-14 (1990); Friedman, *Science* 244:1275-1281 (1989); Eglitis et al., *BioTechniques* 6:608-614 (1988); Tolstoshev et al., *Current Opin. Biotechnol.* 1:55-61 (1990); Sharp, *Lancet* 337:1277-1278 (1991); Cornetta et al., *Prog. Nucleic Acid Res. Mol. Biol.* 36:311-322 (1989); Anderson, *Science* 226:401-409 (1984); Moen, *Blood Cells* 17:407-416 (1991); Miller et al., *Biotechnology* 7:980-990 (1989); Le Gal La Salle et al., *Science* 259:988-990 (1993); and Johnson, *Chest* 107:77S-83S (1995)). Retroviral vectors are particularly well developed and have been used in clinical settings (Rosenberg et al., *N. Engl. J. Med.* 323:370 (1990); Anderson et al., U.S. Pat. No. 5,399, 346). Generally, the chosen vector exhibits high efficiency of infection and stable expression (see, for example, Cayouette et al., *Human Gene Therapy* 8:423-430 (1997); Kido et al., *Current Eye Research* 15:833-844 (1996); Bloomer et al., *J. Virol.* 71:6641-6649 (1997); Naldini et al., *Science* 272:263-267 (1996); and Miyoshi et al., *Proc. Natl. Acad. Sci. U.S.A.* 94:10319-10323 (1997)).

The vectors used herein employ suitable promoters for expression in a particular host cell. The promoter can be an inducible promoter or a constitutive promoter. In some embodiments, the promoter of an expression vector provides expression in a stem cell, such as a hematopoietic stem cell. In some embodiments, the promoter of an expression vector provides expression in an immune effector cell, such as a T cell. Non-viral vectors can be used as well, so long as the vector contains suitable expression elements for expression in the target cell. Some vectors, such as retroviral vectors, can integrate into the host genome.

In some embodiments, provided herein are methods of genetically engineering an immune effector cell by transferring a polynucleotide provided herein into the cell using gene-editing. If desired, targeted integration can be implemented using technologies such as a nuclease, transcription activator-like effector nucleases (TALENs), Zinc-finger nucleases (ZFNs), clustered regularly interspaced short palindromic repeats (CRISPRs), homologous recombination, non-homologous end joining, microhomology-mediated end joining, homology-mediated end joining and the like (Gersbach et al., *Nucl. Acids Res.* 39:7868-7878 (2011); Vasileva, et al. *Cell Death Dis.* 6:e1831. (Jul. 23 2015); Sontheimer, *Hum. Gene Ther.* 26(7):413-424 (2015); Yao et al. Cell Research volume 27, 801-814(2017)). In some embodiments, methods provided herein use a ZFN system. A zinc-finger nuclease consists of a DNA recognition domain and a non-specific endonuclease. The DNA recognition domain consists of a series of Cys2-His2 zinc-finger proteins linked in series, and each zinc-finger unit includes about 30 amino acids for specifically binding to DNA. The non-specific endonuclease is a FokI endonuclease which forms a dimer to cleave the DNA. In some embodiments, methods provided herein use a TALEN system. TALEN is a transcription activator-like effector nuclease. The TALE protein is a core component of a DNA binding domain, and generally consists of a plurality of basic repeat units linked in series. The designed and combined series of units can specifically recognize a DNA sequence and cleave a specific DNA sequence by coupling the Fold endonuclease.

In some embodiments, methods provided herein use a CRISPR-Cas system. The CRISPR-Cas system can be a CRISPR-Cas9 system. CRISPR/Cas system is a nuclease system consisting of clustered regularly interspaced short palindromic repeats (CRISPR) and CRISPR binding proteins (i.e., Cas proteins), which can cleave nearly all genomic sequences adjacent to protospacer-adjacent motifs (PAM) in eukaryocytes (Cong et al. *Science* 2013. 339: 819-823). The "CRISPR/Cas system" is used to refer collectively to transcripts involving CRISPR-related ("Cas") genes, as well as other elements involving the expression thereof or directing the activity thereof, including sequences encoding a Cas gene, tracr (trans-activated CRISPR) sequences (for example, tracrRNA or active partial tracrRNA), tracr pairing sequences (in the background of an endogenous CRISPR system, cover "direct repeats" and processed partial direct repeats), guide sequences, or other sequences from the CRISPR locus and transcripts. In general, the CRISPR system is characterized as an element that facilitates the formation of a CRISPR complex at a site of a target sequence (also called a protospacer in the endogenous CRISPR system). Unrestricted examples of the Cas protein include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 homologues, or modified forms thereof. In some embodiments, the Cas protein is a Cas9 protein (Gasiunas, Barrangou et al. 2012; Jinek, Chylinski et al. 2012; Deltcheva, Chylinski et al. 2011; Makarova, Grishin et al. (2006)). Amino acid sequences of the Cas9 protein are known in the art. Exemplary sequences can be found, for example, in the SwissProt database under the accession number Q99ZW2, in the UniProt database under the number A1IQ68, Q03LF7, or J7RUA5.

The vectors and constructs can optionally be designed to include a reporter. For example, the vector can be designed to express a reporter protein, which can be useful to identify cells comprising the vector or polynucleotides provided on the vector, such as polynucleotides that have integrated into the host chromosome. In one embodiment, the reporter can be expressed as a bicistronic or multicistronic expression construct with the anti-mesothelin antibody or antigen-binding fragment or the mesothelin CAR or TCR. Exemplary reporter proteins include, but are not limited to, fluorescent proteins, such as mCherry, green fluorescent protein (GFP), blue fluorescent protein, for example, EBFP, EBFP2, Azurite, and mKalama1, cyan fluorescent protein, for example, ECFP, Cerulean, and CyPet, and yellow fluorescent protein, for example, YFP, Citrine, Venus, and YPet.

Assays can be used to determine the transduction efficiency using routine molecular biology techniques. If a marker has been included in the construct, such as a fluorescent protein, gene transfer efficiency can be monitored by FACS analysis to quantify the fraction of transduced (for example, GFP$^+$) immune effector cells, such as T cells, and/or by quantitative PCR. Using a well-established cocultivation system (Gade et al., Cancer Res. 65:9080-9088 (2005); Gong et al., Neoplasia 1:123-127 (1999); Latouche et al., Nat. Biotechnol. 18:405-409 (2000)) it can be determined whether fibroblast AAPCs expressing cancer antigen (vs. controls) direct cytokine release from transduced immune effector cells, such as T cells, expressing a CAR (cell supernatant LUMINEX (Austin TX) assay for IL-2, IL-4, IL-10, IFN-γ, TNF-α, and GM-CSF), T cell proliferation (by carboxyfluorescein succinimidyl ester (CFSE) labeling), and T cell survival (by Annexin V staining). The influence of CD80 and/or 4-1BBL on T cell survival, proliferation, and efficacy can be evaluated. T cells can be exposed to repeated stimulation by cancer antigen positive target cells, and it can be determined whether T cell proliferation and cytokine response remain similar or diminished with repeated stimulation. The cancer antigen CAR constructs can be compared side by side under equivalent assay conditions. Cytotoxicity assays with multiple E:T ratios can be conducted using chromium-release assays.

Combinations and permutations of various methods described herein or otherwise known in the art are expressly contemplated to prepare the genetically engineered cells disclosed herein.

5.8.2.2 Manipulation of Immune Effector Cells

Immune effector cells provided herein can be obtained from a subject. Sources for the immune effector cells provided herein include, but are not limited to, peripheral blood, umbilical cord blood, bone marrow, or other sources of hematopoietic cells. Immune effector cells (e.g., T cells) can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments, cell lines available in the art can be used. Immune effector cells provided herein can be isolated by methods well known in the art, including commercially available isolation methods (see, for example, Rowland-Jones et al., LYMPHOCYTES: A PRACTICAL APPROACH, Oxford University Press, New York (1999)). Various methods for isolating immune effector cells have been described previously, and can be used, including but not limited to, using peripheral donor lymphocytes (Sadelain et al., Nat. Rev. Cancer 3:35-45 (2003); Morgan et al., Science 314: 126-129 (2006), and using selectively in v/Yro-expanded antigen-specific peripheral blood leukocytes employing artificial antigen-presenting cells (AAPCs) or dendritic cells (Dupont et al., Cancer Res. 65:5417-5427 (2005); Papanicolaou et al., Blood 102:2498-2505 (2003)).

In certain embodiments, immune effector cells (e.g., T cells) disclosed herein can be obtained from a unit of blood collected from a subject using any techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis can be washed to remove the plasma fraction and to place the cells in an appropriate buffer or media for subsequent processing steps. In some embodiments, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step can be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells can be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample can be removed, and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+T$ cells, can be further isolated by positive or negative selection techniques. For example, in one embodiment, T cells are isolated by incubation with anti-$CD^3$/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention.

Various techniques can be employed to separate the cells to enrich for desired immune effector cells. For instance, negative selection methods can be used to remove cells that are not the desired immune effector cells. Additionally, positive selection methods can be used to isolate or enrich for desired immune effector cells or precursor cells thereof, or a combination of positive and negative selection methods can be employed. Monoclonal antibodies (MAbs) are particularly useful for identifying markers associated with particular cell lineages and/or stages of differentiation for both positive and negative selections. If a particular type of cell is to be isolated, for example, a particular type of T cell, various cell surface markers or combinations of markers, including but not limited to, CD3, CD4, CD8, CD34 (for hematopoietic stem and progenitor cells) and the like, can be used to separate the cells, as is well known in the art (see Kearse, T CELL PROTOCOLS: DEVELOPMENT AND ACTIVATION, Humana Press, Totowa NJ (2000); De Libero, T CELL PROTOCOLS, Vol. 514 of Methods in Molecular Biology, Humana Press, Totowa NJ (2009)). In some embodiments, enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, $CD25^+$, $CD62L^{hi}$, $GITR^+$, and $FoxP3^+$. Alternatively, in certain embodiments, T regulatory cells are depleted by anti-C25 conjugated beads or other similar method of selection.

Procedures for separation of immune effector cells include, but are not limited to, density gradient centrifugation, coupling to particles that modify cell density, magnetic separation with antibody-coated magnetic beads, affinity chromatography; cytotoxic agents joined to or used in conjunction with a monoclonal antibody (mAb), including, but not limited to, complement and cytotoxins, and panning with an antibody attached to a solid matrix, for example, a plate or chip, elutriation, flow cytometry, or any other convenient technique (see, for example, Recktenwald et al., CELL SEPARATION METHODS AND APPLICATIONS, Marcel Dekker, Inc., New York (1998)). It is understood that the immune effector cells used in methods provided herein can be substantially pure cells or can be a polyclonal population. In some embodiments, a polyclonal population can be enriched for a desired immune effector cell. Such an enrichment can take place prior to or after genetically engineering the cells to express a mesothelin CAR or TCR provided herein, as desired.

The immune effector cells can be autologous or non-autologous to the subject to which they are administered in the methods of treatment disclosed herein. Autologous cells are isolated from the subject to which the engineered cells are to be administered. Optionally, the cells can be obtained by leukapheresis, where leukocytes are selectively removed from withdrawn blood, made recombinant, and then retransfused into the donor. Alternatively, allogeneic cells from a non-autologous donor that is not the subject can be used. In the case of a non-autologous donor, the cells are typed and matched for human leukocyte antigen (HLA) to determine an appropriate level of compatibility, as is well known in the art. The cells can optionally be cryopreserved after isolation and/or genetic engineering, and/or expansion of genetically engineered cells (see Kaiser et al., supra, 2015)). Methods for cyropreserving cells are well known in the art (see, for example, Freshney, CULTURE OF ANIMAL CELLS: A MANUAL OF BASIC TECHNIQUES, 4th ed., Wiley-Liss, New York (2000); Harrison and Rae, GENERAL TECHNIQUES OF CELL CULTURE, Cambridge University Press (1997)).

In some embodiments, isolated immune effector cells are genetically engineered ex vivo for recombinant expression of a polypeptide (e.g., CAR or TCR). In some embodiments, isolated immune effector cells are genetically engineered ex vivo for recombinant expression of a mesothelin CAR or TCR. In some embodiments, immune effector cells provided herein are obtained by in vitro sensitization, wherein the sensitization can occur before or after the immune effector cells are genetically engineered to recombinantly express a polypeptide disclosed herein. In an embodiment where the sensitized immune effector cells, such T cells, are isolated from in vivo sources, it will be self-evident that genetic engineering occurs of the already-sensitized immune effector cells.

Also contemplated in the present disclosure is the collection of blood samples or apheresis product from a subject at a time period prior to when the genetically engineered cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment, a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells can be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al, Cell 66:807-815, 1991; Henderson et al., Immun 73:316-321, 1991; Bierer et al, Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained can be optimal or improved for their ability to expand ex vivo. Likewise, following ex vivo manipulation using the methods described herein, these cells may be in a preferred state for enhanced engraftment and in vivo expansion. Thus, it is contemplated to collect blood cells, including T cells, NK cells, or other immune effector cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

The immune effector cells disclosed herein can be subjected to conditions that favor maintenance or expansion of cells as well known in the art. (De Libero, *T Cell Protocols*, Vol. 514 of *Methods in Molecular Biology*, Humana Press, Totowa NJ (2009); Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al., *Mol. Ther.* 8:29-41 (2003); Agarwal et al., *J. Virol.* 72:3720-3728 (1998); Pollok et al., *Hum. Gene Ther.* 10:2221-2236 (1999); Quinn et al., *Hum. Gene Ther.* 9:1457-1467 (1998); see also commercially available methods such as Dynabeads™ human T cell activator products, Thermo Fisher Scientific, Waltham, MA)). The immune effector cells disclosed herein (e.g., T cells) can optionally be expanded prior to or after ex vivo genetic engineering. Expansion of the cells is particularly useful to increase the number of cells for administration to a subject. Such methods for expansion of cells are well known in the art (see e.g., Kaiser et al., *Cancer Gene Therapy* 22:72-78 (2015); Wolfl et al., *Nat. Protocols* 9:950-966 (2014)). Furthermore, the cells can optionally be cryopreserved after isolation and/or genetic engineering, and/or expansion of genetically engineered cells (see Kaiser et al., supra, 2015)). Methods for cyropreserving cells are well known in the art (see, for example, Freshney, *Culture of Animal Cells: A Manual of Basic Techniques*, 4th ed., Wiley-Liss, New York (2000); Harrison and Rae, *General Techniques of Cell Culture*, Cambridge University Press (1997)).

Generally, the T cells provided herein can be expanded by contact with a surface having attached thereto an agent that stimulates a CD3/TCR complex associated signal and a ligand that stimulates a co-stimulatory receptor on the surface of the T cells. In particular, T cell populations can be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

Particular embodiments of this invention are described herein, including the best mode known to the inventors for carrying out the invention. Upon reading the foregoing description, variations of the disclosed embodiments shall become apparent to individuals working in the art, and it is expected that those skilled artisans can employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference in its entirety as if each individual publication or patent application were specifically and individually indicated to be incorporated by reference. The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which need to be independently confirmed.

A number of embodiments of the invention have been described. Nevertheless, it will be understood that various modifications may be made without departing from the spirit and scope of the invention. Accordingly, the descriptions in the Experimental are intended to illustrate but not limit the scope of invention described in the claims.

5.9 Experimental

As disclosed in detail below, 38 anti-mesothelin scFv(s) were generated and characterized. T cells expressing CARs that comprise these mesothelin scFv(s) were also generated and characterized. The cytotoxicity of these mesothelin CARTs against cancer cells, including mesothelin-expressing cancer cells, was confirmed.

5.9.1 Example 1: Preparation of Anti-Mesothelin Antibodies

Anti-mesothelin antibodies were prepared using fully human antibody phage display library following the steps below:

(1) Expression and purification of phage display library: the log phase TG1 library culture was infected with freshly thawed M13K07 helper phage with a multiplicity of infection of 20:1 (phage-to-cell-ratio) and overnight induction by IPTG; the phage library was purified by PEG/NaCl precipitated method and phage titer was determined. The phage was stored at 4° C. and the scFv selection was performed shortly after.

(2) Selection of mesothelin-specific scFv-phages: for the first round of selection, Maxisorp plate was coated with 20 µg/ml mesothelin-6His protein dissolved in 1×PBS and incubated overnight at 4° C. (For subsequent rounds of selection, lower protein concentration was used for more stringent selection, including 2 µg/ml in the 2nd round bio-panning, and 0.5 ug/ml in the 3rd round bio-panning.) The plate was then washed three times with PBS, blocking buffer (5% milk+1% BSA in 1×PBS) was added to each well. After 2-hour incubation at room temperature, the blocking buffer was discarded, phage solution added, and the plate was sealed with parafilm, and incubated for 2 hours with gently shaking. In the first selection round, the plate was then washed 10 times with PBST. (For following rounds, increase stringency of washing was adopted by adding more wash cycles: 20 cycles in the $2^{nd}$ round, 30 cycles in the $3^{rd}$ round). The antigen-bound scFv-phages were then eluted using 1 ml acid elution buffer (pH 2.2), neutralized, inoculated in 15 ml of log-phase TG1 culture (OD600=0.5), cultured at 37° C. by 30 min standing and 30 min shaking, plated onto 2×YT-GA agar plate, and cultured overnight at 30° C. for subsequent selection.

(3) mpELISA screening: after three round selection, 288 positive colonies were selected for monoclonal phage ELISA (mpELISA) screening. Phage supernatant was generated from individual bacterial clones and tested for the binding to mesothelin-Fc protein. The supernatant was incubated with pre-blocked Maxisorp plate coated with 2 µg/ml mesothelin-6His protein. After three washes, 100 µl/well of HRP-conjugated anti-M13 antibody diluted 1:5000 in blocking buffer (5% milk+1% BSA in 1×PBS) was added and incubate for 60 min at RT. After washing plate 5 times with PBST, 100 µl/well TMB substrate solution was added and incubated for 10-30 min until blue color had appeared. Reaction was stopped by adding 50 µl/well of stop solution (2N $H_2SO_4$). Absorbance was read at 450 nm in a microplate reader. FIG. 1 shows the resultant absorbance read of the mpELISA screening. As shown, positive colonies (450 nm absorbance≥0.5) were identified to produce anti-mesothelin antibodies capable of binding mesothelin-6His protein (FIG. 1).

(4) Cloning and sequence analysis: positive clones were selected according to the ELISA results, and used as templates for PCR cloning of the scFv sequence (Forward primer sequence: tgcagctggcacgacaggtttc (SEQ ID NO: 22), reverse primer sequence: cgtcagactgtagcacgtt (SEQ ID NO: 23)). The PCR products were then sequenced by sanger sequencing method (Forward primer sequence: aacaattgaattcaggagga (SEQ ID NO: 24), reverse primer sequence: cctcctaagaagcgtagtc (SEQ ID NO: 25)). The CDR regions of scFv were analyzed through abysis website (http://abysis.org/), and are provided above in Tables 1 and 2.

5.9.2 Example 2: Preparation of Mesothelin CAR

Vectors for generating mRNA of anti-mesothelin CAR were constructed. First, the pDA vector was digested with Xba1 and Sal1 enzymes, and purified by gel purification method. The scFv fragment and CAR fragment (CD8 hinge, CD8 transmembrane domain, 4-1BB co-stimulatory domain, CD3-zeta signaling domain) were amplified by PCR and purified by gel purification method. The scFv fragment, CAR fragment (from hinge domain to CD3-zeta domain) and pDA vector were ligated by Gibson assembly method and transformed to competent cells. The colonies with the correct construct were confirmed by sanger sequencing and selected for further experiment. FIG. 2 provides the schematic representation of pDA-CAR vector used for CAR mRNA generation.

Second, the pDA-CAR plasmid was linearized by digestion with Spe1 enzyme. The linearized vector was purified using PCR Cleanup kit and eluted with RNase-free water. The concentration of DNA was measured by nanodrop and checked by running agarose DNA gel. Then, in vitro transcription (IVT) was performed following the protocol of manufacturer (Thermofisher, Cat No: AM13455). Briefly, 1 µg template DNA, NTP/ARCA buffer, T7 buffer, GTP, T7 enzyme and RNase free H2O were added in 20 µl volume to 0.2 ml PCR tube and incubated at 37° C. for 3 hours. 3 hours later, 2 µl DNase was added per reaction, and incubated at 37° C. for 15 min. The tailing procedure was performed according to the manufacturer's suggestion. The IVT mRNA was purified using the RNasy kit (Qiagen), and the concentration of RNA was measured by nanodrop, and checked by running PAGE gel.

5.9.3 Example 3: Tumor Cell Lines and Primary Human Lymphocytes

Tumor cell lines, including A549-CBG (human lung cancer cells), H226-CBG (human lung carcinoma cells), MOLM14-CBG (human leukemia cells), ASPC1-CBG (human pancreatic tumor cells), HCC70-CBG (human breast cancer cells), and OVCAR3-CBG (human ovarian cancer cells) were cultured in RPMI-1640 medium supplemented with 10% FCS. Primary lymphocytes from normal donors were stimulated with anti-CD3/CD28 Dynabeads (Life Technologies) and cultured in R10 medium (RPMI-1640 supplemented with 10% FCS, Penicillin-Streptomycin (100×), HEPES (100×), sodium pyruvate (100×), Glutamax (100×), NEAA (100×)). T cells were cryopreserved at day 10 after stimulation in a solution of 90% FCS and 10% DMSO at 1e8 cells/vial.

5.9.4 Example 4: Preparation and Characterization of Mesothelin CARTs

Mesothelin CAR mRNA was introduced into A549 tumor cells and T cells by electroporation with the following procedures: A549 tumor cells and T cells were collected and washed with Opti-MEM medium for 3 times. The cell pellets were resuspended with Opti-MEM medium, and the cell concentration was adjusted to 1×10e7/ml. 10 μg RNA was aliquoted to 1.5 ml EP tube, added with 100 μl T cells or A549 cells, and mixed well. 100 μl cells mixed with RNA were added to the BTX electroporation cup, tapped to avoid bubble. Electroporation was performed using BTX machine at the following parameters: For T cells: 500 voltage, 0.7 ms; for A549 tumor cell: 300 voltage, 0.5 ms. The cells were then transferred to pre-warmed culture medium and culture at 37° C.

Binding of mesothelin CART cells to mesothelin-Fc recombinant protein was measured by FACS staining. As shown in FIG. 3, anti-mesothelin scFv-M1, -M2, -M3, -M6, -M7, -M8, -M9, -M10, -M11, -M12, -M13, -M14, -M15, -M16, -M17, -M20, -M22, -M23, -M24, -M25, -M27, -M28, -M29, -M30, -M31, -M32, -M33, -M34, -M35, -M36 and -M37 bound to mesothelin-Fc recombinant protein. T cell without CAR molecule served as control ("Mock"). As shown in FIG. 4, the ectopic expression level of mesothelin correlated with the amount of mesothelin mRNA that was introduced into A549 cells via electroporation.

The cytotoxicity of the mesothelin CART cells against tumor cells was measured in in vitro cytotoxicity assay. EGFP-expressing tumor cell lines or EGFP-A549 cells that were electroporated with different amount of tumor antigen were seeded on flat-bottomed 96-well plate at 3000 cells/100 μl/well. CART cells were diluted to appropriate concentration, seeded at 100 μl/well with tumor cells at different E/T ratios, such as 10:1, 3:1, 1:1. The co-culture plates were placed into IncuCyte S3 machine, and scanning parameters were set. After 3 days of scanning, the Total Green Object Integrated Intensity (GCU×μm²/well) was analyzed to calculate the killing efficiency.

A549 cells express mesothelin at low level. As shown in FIG. 5, CART cells expressing anti-mesothelin scFv-M4, -M22, -M28 and -M31 effectively impeded the growth of A549 cells, indicating that these scFv-based CART cells had comparably high cytotoxicity against tumor cells. As shown in FIG. 6, CART cells expressing anti-mesothelin scFv-M4, -M6, -M7, -M8, -M9, -M10, -M11, -M12, -M13, -M15, -M20, -M22, -M23, -M24, -M27, -M28, -M31, -M32, -M35, -M37 and -M38 CART cells showed effectively killing effect toward the mesothelin over-expressing A549 tumor cells (electroporated with 10 μg mesothelin mRNA). As shown in FIG. 7, CART cells expressing anti-mesothelin scFv-M4, -M6, -M13, -M20, -M27, -M31, and -M37 CART maintained strong killing effect to A549 tumor cells with less ectopic expression of mesothelin (electroporated with 2 μg mesothelin mRNA). CART cells expressing anti-mesothelin scFv-M7, -M8, -M9, -M10, -M11, -M12, -M15, -M23, -M24, -M32, -M35, and -M38, which selectively showed high cytotoxicity toward tumor cells with high mesothelin expression but not those with low mesothelin expression had superior safety, as mesothelin is expressed in certain normal tissues.

FIG. 8. shows the killing curves of different mRNA-based anti-mesothelin CART cells, with A549-GFP tumor cells electroporated with 0 (upper panel), 2 μg (middle panel) or 10 μg (lower panel) mesothelin mRNA being the target cells (E/T ratio=10:1). As shown, that anti-mesothelin scFv-M12, -M24 and -M32 CART cells had moderate killing effect toward the A549 tumor cells with low mesothelin expression (2 μg group), but strong killing effect toward A549 tumor cells with high mesothelin expression (10 μg group). The results indicated that these CART cells would specifically target tumor cells with high mesothelin expression, and spare the normal tissues with low mesothelin expression.

FIG. 9 shows the FACS staining of OVCAR3 (human ovarian cancer cells), H226 (human lung carcinoma cells), ASPC1 (human pancreatic tumor cells), A549 (human lung cancer cells) and HCC70 (human breast cancer cells) with isotype control and anti-mesothelin mAb. As shown, certain cancer cells, including OVCAR3, H226 and ASPC1, express mesothelin at high level; A549 express mesothelin at low level, and HCC70 does not express mesothelin.

5.9.5 Example 5: Specific Activation of CART Cells by Mesothelin-Expression Cancer Cells CD107a is an early phase-activating marker for T cells. Activation of mesothelin CARTs by mesothelin-expressing tumor cells was measured by CD107a staining with the following procedures: 20 μl PE-CD107a mAb was added to each well of a 96-well plate; tumor cells were diluted to 2×10e6/ml and seeded on 96-well round plates (100 μl/well); CAR-T cells were diluted to 1×10e6/ml and seeded in 96-well round plates (100 μl/well); the plates were centrifuged at 500 rpm×5 min to attach cells and cultured at 37° C. for 1 hour; Golgi stop was diluted by 1500× with medium and added to each well (20 μl/well); cells were cultured at 37° C. for another 2.5 hours, stained with anti-CD3-APC and anti-CD8-FITC antibodies at 37° C. for 30 min, washed and analyze by flow cytometry.

FIG. 10 shows the CD107a staining of anti-mesothelin M12 and M32 CAR-T cells in the coculture and killing assay with OVCAR3, H226, ASPC1, A549 and HCC70. These data demonstrate that anti-mesothelin M12 and M32 CART cells were specifically activated by OVCAR3, H226, and ASPC1 (tumor cells with high mesothelin-expression level), but not A549 and HCC70 (tumor cell lines with low or no mesothelin expression).

What is claimed is:

1. An antibody or antigen-binding fragment thereof that specifically binds mesothelin and comprises a VL CDR1, a VL CDR2, a VL CDR3, a VH CDR1, a VH CDR2 and a VH CDR3, wherein
   (a) the VL CDR1, CDR2 and CDR3 have the amino acid sequences of SEQ ID NOs: 1, 2, and 3 respectively; and
   (b) the VH CDR1, CDR2 and CDR3 have the amino acid sequences of SEQ ID NOs: 4, 5, and 6 respectively.

2. The antibody or antigen-binding fragment of claim 1, comprising a VL and a VH, wherein the VL and VH have the amino acid sequences of SEQ ID NOs: 7 and 8, respectively.

3. The antibody or antigen-binding fragment of claim 1 that is a monoclonal antibody or antigen-binding fragment.

4. The antibody or antigen-binding fragment of claim 1 that is selected from the group consisting of an IgG1 antibody, an IgG2 antibody, an IgG3 antibody, and an IgG4 antibody.

5. The antibody or antigen-binding fragment of claim 1 that is selected from the group consisting of a Fab, a Fab', a F(ab')$_2$, a Fv, a scFv, and a (scFv)$_2$.

6. A Chimeric Antigen Receptor (CAR) that specifically binds mesothelin, comprising, from N-terminus to C-terminus:
   (a) a mesothelin-binding domain that comprises the antibody or antigen-binding fragment of claim 1;
   (b) a transmembrane domain; and
   (c) a cytoplasmic domain.

7. The CAR of claim 6, wherein the transmembrane domain is derived from CD8, CD28, CD3ζ, CD4, 4-1BB, OX40, ICOS, CTLA-4, PD-1, LAG-3, 2B4, BTLA, TCR α chain, TCR β chain, or TCR ζ chain, CD3ε, CD45, CD5, CD8, CD9, CD16, CD22, CD33, CD37, CD64, CD80, CD86, CD134, or CD154.

8. The CAR of claim 6, wherein the transmembrane domain comprises CD8 transmembrane region or CD28 transmembrane region.

9. The CAR of claim 6, wherein the cytoplasmic domain comprises a signaling domain derived from CD3ζ, FcRγ, FcγRIIa, FcRβ, CD3γ, CD3δ, CD3ε, CD5, CD22, CD79a, CD79b, DAP10, DAP12, or any combination thereof.

10. The CAR of claim 6, wherein the cytoplasmic domain further comprises a co-stimulatory domain derived from CD28, 4-1BB (CD137), OX40, ICOS, DAP10, 2B4, CD27, CD30, CD40, CD2, CD7, LIGHT, GITR, TLR, DR3, CD43, or any combination thereof.

11. The CAR of claim 6, wherein the cytoplasmic domain comprises a CD3ζ signaling domain and a 4-1BB co-stimulatory domain, or the cytoplasmic domain comprises a CD3ζ signaling domain and a CD28 co-stimulatory domain.

12. The CAR of claim 6, further comprising a CD8 hinge between the antibody or antigen-binding fragment and the transmembrane domain.

13. The CAR of claim 6, having the amino acid sequence of SEQ ID NO: 12.

14. A cell expressing the CAR of claim 6.

15. The cell of claim 14 that is an immune effector cell.

16. The cell of claim 14 that is derived from a cell isolated from peripheral blood or bone marrow.

17. The cell of claim 14 that is derived from a cell differentiated in vitro from a stem or progenitor cell is selected from the group consisting of a T cell progenitor cell, a hematopoietic stem and progenitor cell, a hematopoietic multipotent progenitor cell, an embryonic stem cell, and an induced pluripotent cell.

18. The cell of claim 14, which is a T cell or a NK cell.

19. The cell of claim 18 that is a cytotoxic T cell, a helper T cell, a gamma delta T, a CD4+/CD8+ double positive T cell, a CD4+ T cell, a CD8+ T cell, a CD4/CD8 double negative T cell, a CD3+ T cell, a naive T cell, an effector T cell, a helper T cell, a memory T cell, a regulator T cell, a Th0 cell, a Th1 cell, a Th2 cell, a Th3 (Treg) cell, a Th9 cell, a Th17 cell, a Thαβ helper cell, a Tfh cell, a stem memory TSCM cell, a central memory TCM cell, an effector memory TEM cell, or an effector memory TEMRA cell.

20. A method of treating cancer in a subject in need thereof, comprising administering to the subject a therapeutically effective amount of the antibody or antigen-binding fragment of claim 1.

21. A method of treating cancer in a subject in need thereof, comprising administering to the subject a therapeutically effective amount of the cell of claim 14.

22. The method of claim 20, further comprising Obtaining cells from the subject.

23. The method of claim 20, further comprising administering an additional therapy to the subject.

24. The method of claim 20, wherein the subject is a human.

25. The method of claim 20, wherein the cancer is a mesothelin-expressing cancer.

26. The method of claim 20, wherein the cancer is a solid tumor or a hematological cancer.

27. The method of claim 20, wherein the cancer is mesothelioma, pancreatic cancer and/or ovarian cancer.

28. The method of claim 27, wherein the mesothelioma is pleural mesothelioma, peritoneal mesothelioma, or pericardial mesothelioma; the pancreatic cancer is pancreatic ductal carcinoma; and/or the ovarian cancer is ovarian epithelial carcinoma.

* * * * *

SEQUENCE LISTING

```
Sequence total quantity: 25
SEQ ID NO: 1           moltype = AA  length = 11
FEATURE                Location/Qualifiers
REGION                 1..11
                       note = M12 VL CDR1
source                 1..11
                       mol_type = protein
                       organism = synthetic construct
SEQUENCE: 1
RASQGGGNYL A                                                          11

SEQ ID NO: 2           moltype = AA  length = 7
FEATURE                Location/Qualifiers
```

```
REGION                     1..7
                           note = M12 VL CDR2
source                     1..7
                           mol_type = protein
                           organism = synthetic construct
SEQUENCE: 2
GASKLQS                                                                    7

SEQ ID NO: 3               moltype = AA  length = 9
FEATURE                    Location/Qualifiers
REGION                     1..9
                           note = M12 VL CDR3
source                     1..9
                           mol_type = protein
                           organism = synthetic construct
SEQUENCE: 3
QQLNSYPVT                                                                  9

SEQ ID NO: 4               moltype = AA  length = 5
FEATURE                    Location/Qualifiers
REGION                     1..5
                           note = M12 VH CDR1
source                     1..5
                           mol_type = protein
                           organism = synthetic construct
SEQUENCE: 4
TYYIH                                                                      5

SEQ ID NO: 5               moltype = AA  length = 17
FEATURE                    Location/Qualifiers
REGION                     1..17
                           note = M12 VH CDR2
source                     1..17
                           mol_type = protein
                           organism = synthetic construct
SEQUENCE: 5
IINPSSGSTT YTQKFQG                                                        17

SEQ ID NO: 6               moltype = AA  length = 10
FEATURE                    Location/Qualifiers
REGION                     1..10
                           note = M12 VH CDR3
source                     1..10
                           mol_type = protein
                           organism = synthetic construct
SEQUENCE: 6
GETLRGYFDY                                                                10

SEQ ID NO: 7               moltype = AA  length = 107
FEATURE                    Location/Qualifiers
REGION                     1..107
                           note = M12 VL AA
source                     1..107
                           mol_type = protein
                           organism = synthetic construct
SEQUENCE: 7
AIRLTQSPSL LSASVGDRVT VTCRASQGGG NYLAWYQQKP GKAPKLLIYG ASKLQSGVPS         60
RFSGSGSGTE FTLTISSLQP EDFATYYCQQ LNSYPVTFGQ GTKVDIK                      107

SEQ ID NO: 8               moltype = AA  length = 119
FEATURE                    Location/Qualifiers
REGION                     1..119
                           note = M12 VH AA
source                     1..119
                           mol_type = protein
                           organism = synthetic construct
SEQUENCE: 8
EVQLVESGAE VKKPGASVKV SCKASGYTFT TYYIHWVRQA PGQGLEWMGI INPSSGSTTY         60
TQKFQGRVTM TRDTSTSTVY IELSGLRSED TAVYYCARGE TLRGYFDYWG QGTLVTVSS        119

SEQ ID NO: 9               moltype = DNA  length = 321
FEATURE                    Location/Qualifiers
misc_feature               1..321
                           note = M12 VL NT
source                     1..321
                           mol_type = other DNA
                           organism = synthetic construct
SEQUENCE: 9
gccatccggt tgacccagtc tccatccctc ctgtctgcat ctgtaggaga cagggtcacc         60
```

```
gtcacttgtc gggccagtca gggcggtggc aattatttag cctggtatca gcaaaaacca    120
gggaaagccc cgaaactcct gatctatggt gcatccaagt tgcaaagtgg ggtcccatcg    180
aggttcagcg gcagtggatc tgggacagaa ttcactctca caatcagcag tctgcagcct    240
gaagattttg caacttatta ctgtcaacag cttaatagtt accctgtcac ttttggccag    300
gggaccaaag tggatatcaa a                                              321

SEQ ID NO: 10           moltype = DNA   length = 357
FEATURE                 Location/Qualifiers
misc_feature            1..357
                        note = M12 VH NT
source                  1..357
                        mol_type = other DNA
                        organism = synthetic construct
SEQUENCE: 10
gaggtgcagc tggtggagtc tggggctgag gtgaagaagc ctggggcctc agtgaaggtt    60
tcctgcaagg catctggata caccttcacc acctactata tacactgggt gcgacaggcc    120
cctggacaag gcttgagtg gatgggaata atcaacccta gtagtggtag cactacctac    180
acacagaagt tccagggcag agtcaccatg accagggaca cgtccacgag cacagtgtac    240
attgaactga gcggcctgag atctgaagac acggccgtgt attactgtgc ccgaggggag    300
acgcttcggg gctactttga ctactggggc cagggaaccc tggtcaccgt ctcttca       357

SEQ ID NO: 11           moltype = AA    length = 241
FEATURE                 Location/Qualifiers
REGION                  1..241
                        note = M12 scFv
source                  1..241
                        mol_type = protein
                        organism = synthetic construct
SEQUENCE: 11
AIRLTQSPSL LSASVGDRVT VTCRASQGGG NYLAWYQQKP GKAPKLLIYG ASKLQSGVPS    60
RFSGSGSGTE FTLTISSLQP EDFATYYCQQ LNSYPVTFGQ GTKVDIKGGG GSGGGGSGGG    120
GSEVQLVESG AEVKKPGASV KVSCKASGYT FTTYYIHWVR QAPGQGLEWM GIINPSSGST    180
TYTQKFQGRV TMTRDTSTST VYIELSGLRS EDTAVYYCAR GETLRGYFDY WGQGTLVTVS    240
S                                                                    241

SEQ ID NO: 12           moltype = AA    length = 485
FEATURE                 Location/Qualifiers
REGION                  1..485
                        note = M12 CAR AA
source                  1..485
                        mol_type = protein
                        organism = synthetic construct
SEQUENCE: 12
MALPVTALLL PLALLLHAAR PAIRLTQSPS LLSASVGDRV TVTCRASQGG GNYLAWYQQK    60
PGKAPKLLIY GASKLQSGVP SRFSGSGSGT EFTLTISSLQ PEDFATYYCQ QLNSYPVTFG    120
QGTKVDIKGG GGSGGGGSGG GGSEVQLVES GAEVKKPGAS VKVSCKASGY TFTTYYIHWV    180
RQAPGQGLEW MGIINPSSGS TTYTQKFQGR VTMTRDTSTS TVYIELSGLR SEDTAVYYCA    240
RGETLRGYFD YWGQGTLVTV SSTTTPAPRP PTPAPTIASQ PLSLRPEACR PAAGGAVHTR    300
GLDFACDIYI WAPLAGTCGV LLLSLVITLY CKRGRKKLLY IFKQPFMRPV QTTQEEDGCS    360
CRFPEEEEGG CELRVKFSRS ADAPAYKQGQ NQLYNELNLG RREEYDVLDK RRGRDPEMGG    420
KPRRKNPQEG LYNELQKDKM AEAYSEIGMK GERRRGKGHD GLYQGLSTAT KDTYDALHMQ    480
ALPPR                                                                485

SEQ ID NO: 13           moltype = DNA   length = 1458
FEATURE                 Location/Qualifiers
misc_feature            1..1458
                        note = M12 CAR NT
source                  1..1458
                        mol_type = other DNA
                        organism = synthetic construct
SEQUENCE: 13
atggccttac cagtgaccgc cttgctcctg ccgctggcct tgctgctcca cgccgccagg    60
ccggccatcc ggttgaccca gtctccatcc ctcctgtctg catctgtagg agacagggtc    120
accgtcactt gtcgggccag tcagggcggt ggcaattatt tagcctggta tcagcaaaaa    180
ccagggaaag ccccgaaact cctgatctat ggtgcatcca agttgcaaag tggggtccca    240
tcgaggttca gcggcagtgg atctgggaca gaattcactc tcacaatcag cagtctgcag    300
cctgaagatt ttgcaactta ttactgtcaa cagcttaata gttaccctgt cacttttggc    360
caggggacca aagtggatat caaagtggt ggtggttctg gcggcggcgg ctccggaggt    420
ggtggatccg aggtgcagct ggtggagtct ggggctgagg tgaagaagcc tggggcctca    480
gtgaaggttt cctgcaaggc atctggatac accttcacca cctactatat acactgggtg    540
cgacaggccc ctggacaagg cttgagtgg atgggaataa tcaacccta gtagtggtag    600
cactacctac acagaagtt ccagggcaga gtcaccatga ccagggacac gtccacgagc    660
acagtctaca ttgaactgag cggcctgaga tctgaagaca cggccgtgta ttactgtgcc    720
cgaggggaga cgcttcgggg ctactttgac tactggggc agggaacc tggtcaccgt    780
ctcttcaacca cgacgccagc gccgcgacca ccaacaccgg cgccaccat cgtcgcag     840
cccctgtccc tgcgcccaga ggcgtgccgg ccagcgcgg gggcgcagt gcacacgagg    900
gggctggact cgcctgtga tatctacat tgggcgccct tggccgggac ttgtgggtc     960
cttctcctgt cactggttat caccttac tgcaaacggg gcagaaagaa actcctgtat    1020
atattcaaac aaccattat gagaccagta caaactactc aagaggaaga tggctgtagc    1080
```

```
tgccgatttc cagaagaaga agaaggagga tgtgaactga gagtgaagtt cagcaggagc   1140
gcagacgccc ccgcgtacaa gcagggccag aaccagctct ataacgagct caatctagga   1200
cgaagagagg agtacgacgt tttggacaag agacgtggcc gggacccctga gatgggggga   1260
aagccgagaa ggaagaaccc tcaggaaggc ctgtacaatg aactcagaa agataagatg   1320
gcggaggcct acagtgagat tgggatgaaa ggcgagcgcc ggaggggcaa ggggcacgat   1380
ggcctttacc agggtctcag tacagccacc aaggacacct cgacgccct tcacatgcag   1440
gccctgcccc ctcgctaa                                                 1458

SEQ ID NO: 14            moltype = AA   length = 5
FEATURE                  Location/Qualifiers
REGION                   1..5
                         note = linker
REPEAT                   1..5
                         note = (GGGGS)n, n=1,2,3,4,or 5
source                   1..5
                         mol_type = protein
                         organism = synthetic construct
SEQUENCE: 14
GGGGS                                                                       5

SEQ ID NO: 15            moltype = AA   length = 5
FEATURE                  Location/Qualifiers
REGION                   1..5
                         note = linker
REPEAT                   1..5
                         note = (EAAAK)n, n=1,2,3,4,or 5
source                   1..5
                         mol_type = protein
                         organism = synthetic construct
SEQUENCE: 15
EAAAK                                                                       5

SEQ ID NO: 16            moltype =    length =
SEQUENCE: 16
000

SEQ ID NO: 17            moltype = AA   length = 15
FEATURE                  Location/Qualifiers
REGION                   1..15
                         note = linker
source                   1..15
                         mol_type = protein
                         organism = synthetic construct
SEQUENCE: 17
GGGGSGGGGS GGGGS                                                           15

SEQ ID NO: 18            moltype = AA   length = 164
FEATURE                  Location/Qualifiers
REGION                   1..164
                         note = Human CD3zeta
source                   1..164
                         mol_type = protein
                         organism = synthetic construct
SEQUENCE: 18
MKWKALFTAA ILQAQLPITE AQSFGLLDPK LCYLLDGILF IYGVILTALF LRVKFSRSAD          60
APAYQQGQNQ LYNELNLGRR EEYDVLDKRR GRDPEMGGKP QRRKNPQEGL YNELQKDKMA         120
EAYSEIGMKG ERRRGKGHDG LYQGLSTATK DTYDALHMQA LPPR                          164

SEQ ID NO: 19            moltype = AA   length = 220
FEATURE                  Location/Qualifiers
REGION                   1..220
                         note = Human CD28
source                   1..220
                         mol_type = protein
                         organism = synthetic construct
SEQUENCE: 19
MLRLLLALNL FPSIQVTGNK ILVKQSPMLV AYDNAVNLSC KYSYNLFSRE FRASLHKGLD          60
SAVEVCVVYG NYSQQLQVYS KTGFNCDGKL GNESVTFYLQ NLYVNQTDIY FCKIEVMYPP         120
PYLDNEKSNG TIIHVKGKHL CPSPLFPGPS KPFWVLVVVG GVLACYSLLV TVAFIIFWVR         180
SKRSRLLHSD YMNMTPRRPG PTRKHYQPYA PPRDFAAYRS                               220

SEQ ID NO: 20            moltype = AA   length = 255
FEATURE                  Location/Qualifiers
REGION                   1..255
                         note = Human 4-1BB
source                   1..255
                         mol_type = protein
                         organism = synthetic construct
SEQUENCE: 20
```

```
MGNSCYNIVA TLLLVLNFER TRSLQDPCSN CPAGTFCDNN RNQICSPCPP NSFSSAGGQR    60
TCDICRQCKG VFRTRKECSS TSNAECDCTP GFHCLGAGCS MCEQDCKQGQ ELTKKGCKDC   120
CFGTFNDQKR GICRPWTNCS LDGKSVLVNG TKERDVVCGP SPADLSPGAS SVTPPAPARE   180
PGHSPQIISF FLALTSTALL FLLFFLTLRF SVVKRGRKKL LYIFKQPFMR PVQTTQEEDG   240
CSCRFPEEEE GGCEL                                                   255

SEQ ID NO: 21            moltype = AA  length = 235
FEATURE                  Location/Qualifiers
REGION                   1..235
                         note = Human CD8
source                   1..235
                         mol_type = protein
                         organism = synthetic construct
SEQUENCE: 21
MALPVTALLL PLALLLHAAR PSQFRVSPLD RTWNLGETVE LKCQVLLSNP TSGCSWLFQP    60
RGAAASPTFL LYLSQNKPKA AEGLDTQRFS GKRLGDTFVL TLSDFRRENE GYYFCSALSN   120
SIMYFSHFVP VFLPAKPTTT PAPRPPTPAP TIASQPLSLR PEACRPAAGG AVHTRGLDFA   180
CDIYIWAPLA GTCGVLLLSL VITLYCNHRN RRRVCKCPRP VVKSGDKPSL SARYV        235

SEQ ID NO: 22            moltype = DNA  length = 22
FEATURE                  Location/Qualifiers
source                   1..22
                         mol_type = other DNA
                         organism = synthetic construct
primer_bind              1..22
                         note = Forward primer sequence
SEQUENCE: 22
tgcagctggc acgacaggtt tc                                            22

SEQ ID NO: 23            moltype = DNA  length = 19
FEATURE                  Location/Qualifiers
source                   1..19
                         mol_type = other DNA
                         organism = synthetic construct
primer_bind              1..19
                         note = reverse primer sequence
SEQUENCE: 23
cgtcagactg tagcacgtt                                                19

SEQ ID NO: 24            moltype = DNA  length = 20
FEATURE                  Location/Qualifiers
source                   1..20
                         mol_type = other DNA
                         organism = synthetic construct
primer_bind              1..20
                         note = Forward primer sequence
SEQUENCE: 24
aacaattgaa ttcaggagga                                               20

SEQ ID NO: 25            moltype = DNA  length = 19
FEATURE                  Location/Qualifiers
source                   1..19
                         mol_type = other DNA
                         organism = synthetic construct
primer_bind              1..19
                         note = reverse primer sequence
SEQUENCE: 25
cctcctaaga agcgtagtc                                                19
```